United States Patent [19]

Gearing et al.

[11] Patent Number: 5,420,247
[45] Date of Patent: May 30, 1995

[54] LEUKEMIA INHIBITORY FACTOR RECEPTORS AND FUSION PROTEINS

[75] Inventors: David P. Gearing, Seattle; Patricia M. Beckmann, Poulsbo, both of Wash.

[73] Assignee: Immunex Corporation, Seattle, Wash.

[21] Appl. No.: 119,780

[22] Filed: Sep. 10, 1993

Related U.S. Application Data

[60] Division of Ser. No. 943,843, Sep. 11, 1992, Pat. No. 5,284,755, which is a continuation-in-part of Ser. No. 670,608, Mar. 13, 1991, abandoned, which is a continuation-in-part of Ser. No. 626,725, Dec. 13, 1990, abandoned.

[51] Int. Cl.$^6$ ............................................. C07K 13/00
[52] U.S. Cl. ............................... 530/350; 530/402; 530/387.3; 530/391.1; 530/388.23; 536/23.51
[58] Field of Search ............... 530/350, 402; 435/64.1, 435/64.7; 536/23.4, 23.5; 514/12

[56] References Cited

U.S. PATENT DOCUMENTS

| | | | |
|---|---|---|---|
| 4,518,584 | 5/1985 | Mark et al. | 424/85 |
| 4,675,285 | 6/1987 | Clark et al. | 435/6 |
| 5,071,972 | 12/1991 | Larsen | 536/27 |
| 5,155,027 | 10/1992 | Sledziewski et al. | 435/69.7 |

FOREIGN PATENT DOCUMENTS

0212914 4/1987 European Pat. Off. .
0276846 3/1988 European Pat. Off. .

OTHER PUBLICATIONS

Allan et al., "Osteoblasts display receptors for and responses to leukemia-inhibitory factor", *J. Cell Physiol.* 145:110–119; 1990.
Williams et al., "Myelokd leukemia inhibitory factor maintains the development potential of embryonic stem cells", *Nature* 336:684–687; 1988.
Tomida et al., "Inhibition of development of NA+ dependent hexose transport in renal epithelial LLC-PK1 cells . . . for myeloid leukemic cells/leukemia inhibitory factor", *FEBS* 268:261–264; 1990.
Gearing et al., "Expression cloning of a receptor for human granulocyte–macrophage colonystimulating factor", *EMBO J.* 8:3667–3676; 1989.
Yamasaki et al., "Cloning and Expression of the Human Interleukin–6 Receptor", *Science* 241:825–828; 1988.
Cosman, "Expression Cloning of Cytokines and Cytokine Receptors by Screening Pools of cDNA Clones", *DNA & Prot. Eng. Tech.* 2:1–28, 1990.
Gearing et al., "Leukemia inhibitory factor receptor is structurally related to the IL–6 signal transducer", gp130, *EMBO J.* 10:2839; 1991.
Sims et al., "cDNA Expression Cloning of the IL–1 Receptor: a Member of the Immunoglobulin Superfamily", *Science* 241:585–589; 1988.
Belyavsky et al., "PCR-based cDNA Library Construction; General cDNA Libraries at the Level of a Few Cells", *Nucl. Acids Res.* 17: Aug. 1989.
Smith et al., "Blocking of H1V–I Infectivity by a Soluble, Secreted Form of the CD4 Antigen", *Science* 238:1704–1707; 1987.
Baumann and Wong, "Hepatocyte-Stimulating Factor III Shares Structural and Functional Identity with Leukemia Inhibitory Factor", *J. Immunol.* 143:1163; 1989.
Yamamori et al., "The Clolinergic Neuronal Differentiation Factor from Heart Cells is Identical to Leukemia Inhibitory Factor", *Science* 246:1412; 1990.
Mori et al., "Purification of a Lipoprotein Lipase-Inhibiting Protein Produced by a Melanoma Cell Line Associatd with Cancer Cachexia" *Biochem. Biophys. Res. Comm.* 160:1085; 1989.
Moreau et al., "Leukaemia inhibitory factor is identical (List continued on next page.)

*Primary Examiner*—Garnette D. Draper
*Assistant Examiner*—John D. Ulm
*Attorney, Agent, or Firm*—Kathryn A. Anderson; Christopher L. Wight

[57] ABSTRACT

Leukemia inhibitory factor receptor (LIF-R) proteins, DNAs and expression vectors encoding LIF-R, and processes for producing LIF-R as products of recombinant cell culture, are disclosed.

6 Claims, 8 Drawing Sheets

OTHER PUBLICATIONS to the myeloid growth factor human interleukin for DA cells", *Nature* 336:690; 1988.

Abe et al., "Macrophage Differentiation Inducing Factor from Human Monocytic Cells is Equivalent to Murine Leukemia Inhibitor Factor", *J. Biol. Chem.* 264:8941; 1989.

Smith and Hooper, "Buffalo Rat Liver Cells Produce a Diffusible Activity Which Inhibits the Differentiation of Murine Embryonal Carcinoma and Embryonic Stem Cells", *Devel. Biol.* 121:1; 1987.

Koopman and Cotton, "A Factor Produced by Feeder Cells which Inhibits Embryonal Carcinoma Cell Differentiation", *Exp. Cell. Res.* 154:233; 1984.

Tomida et al., "Purification of a Factor Inducing Differentiation of Mouse Myeloid Leukemic M1 Cells from Conditioned Medium of Mouse Fibroblast L929 Cells" *J. Biol. Chem.* 259:10978; 1984.

Hilton et al., "Resolution and Purification of Three Distinct Factors produced by Krebs Ascites Cells Which Have Differentiation-inducing Activity on Murine Myeloid Lekemic Cells Lines", *J. Biol. Chem.* 263:9238; 1988.

Gough et al., "Molecular cloning and expression of the human homologue of the murine gene encoding myeloid leukemia-inhibitory factor", *Proc. Natl. Acad. Sci. USA* 85:2623; 1988.

Metcalf et al., "Effects of Injected Leukemia Inhibitory Factor on Hematopoietic and Other Tissues on Mice", *Blood* 76:50; 1990.

Hilton et al., "Specific Binding of Murine Leukemia Inhibitory Factor to Normal and Leukemic Monocytic Cells", *Proc. Natl. Acad. Sci. USA* 85:5971; 1988.

Jacques et al., "High-Affinity Receptors for Human HILDA/LIF on Human Cell Lines", *5th Symposium sur les Marquers de l'Inflammation*, (Lyon 25-27 Sep. 1990).

Hilton et al., "Distribution of LIF receptors during embryogenesis", Article 45, *Annual Review*, The Walter and Eliza Hall Institute of Medical Research; 1990.

Brown et al., "Analysis of leukaemia inhibitory factor expression", Article 55, *Annual Review*, The Walter and Eliza Hall Institute of Medical Research; Jun. 1989–Jul. 1990.

Stewart et al., "Blastocyte implantation depends on maternal expression of leukaemia inhibitory factor", *Nature* 359:76-79; 1992.

Heath, "Can there be life without LIF?", *Nature* 359:17; 1992.

Hilton et al., "Distribution and Comparison of Receptors for Leukemia Inhibitory Factor on Murine Hematopoietic and Hepatic Cells", *J. Cell. Phys.* 146:207-215; 1991.

Gearing and Bruce, "Oncostatin M Binds the High-Affinity Leukemia Inhibitory Factor Receptor", *The New Biologist* 4:61-65; 1992.

Gearing, "Leukemia Inhibitory Factor: Does the Cap Fit?", *Ann. of the N.Y. Acad. Sci.* 628:9-18; 1991.

Gearing et al., "The IL-6 Signal Transducer, gp130: An Oncostatin M Receptor and Affinity Converter for the LIF Receptor ", *Science* 255:1434-1437; 1992.

Aruffo and Seed, "Molecular cloning of a CD28 cDNA by a high-efficiency COS cell expression system", *Proc. Natl. Acad. Sci. USA* 84:8573-8577; 1987.

Lesslauer et al., "Recombinant soluble tumor necrosis factor receptor proteins protect mice from lipopolysaccharide-induced lethality", *Eur. J. Immunol.* 21:2883-2886; 1991.

Peppel and Beutler, "Chimaeric TNF-Receptor-IgG Molecule Acts as Soluble Inhibitor of TNF Mediated Cytotoxicity", J. Cell. Biochem. (Abstr), Suppl. 15F; Apr. 1991.

```
  1                                                                                                    AGATCTTGGAACGAGACGACCTGCTCTCTCTCCCAGAACGTGTCTCT   131
132 GCTGCAAGCGACCGGGCCCTTGCCTCTCCCAGAACTGCACTTGCAAGACCATTATCAACTCCCAGTCCCTAATCCCAGCTCCTCAAGACCATTATCAACTCCCAGTCCCTAATCCCAGCTCCTCAAGACCATTATCAACTCCCAGTCCCTAATCCCAGCTCCTCCAGGACTGCACTGCATTGCACAG  178
179 ATG ATG GAT ATT TAC GTA TGT TTG AAA CGA CCA TCC TGG ATG GTG GAC AAT AAA AGA ATG AGG ACT GCT TCA AAT TTC CAG CTG TTA TCA ACA TTT  277
  1 Met Met Asp Ile Tyr Val Cys Leu Lys Arg Pro Ser Trp Met Val Asp Asn Lys Arg Met Arg Thr Ala Ser Asn Phe Gln Leu Leu Ser Thr Phe  33
                                                                                                                                *
278 ATT CTT CTA TAT CTA ATG AAT CAA GTA AAT AGC CAG AAA AAG GGG GCT CCT CAT GAT TTG AAG TGT GTA ACT AAC AAT TTG CAA GTG TGG AAC TGT TCT  376
 34 Ile Leu Leu Tyr Leu Met Asn Gln Val Asn Ser Gln Lys Lys Gly Ala Pro His Asp Leu Lys Cys Val Thr Asn Asn Leu Gln Val Trp Asn Cys Ser  66
                                                                              *
377 TGG AAA GCA CCC TCT GGA ACA GGC CGT GGT ACT GAT TAT GAA GTT TGC ATT GAA AAC ACC TCC CGT TCT TGT TAT CAG TTG GAG AAA ACC AGT ATT AAA  475
 67 Trp Lys Ala Pro Ser Gly Thr Gly Arg Gly Thr Asp Tyr Glu Val Cys Ile Glu Asn Arg Ser Arg Ser Cys Tyr Gln Leu Glu Lys Thr Ser Ile Lys  99
                                                                              *
476 ATT CCA GCT CTT TCA CAT GGT GAT TAT GAA ATA ACA ATA AAT TCT CTA CAT GAT TTT GGA AGT TCT ACA AGT TCT AAA TTA TAC CTA ACC TCT ACA TTA  574
100 Ile Pro Ala Leu Ser His Gly Asp Tyr Glu Ile Thr Ile Asn Ser Leu His Asp Phe Gly Ser Ser Thr Ser Lys Leu Tyr Leu Thr Ser Thr Leu  132
                                              *
575 TCC TTA ATT CCA GAT ACT CCA GAG ATC TTG CTT GAT TTG TCT AAT TTG TCT GCT GAT TTC TCA ACC TCT ACA TTA TAC CTA AAG TGG AAC GAC AGG GGT TCA GTT TTT CCA  673
133 Ser Leu Ile Pro Asp Thr Pro Glu Ile Leu Leu Asn Leu Ser Ala Asp Phe Ser Thr Ser Thr Leu Tyr Leu Lys Trp Asn Asp Arg Gly Ser Val Phe Pro  165
                                                                                                *
674 CAC CGC TCA AAT GTT ATC TGG GAA ATT AAA GTT TGG GAA ATT AAA GTT CGT AAA GAG AGT CTC GTA AAA TTA GTG ACC AAC ACA ACT CTG AAT GGC AAA GAT  772
166 His Arg Ser Asn Val Ile Trp Glu Ile Lys Val Trp Glu Ile Lys Val Arg Lys Glu Ser Leu Val Lys Leu Val Thr Asn Thr Thr Leu Asn Gly Lys Asp  198

773 ACA CTT CAT CAC TGG AGT TGG GCC TCA GAT ATG GAA TGT ATT CAT TTT GTG GAA ATT AGA TGC TAC ATT GAC AAT TTT CAT TTT TCT GGT  871
100 Thr Leu His His Trp Ser Trp Ala Ser Asp Met Pro Leu Glu Cys Ala Ile His Phe Val Glu Ile Arg Cys Tyr Ile Asp Asn Leu His Phe Ser Gly  231
```

FIGURE 2a

```
872   CTC GAA GAG TGG AGT GAC TGG AGC CCT GTG AAG AAC ATT TCT TGG ATA CCT GAT TCT CAG ACT AAG GTT TTT CCT CAA GAT AAA GTG ATA CTT GTA GGC   970
232   Leu Glu Glu Trp Ser Asp Trp Ser Pro Val Lys Asn Ile Ser Trp Ile Pro Asp Ser Gln Thr Lys Val Phe Pro Gln Asp Lys Val Ile Leu Val Gly   264

971   TCA GAC ATA ACA TTT TGT TGT GTG AGT CAA GAA AAA GTG TTA TCA GCA CTG ATT GGC CAT ACA AAC TGC CCC TTG ATC CAT CTT GAT GGG GAA AAT GTT  1069
265   Ser Asp Ile Thr Phe Cys Cys Val Ser Gln Glu Lys Val Leu Ser Ala Leu Ile Gly His Thr Asn Cys Pro Leu Ile His Leu Asp Gly Glu Asn Val  297

1070  GCA ATC AAG ATT CGT AAT ATT TCT GTT TCT GCA AGT AGT GGA ACA AAT GTA GTT TTT ACA ACC GAA GAT AAC ATA TTT GGA ACC GTT TTT GCT GGA      1168
298   Ala Ile Lys Ile Arg Asn Ile Ser Val Ser Ala Ser Ser Gly Thr Asn Val Val Phe Thr Thr Glu Asp Asn Ile Phe Gly Thr Val Phe Ala Gly      330

1169  TAT CCA CCA GAT ACT CCT CAA CAA CTG AAT TGT GAG ACA CAT GAT TTA AAA GAA ATT ATA TGT AGT TGG AAT CCA GGA AGG GTG ACA GCG TTG GTG GGC  1267
331   Tyr Pro Pro Asp Thr Pro Gln Gln Leu Asn Cys Glu Thr His Asp Leu Lys Glu Ile Ile Cys Ser Trp Asn Pro Gly Arg Val Thr Ala Leu Val Gly  363

1268  CCA CGT GCT ACA AGC TAC ACT TTA GTT GAA AGT TTT TCA GGA AAA TAT GTT AGA CTT AAA AGA GCT GAA GCA CCT ACA AAC GAA TAT CAA TTA TTA      1366
364   Pro Arg Ala Thr Ser Tyr Thr Leu Val Glu Ser Phe Ser Gly Lys Tyr Val Arg Leu Lys Arg Ala Glu Ala Pro Thr Asn Glu Tyr Gln Leu Leu      396

1367  TTT CAA ATG CTT CCA AAT CAA GAA ATA TAT AAT TTT ACT TTG AAT GCT CAC AAT GCA TCA CAA ACA ATT TTA GTT AAT TCA ACA GCT GTT AAT ATA ACT GAA  1465
397   Phe Gln Met Leu Pro Asn Gln Glu Ile Tyr Asn Phe Thr Leu Asn Ala His Asn Ala Ser Gln Thr Ile Leu Val Asn Ser Thr Ala Val Asn Ile Thr Glu  429

1466  AAA GTT TAT CCC CAT ACT CCT ACT TCA TTC AAA GTG AAG GAT ATT AAT TCA ACA GCT GTT AAA CTT TCT TGG CAT TTA CCA GGC AAC TTT GCA AAG ATT  1564
430   Lys Val Tyr Pro His Thr Pro Thr Ser Phe Lys Val Lys Asp Ile Asn Ser Thr Ala Val Lys Leu Ser Trp His Leu Pro Gly Asn Phe Ala Lys Ile  462
```

FIGURE 2b

```
1565  AAT TTT TTA TGT GAA ATT GAA ATT AAG AAA TCT AAT TCA GTA CAA GAG CAG CGG AAT GTC ACA ATC AAA GGA GTA GAA AAT TCA AGT TAT CTT GTT GCT  1663
463   Asn Phe Leu Cys Glu Ile Glu Ile Lys Lys Ser Asn Ser Val Gln Glu Gln Arg Asn Val Thr Ile Lys Gly Val Glu Asn Ser Ser Tyr Leu Val Ala  495

1664  CTG GAC AAG TTA AAT CCA TAC ACT CTA TAT ACT TTT CGG ATT CGT TGT TCT ACT GAA ACT TTC TGG AAA TGG AGC AAT AAA AAA CAA CAT  1762
496   Leu Asp Lys Leu Asn Pro Tyr Thr Leu Tyr Thr Phe Arg Ile Arg Cys Ser Thr Glu Thr Phe Trp Lys Trp Ser Asn Lys Lys Gln His  528

1763  TTA ACA ACA GAA GCC AGT CCT TCA AAG GGG CCT GAT ACT TGG AGA GAG TGG AGT TCT GAT GGA AAA AAT TTA ATA ATC TAT TGG AAG CCT TTA CCC ATT  1861
529   Leu Thr Thr Glu Ala Ser Pro Ser Lys Gly Pro Asp Thr Trp Arg Glu Trp Ser Ser Asp Gly Lys Asn Leu Ile Ile Tyr Trp Lys Pro Leu Pro Ile  561

1862  AAT GAA GCT AAT GGA AAA ATA CTT TCC TAC AAT GTA TCG TGT TCA TCG TGT TCA GAT GAG GAA ACA CAG TCC CTT TCT GAA ATC CCT GAT CCT CAG CAC AAA GCA  1960
562   Asn Glu Ala Asn Gly Lys Ile Leu Ser Tyr Asn Val Ser Cys Ser Ser Asp Glu Glu Thr Gln Ser Leu Ser Glu Ile Pro Asp Pro Gln His Lys Ala  594

1961  GAG ATA CGA CTT GAT AAG AAT GAC TAC ATC ATC AGC GTA GCT AAA AAT TCT GTG GGC TCA TCA CCA CCT TCC AAA ATA GCG AGT ATG GAA ATT CCA  2059
595   Glu Ile Arg Leu Asp Lys Asn Asp Tyr Ile Ile Ser Val Ala Lys Asn Ser Val Gly Ser Ser Pro Pro Ser Lys Ile Ala Ser Met Glu Ile Pro  627

2060  AAT GAT GAT CTC AAA ATA GAA CAA GTT GTT GGG ATG GGA AAG GGG ATT CTC CTC ACC TGG CAT TAC GAC CCC AAC ATG ACT TGC GAC TAC GTC ATT AAG  2158
628   Asn Asp Asp Leu Lys Ile Glu Gln Val Val Gly Met Gly Lys Gly Ile Leu Leu Thr Trp His Tyr Asp Pro Asn Met Thr Cys Asp Tyr Val Ile Lys  660

2159  TGG TGT AAC TCG TCT CGG TCG GAA CCA TGC CTT ATG GAC TGG AGA AAA GTT CCC TCA AAC AGC ACT GAA ACT GTA ATA GAA TCT GAT GAG TTT CGA CCA  2257
661   Trp Cys Asn Ser Ser Arg Ser Glu Pro Cys Leu Met Asp Trp Arg Lys Val Pro Ser Asn Ser Thr Glu Thr Val Ile Glu Ser Asp Glu Phe Arg Pro  693
```

FIGURE 2c

```
2258 GGT ATA AGA TAT AAT TTT TTC CTG TAT GGA TGC AGA AAT CAA GGA TAT CAA TTA CGC TCC ATG ATT GGA TAT ATA GAA GAA TTG GCT CCC ATT GTT    2356
 694 Gly Ile Arg Tyr Asn Phe Phe Leu Tyr Gly Cys Arg Asn Gln Gly Tyr Gln Leu Arg Ser Met Ile Gly Tyr Ile Glu Glu Leu Ala Pro Ile Val    726
                                           *
2357 GCA CCA AAT TTT ACT GTT GAG GAT ACT TCT GCA GAT TCG ATA TTA GTA AAA TGG GAA GAC ATT CCT GTG GAA GAA CTT AGA GGC TTT TTA AGA GGA TAT    2455
 727 Ala Pro Asn Phe Thr Val Glu Asp Thr Ser Ala Asp Ser Ile Leu Val Lys Trp Glu Asp Ile Pro Val Glu Glu Leu Arg Gly Phe Leu Arg Gly Tyr   759

2456 TTG TTT TAC TTT GGA AAA AAG GAA AGA GAC ACA TCT AAG ATG AGG GTT TTA GAA TCA GGT CGT TCT GAC ATA AAA GTT AAG AAT ATT ACT GAC ATA TCC    2554
 760 Leu Phe Tyr Phe Gly Lys Lys Glu Arg Asp Thr Ser Lys Met Arg Val Leu Glu Ser Gly Arg Ser Asp Ile Lys Val Lys Asn Ile Thr Asp Ile Ser   792
                                                                                              *
2555 CAG AAG ACA ATT GCT GAT CTT GAA GGT TTA CAA ACA AGT TAC CAC CTG GTC TTG CGA GCC TAT ACA GAT GGT GGA GTG GGC CCG GAG AAG AGT ATG    2653
 793 Gln Lys Thr Ile Ala Asp Leu Glu Gly Leu Gln Thr Ser Tyr His Leu Val Leu Arg Ala Tyr Thr Asp Gly Gly Val Gly Pro Glu Lys Ser Met     825

2654 TAT GTG GGT GAC AAG GAA AAT TCT GTG GGA TTA ATT ATT GCC ATT CTC ATC CCA GTG GCA GTG GCT GTC ATT GTT GGA GTG GTG ACA AGT AGT TTT TGC    2752
 826 Tyr Val Val Thr Lys Glu Asn Ser Val Gly Leu Ile Ile Ala Ile Leu Ile Pro Val Ala Val Ala Val Ile Val Gly Val Val Thr Ser Ile Leu Cys  858

2753 TAT CGG AAA CGA GAA TGG ATT AAA GAA ACC TTC TAC CCT GAT ATT CAG ACC TTT CAA AAG AGT GTC TGT GAG GGA    2851
 859 Tyr Arg Lys Arg Glu Trp Ile Lys Glu Thr Phe Tyr Pro Asp Ile Gln Thr Phe Gln Lys Ser Val Cys Glu Gly   891

2852 AGC AGT GCT CTT AAA ACA TTG GAA ATG AAT CCT TGT ACC CCA AAT GTT GAG GTT CTG GAA ACT CGA TCA GCA TTT CCT AAA ATA GAA GAT ACA GAA    2950
 892 Ser Ser Ala Leu Lys Thr Leu Glu Met Asn Pro Cys Thr Pro Asn Val Glu Val Leu Glu Thr Arg Ser Ala Phe Pro Lys Ile Glu Asp Thr Glu     924
```

FIGURE 2d

```
2951 ATA ATT TCC CCA GTA GCT GAG CGT CCT GAA GAT CGC CCT GAT GCA GAG CCT GAA AAC CAT GTG GTT GTG TCC TAT TGT CCA CCC ATT AGT GAA GAA   3049
 925 Ile Ile Ser Pro Val Ala Glu Arg Pro Glu Asp Arg Pro Asp Ala Glu Pro Glu Asn His Val Val Val Ser Tyr Cys Pro Pro Ile Glu Glu Glu    957
                                                                                                                    ↱
3050 ATA CCA AAC CCA GCC GCA GAT GAA GCT GGA GGG ACT GCA GAG GTT ATT TAC ATT GAT GTT CAG TCG ATG TAT CAG CCT CAA GCA AAA CCA GAA GAA   3148
 958 Ile Pro Asn Pro Ala Ala Asp Glu Ala Gly Gly Thr Ala Glu Val Ile Tyr Ile Asp Val Gln Ser Met Tyr Gln Pro Gln Ala Lys Pro Glu Glu    990
                                                                          *
3149 CAA GAA AAT GAC CCT GTA GGA GGG GCA GGC TAT AAG CCA CAG ATG CAC CTC CCC ATT AAT TCT ACT GTG GAA GAT ATA GCT GCA GAA GAG GAC TTA GAT   3247
 991 Gln Glu Asn Asp Pro Val Gly Gly Ala Gly Tyr Lys Pro Gln Met His Leu Pro Ile Asn Ser Thr Val Glu Asp Ile Ala Ala Glu Glu Asp Leu Asp   1023

3248 AAA ACT GCG GGT TAC AGA CCT CAG GCC AAT GTA AAT ACA TGG AAT TTA GTG TCT CCA GAC TCT CCA AGA TCC ATA GAC AGC AAC AGT GAG ATT GTC TCA   3346
1024 Lys Thr Ala Gly Tyr Arg Pro Gln Ala Asn Val Asn Thr Trp Asn Leu Val Ser Pro Asp Ser Pro Arg Ser Ile Asp Ser Asn Ser Glu Ile Val Ser   1056

3347 TTT GGA AGT CCA TGC TCC ATT AAT TCC CGA CAA TTT TTG ATT CCT AAA GAT GAA GAC TCT CCT AAA TCT AAT GGA GGA GGG TGG TCC TTT ACA AAC   3445
1057 Phe Gly Ser Pro Cys Ser Ile Asn Ser Arg Gln Phe Leu Ile Pro Lys Asp Glu Asp Ser Pro Lys Ser Asn Gly Gly Gly Trp Ser Phe Thr Asn   1089

3446 TTT TTT CAG AAC AAA CCA AAC GAT TAA  CAGTGTCACCGTGTCACTTCAGTCAGCCATTCAATAACCTCTTACTCGTAGTGTTGCTACATCAGCACTGGGCATTCTTGGAGGATCCTGTAG  3567
1090 Phe Phe Gln Asn Lys Pro Asn Asp End

3568 AGTATTGTTAGGAGGTGAACTTCA
```

1  GGTACCGGCTAGCGTCGAACAGAGGCCCTAGGATATCGATACGTAGAGCCCAGATCTTGTGACAA  60
     +---------+---------+---------+---------+---------+---------+
     CCATGGCCGATCGCAGCTTGTCTCCGGGATCCTATAGCTATGCATCTCGGGTCTAGAACACTGTT

ValProLeuAlaSerThrGlyLyLeuGlyTyrArgTyrValGluProArgSerCysAspLys

<----- Polylinker -----|---------- Fc ----------->
```

LEUKEMIA INHIBITORY FACTOR RECEPTORS AND FUSION PROTEINS

CROSS-REFERENCE TO RELATED APPLICATION

This application is a divisional of U.S. application Ser. No. 07/943,843, filed Sep. 11, 1992, now U.S. Pat. No. 5,284,755, which is a continuation-in-part of U.S. application Ser. No. 07/670,608, filed Mar. 13, 1991, now abandoned, which is a continuation-in-part of U.S. application Ser. No. 07/626,725, filed Dec. 13, 1990, now abandoned.

BACKGROUND OF THE INVENTION

The present invention relates generally to cytokine receptors, and more specifically, to leukemia inhibitory factor receptors.

Leukemia inhibitory factor (LIF) is a polypeptide hormone which plays a central role in the regulation of diverse adult and embryonic systems. LIF acts on a variety of cell types and has multiple biological activities. The diversity in biological activity is reflected in the various synonyms of LIF, which include hepatocyte stimulating factor III (HSF III); Baumann and Wong, *J. Immunol.* 143:1163, 1989); cholinergic nerve differentiation factor (CNDF; Yamamori et al., *Science* 246:1412, 1990); melanoma-derived lipoprotein lipase inhibitor (MLPLI; Mori et al., *Biochem. Biophys Res. Comm.* 160:1085, 1989); human interleukin for DA cells (HILDA; Moreau et al., *Nature* 336:690, 1988); differentiation factor (D-factor; Tomida et al., *J. Biol. Chem.* 259:10978, 1984); differentiation inhibitory factor (DIF; Abe et at., *J. Biol. Chem.* 264:8941, 1989); differentiation inhibitory activity (DIA; Smith and Hooper, *Devel. Biol.* 121:1, 1987); and differentiation retarding factor (DRF; Koopman and Cotton, *Exp. Cell. Res.* 154:233, 1984).

The diversity of biological activities ascribed to LIF, whether differentiation inhibition or stimulation, proliferation or functional activation, is mediated by specific plasma membrane receptors which bind LIF. Despite the wide range of biological activities mediated by LIF, it is believed that LIF receptors (LIF-R) are highly conserved in a variety of species and expressed on a large variety of cells, since the ligand is highly conserved between species (Gough et al., *Proc. Natl. Acad. Sci. USA* 85:2623, 1988; Yamamori et al., *Science* 246:1412, 1990). LIF receptors have been identified by ligand affinity cross-linking techniques on various cell lines, including monocyte-macrophages (Hilton, et al., *Proc. Natl. Acad. Sci. USA* 85:5971, 1988), and also on some non-hematopoietic cells including osteoblasts, placental trophoblasts, and liver parenchymal cells (Metcalf et al., *Blood* 76:50, 1990). Such studies indicate that LIF-R has a molecular weight of 90 kDa (Jacques et al., 5th Symposium sur les Marqueurs de l'inflammation, Lyon 25-27 Sep. 1990, Abstract No. 37, page 122 (bioMerieux sa, Lyon, France). Characterization of LIF receptors by Scatchard analysis of binding isotherms has demonstrated that specific cell surface receptor molecules from a variety of target cells have approximately the same affinity for LIF (40–100 pM) and are present in low numbers (150 to 2,500 receptors per cell) on all cells types tested.

In order to study the structural and biological characteristics of LIF-R and the role played by LIF-R in the responses of various cell populations to LIF stimulation, or to use LIF-R effectively in therapy, diagnosis, or assay, homogeneous compositions are needed. Such compositions are theoretically available via purification of receptors expressed by cultured cells, or by cloning and expression of genes encoding the receptors. Prior to the present invention, however, several obstacles prevented these goals from being achieved.

First, although some cell lines have been identified which express LIF-R, such cell lines express LIF-R only in very low numbers (150 to 2,500 receptors/cell), which has impeded efforts to purify receptors in amounts sufficient for obtaining amino acid sequence information or generating monoclonal antibodies. The low numbers of receptors has also precluded any practical translation assay-based method of cloning.

Second, even if LIF-R protein compositions of sufficient purity could be obtained to permit N-terminal protein sequencing, the degeneracy of the genetic code may not permit one to define a suitable probe without considerable additional experimentation. Many iterative attempts may be required to define a probe having the requisite specificity to identify a hybridizing sequence in a cDNA library. Although direct expression cloning techniques avoid the need for repetitive screening using different probes of unknown specificity and have been useful in cloning other receptors (e.g., IL-1R), they have not been shown to be sufficiently sensitive to identify LIF-R clones from cDNA libraries derived from cells expressing low numbers of LIF-R.

Thus, efforts to purify the LIF-R or to clone or express genes encoding LIF-R have been impeded by lack of purified receptor or a suitable source of receptor mRNA.

SUMMARY OF THE INVENTION

The present invention provides purified leukemia inhibitory factor receptor (LIF-R) and isolated DNA sequences encoding LIF-R, e.g., human and murine LIF-R, and analogs thereof. Preferably, such isolated DNA sequences are selected from the group consisting of (a) DNA sequences comprising a nucleotide sequence derived from the coding region of a native LIF-R gene; (b) DNA sequences capable of hybridization to a DNA of (a) under moderately stringent conditions and which encode biologically active LIF-R; and (c) DNA sequences which are degenerate as a result of the genetic code to a DNA sequence defined in (a) or (b) and which encode biologically active LIF-R. Examples of the DNA sequences of (a) are cDNA clones comprising the coding region of the DNA sequence presented in SEQ ID NO:1 (human clone 65), SEQ ID NO:3 (murine clone 3), or SEQ ID NO:5 (composite full length human LIF-R sequence). Isolated DNA sequences of the present invention may comprise cDNA, PCR-amplified DNA, genomic DNA lacking introns, chemically synthesized DNA, or combinations thereof. The present invention also provides recombinant expression vectors comprising the DNA sequences defined above, recombinant LIF-R proteins produced using the recombinant expression vectors, and processes for producing the recombinant LIF-R proteins utilizing the expression vectors.

The present invention also provides substantially homogeneous preparations of LIF-R protein. LIF-R proteins have the sequence of amino acids shown, for example, in SEQ ID NO:2 and SEQ ID NO:6 (both human LIF-R) and SEQ ID NO:4 (murine LIF-R).

Homodimeric forms of the LIF-R proteins are also provided.

The present invention also provides compositions for use in therapy, diagnosis, assay for LIF or LIF-R, or in raising antibodies to LIF-R, comprising effective quantities of the LIF-R proteins of the present invention.

BRIEF DESCRIPTION OF THE FIGURES

These and other aspects of the present invention will become evident upon reference to the following detailed description.

FIGS. 2a through 2e present a human LIF-R DNA sequence and the amino acid sequence encoded thereby, derived by sequencing cDNA and genomic clones as described in example 4. Amino acids are numbered on the left and nucleotides on the right. The signal peptide includes amino acids −44 to −1. The transmembrane domain is heavily underlined, and potential N-linked glycosylation sites are marked with asterisks. Hallmark residues associated with the hematopoietin family of receptors are shown boxed. The horizontal arrow marks the point at which genomic sequence was used to derive the 3′ coding region of the hLIF-R. All cDNA clones terminated with a stretch of A nucleotides at this point.

FIG. 4 shows the positions of restriction endonuclease cleavage sites in the polylinker segment and 5′ end of the Fc cDNA insert in plasmid hIgG1Fc, as described in example 5.

DETAILED DESCRIPTION OF THE INVENTION

Definitions

Figure 1:
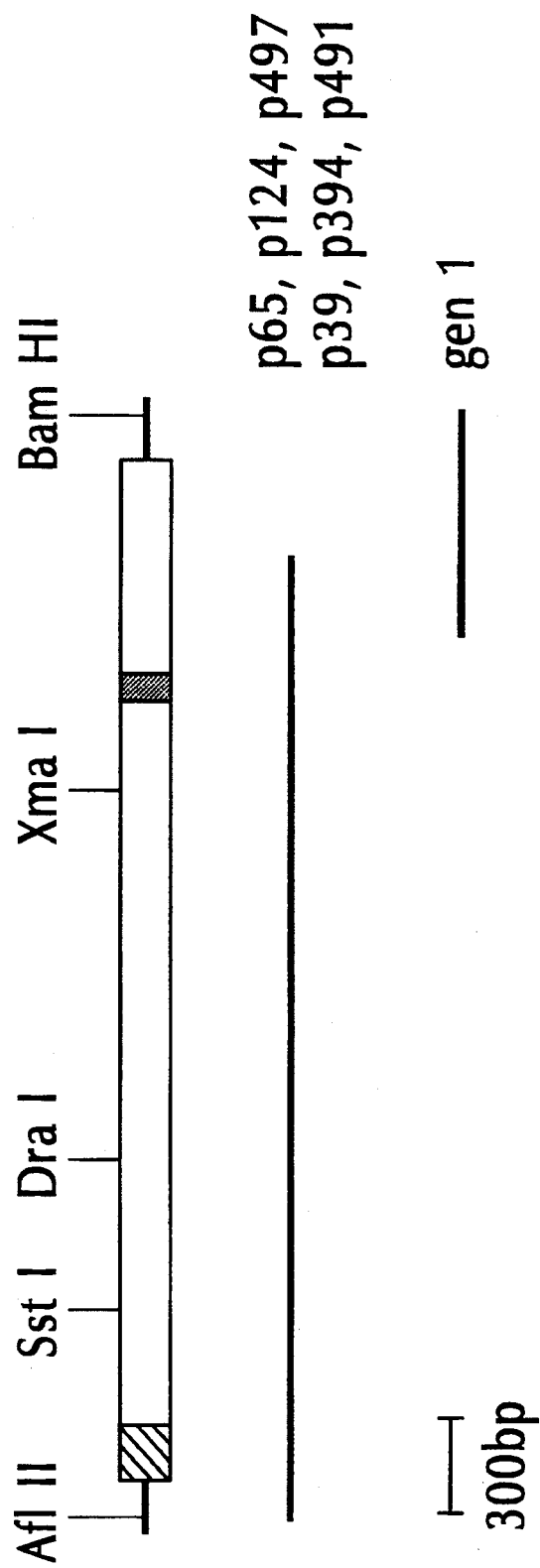
FIG. 1 presents a composite map of a human LIF-R-encoding DNA sequence, including the cleavage sites for certain restriction endonucleases. The hLIF-R open reading frame is shown boxed. The signal sequence is shown as a hatched box and the transmembrane domain is shown as a solid box. Several hLIF-R clones were isolated from cDNA and genomic libraries as described in examples 1 and 4. The horizontal lines under the composite map indicate the portion of the hLIF-R sequence that is contained in the various clones.

"Leukemia inhibitory factor receptor" and "LIF-R" refer to proteins which are present on the surface of various hematopoietic cells including monocyte-macrophages and megakaryocytes, and on non-hematopoietic cells, including osteoblasts, placental trophoblasts, and liver parenchymal cells, and which are capable of binding leukemia inhibitory factor (LIF) molecules and, in their native configuration as mammalian plasma membrane proteins, play a role in transducing the signal provided by LIF to a cell. The mature full-length human LIF-R has been previously described as a protein having a molecular weight of approximately 90 kDa; however, the molecular weight of the human LIF-R protein disclosed herein, and shown in SEQ ID NO:2, is about 190,000 kDa. As used herein, the above terms include analogs or fragments of native LIF-R proteins with LIF-binding or signal transducing activity. Specifically included are truncated, soluble or fusion forms of LIF-R protein as defined below. In the absence of any species designation, LIF-R refers generically to mammalian LIF-R, which includes, but is not limited to, human, murine, and bovine LIF-R. Similarly, in the absence of any specific designation for deletion mutants, the term LIF-R means all forms of LIF-R, including mutants and analogs which possess LIF-R biological activity.

"Soluble LIF-R" or "sLIF-R" as used in the context of the present invention refer to proteins, or substantially equivalent analogs, which are substantially similar to all or part of the extracellular region of a native LIF-R, and are secreted by the cell but retain the ability to bind LIF or inhibit LIF signal transduction activity via cell surface bound LIF-R proteins. Soluble LIF-R proteins may also include pan of the transmembrane region or part of the cytoplasmic domain or other sequences, provided that the soluble LIF-R protein is capable of being secreted from the cell. Inhibition of LIF signal transduction activity can be determined using primary cells or cells lines which express an endogenous LIF-R and which are biologically responsive to LIF or which, when transfected with recombinant LIF-R DNAs, are biologically responsive to LIF. The cells are then contacted with LIF and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et al., *J. Exp. Med.* 171:861 (1990); Curtis et al., *Proc. Natl. Acad. Sci. USA* 86:3045 (1989); Prywes et al., *EMBO J.* 5:2179 (1986) and Chou et al., *J. Biol. Chem.* 262:1842 (1987).

The term "isolated" or "purified", as used in the context of this specification to define the purity of LIF-R protein or protein compositions, means that the protein or protein composition is substantially free of other proteins of natural or endogenous origin and contains less than about 1% by mass of protein contaminants residual of production processes. Such compositions, however, can contain other proteins added as stabilizers, carriers, excipients or co-therapeutics. LIF-R is purified to substantial homogeneity if it is detectable as a single protein band in a polyacrylamide gel by silver staining.

The term "substantially similar," when used to define either amino acid or nucleic acid sequences, means that a particular subject sequence, for example, a mutant sequence, varies from a reference sequence (e.g., a native sequence) by one or more substitutions, deletions, or additions, the net effect of which is to retain biological activity of the LIF-R protein as may be determined, for example, in LIF-R binding assays, such as is described in Example 1 below. In one embodiment of the invention, such a mutant amino acid sequence is at least 90% identical, preferably at least 95% identical, to the amino acid sequence of a native LIF-R protein (e.g., the native sequence presented in SEQ ID NOS: 2, 4 or 6). In other words, at least 90% of the amino acids of a native LIF-R sequence are present, and in the same order, in the mutant sequence. For fragments of LIF-R proteins (e.g., soluble LIF-R polypeptides), the term "at least 90% identical" refers to that portion of the reference native sequence that is found in the LIF-R fragment.

Computer programs are available for determining the percent identity between two DNA or amino acid sequences (e.g., between a mutant sequence and a native sequence). One example is the GAP computer program, version 6.0, described by Devereux et al. (*Nucl. Acids*

Res. 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981).

Alternatively, nucleic acid subunits and analogs are "substantially similar" to the specific native DNA sequences disclosed herein (e.g., the sequences of SEQ ID NOS: 1, 3, or 5) if the DNA sequence is capable of hybridization to a native LIF-R DNA sequence under moderately stringent conditions (50° C., 2×SSC) and encodes biologically active LIF-R protein; or the DNA sequence is degenerate as a result of the genetic code to one of the foregoing native or hybridizing DNA sequences and encodes a biologically active LIF-R protein. DNA sequences that hybridize to a native LIF-R DNA sequence under conditions of severe stringency, and which encode biologically active LIF-R, are also encompassed by the present invention. Moderate and severe stringency hybridization conditions are terms understood by the skilled artisan and have been described in, for example, Sambrook et al. *Molecular Cloning: A Laboratory Manual,* 2 ed. Vol. 1, pp. 1.101–104, Cold Spring Harbor Laboratory Press, (1989). LIF-R proteins encoded by the foregoing DNA sequences are provided by the present invention.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., *E. coli*, will be free of glycan; protein expressed in yeast may have a glycosylation pattern different from that expressed in mammalian cells.

"Biologically active," as used throughout the specification as a characteristic of LIF-R, means either that a particular molecule shares sufficient amino acid sequence similarity with a native LIF-R protein to be capable of binding detectable quantities of LIF, preferably at least 0.01 nmoles LIF per nanomole LIF-R, or, in the alternative, shares sufficient amino acid sequence similarity to be capable of transmitting an LIF stimulus to a cell, for example, as a component of a hybrid receptor construct. More preferably, biologically active LIF-R within the scope of the present invention is capable of binding greater than 0.1 nanomoles LIF per nanomole receptor, and most preferably, greater than 0.5 nanomoles LIF per nanomole receptor.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention may be assembled from cDNA fragments and short oligonucleotide linkers, or from a series of oligonucleotides, to provide a synthetic gene which is capable of being expressed in a recombinant transcriptional unit.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as *E. coli* or yeast such as *S. cerevisiae,* which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Isolation of DNA Encoding LIF-R

A human DNA sequence encoding human LIF-R was isolated from a cDNA library prepared using standard methods by reverse transcription of polyadenylated RNA isolated from human placental cells. Transfectants expressing biologically active LIF-R were initially identified using a modified slide autoradiographic technique, substantially as described by Gearing et al., *EMBO J.* 8:3667, 1989. Briefly, COS-7 cells were transfected with miniprep DNA in pDC303 from pools of cDNA clones directly on glass slides and cultured for 2–3 days to permit transient expression of LIF-R. The slides containing the transfected cells were then incubated with medium containing $^{125}$I-LIF, washed to remove unbound labeled LIF, fixed with glutaraldehyde, and dipped in liquid photographic emulsion and exposed in the dark. After developing the slides, they were individually examined with a microscope and positive cells expressing LIF-R were identified by the presence of autoradiographic silver grains against a light background.

Using this approach, approximately 240,000 cDNAs were screened in pools of approximately 2,400 cDNAs using the slide autoradiographic method until assay of one transfectant pool showed multiple cells clearly positive for LIF binding. This pool was then partitioned into pools of 600 and again screened by slide autoradiography and a positive pool was identified. This pool was further partitioned into pools of 60 and screened by plate binding assays analyzed by quantitation of bound $^{125}$I-LIF. The cells were scraped off and counted to determine which pool of 60 was positive. Individual colonies from this pool of 60 were screened until a single clone (clone 65) was identified which directed synthesis of a surface protein with detectable LIF binding activity. This clone was isolated, and its insert is sequenced to determine the sequence of the human LIF-R cDNA clone 65. The cloning vector pDC303 which contains the human LIF-R cDNA clone 65 was deposited with the American Type Culture Collection, Rockville, Md., USA (ATCC) on Dec. 11, 1990, under the name pHLIFR-65 (ATCC Accession No. 68491). The deposit was made under the conditions of the Budapest Treaty.

A probe may be constructed from the human sequence and used to screen various other mammalian cDNA libraries. cDNA clones which hybridize to the human probe are then isolated and sequenced.

A murine LIF-R cDNA clone was isolated by cross-species hybridization to a probe derived from human clone 65. The murine clone encoded a LIF-R protein that lacked a transmembrane region and thus was secreted rather than being retained on the cell membrane. Isolation of this murine clone is described in Example 2. Probes derived from this clone may be used in screening murine cDNA or genomic libraries to identify additional murine LIF-R clones.

A probe derived from the human clone 65 was also used in screening human cDNA and genomic libraries to identify additional human LIF-R clones. The DNA sequence presented in SEQ ID NO:5 was derived by sequencing and alignment of these human clones, as described in Example 4.

Like most mammalian genes, mammalian LIF-R is presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Proteins and Analogs

The present invention provides purified mammalian LIF-R polypeptides, both recombinant and non-recombinant (the latter being purified from naturally-occurring cellular sources). Isolated LIF-R polypeptides of this invention are substantially free of other contaminating materials of natural or endogenous origin and contain less than about 1% by mass of protein contaminants residual of production processes. The LIF-R polypeptides of this invention are optionally without associated native-pattern glycosylation.

Mammalian LIF-R of the present invention includes, by way of example, primate, human, murine, canine, feline, bovine, ovine, equine, caprine and porcine LIF-R. Mammalian LIF-R can be obtained by cross species hybridization, for example using a single stranded cDNA derived from the human LIF-R DNA sequence, clone 65, as a hybridization probe to isolate LIF-R cDNAs from mammalian cDNA libraries.

Derivatives of LIF-R within the scope of the invention also include various structural forms of the primary protein which retain biological activity. Due to the presence of ionizable amino and carboxyl groups, for example, a LIF-R protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence murals. Covalent derivatives are prepared by linking particular functional groups to LIF-R amino acid side chains or at the N- or C-termini. Other derivatives of LIF-R within the scope of this invention include covalent or aggregative conjugates of LIF-R or its fragments with other proteins or polypeptides, such as by synthesis in recombinant culture as N-terminal or C-terminal fusions. For example, the conjugated peptide may be a a signal (or leader) polypeptide sequence at the N-terminal region of the protein which co-translationally or post-translationally directs transfer of the protein from its site of synthesis to its site of function inside or outside of the cell membrane or wall (e.g., the yeast or-factor leader). LIF-R protein fusions can comprise peptides added to facilitate purification or identification of LIF-R (e.g., poly-His). The amino acid sequence of LIF-R can also be linked to the peptide Asp-Tyr-Lys-Asp-Asp-Asp-Asp-Lys (DYKDDDDK) (Hopp et al., *Bio/Technology* 6:1204,1988 and U.S. Pat. No. 5,011,912.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*.

LIF-R derivatives may also be used as immunogens, reagents in receptor-based immunoassays, or as binding agents for affinity purification procedures of LIF or other binding ligands. LIF-R derivatives may also be obtained by cross-linking agents, such as M-maleimidobenzoyl succinimide ester and N-hydroxysuccinimide, at cysteine and lysine residues. LIF-R proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, LIF-R may be used to selectively bind (for purposes of assay or purification) anti-LIF-R antibodies or LIF.

The LIF-R proteins of the present invention encompass proteins having amino acid sequences that vary from those of native LIF-R proteins, but that retain the ability to bind LIF or transduce a LIF-induced signal. Such variant proteins comprise one or more additions, deletions, or substitutions of amino acids when compared to a native sequence, but exhibit biological activity that is essentially equivalent to that of a native LIF-R protein. Likewise, the LIF-R-encoding DNA sequences of the present invention encompass sequences that comprise one or more additions, deletions, or substitutions of nucleotides when compared to a native LIF-R DNA sequence, but that encode a LIF-R protein that is essentially bioequivalent to a native LIF-R protein. Examples of such variant amino acid and DNA sequences (the "substantially similar" sequences discussed above) include, but are not limited to, the following.

Bioequivalent analogs of LIF-R proteins may be constructed by, for example, making various substitutions of residues or sequences or deleting terminal or internal residues or sequences not needed for biological activity. Bioequivalent analogs may be identified using the assays for biological activity that are described herein (e.g., in example 1). For example, cysteine residues not essential for biological activity can be deleted or replaced with other amino acids to prevent formation of unnecessary or incorrect intramolecular disulfide bridges upon renaturation. One or more of the cysteines that are not conserved in the hematopoietin receptor family (as indicated in FIGS. 2a through 2e) may be deleted or replaced, for example. Alternative embodiments (when the LIF-binding property of the LIF-R is desired but signal transduction is not necessary) include LIF-Rs in which the cysteines of the extracellular domain remain but cysteines of the cytoplasmic domain are deleted or replaced.

Another embodiment of the present invention involves modification of adjacent dibasic amino acid residues to enhance expression of LIF-R in yeast systems in which KEX2 protease activity is present. Site-specific mutagenesis procedures can be employed to inactivate KEX2 protease processing sites by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The resulting muteins are less susceptible to cleavage by the KEX2 protease at locations other than the yeast α-factor leader sequence, where cleavage upon secretion is intended. EP 212,914, is among the references disclosing the use of site-specific mutagenesis to inactivate KEX2 protease processing sites in a protein.

Review of the human LIF-R sequence of FIGS. 2a through 2e reveals Arg-Arg, Arg-Lys, or Lys-Arg doublets at amino acids −36 and −35; −27 and −26; 134 and 135; 339 and 340; 631 and 632; 816 and 817; and 817 and 818. From one to all of these KEX2 protease processing sites may be inactivated.

The present invention includes LIF-R with or without associated native-pattern glycosylation. LIF-R expressed in yeast or mammalian expression systems, e.g., COS-7 cells, may be similar or slightly different in molecular weight and glycosylation pattern than the native molecules, depending upon the expression system. Expression of LIF-R DNAs in bacteria such as E. coli provides non-glycosylated molecules. Functional mutant analogs of mammalian LIF-R having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such sites can be eliminated by substituting another amino acid for Asn or for residue Z, deleting Asn or Z, or inserting a non-Z amino acid between $A_1$ and Z, or an amino acid other than Asn between Asn and $A_1$.

Known procedures for inactivating N-glycosylation sites in proteins include those described in U.S. Pat. No. 5,071,972 and EP 276,846. N-glycosylation sites in human LIF-R are indicated by asterisks in FIGS. 2a through 2e. From one to all of these sites may be inactivated. In one embodiment of the invention, if reduction but not elimination of glycosylation is desired, the first (i.e., N-terminal) five N-glycosylation sites of human LIF-R are inactivated. Review of the murine LIF-R amino acid sequence of SEQ ID NO:4 reveals that the murine protein lacks these five N-glycosylation sites (located in the fast hematopoietin domain), indicating that these sites may be deleted from the human protein as well without eliminating the protein's LIF-binding property.

Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian LIF-Rs is suggestive of additional conservative substitutions that may be made without altering the essential biological characteristics of LIF-R.

Subunits (fragments) of LIF-R may be constructed by deleting terminal or internal residues or sequences. LIF-R fragments encompassed by the present invention include, but are not limited to, the following. Additional biologically active LIF-R fragments may be identified using assays such as those described in example 1. One example of an LIF-R fragment comprises amino acids 1 to 945 of SEQ ID NO: 1. As described in example 4, amino acid 945 is the last amino acid of the polypeptide encoded by clone pHLIF-R-65, before the poly-A nucleotide segment believed to result from oligo(dT) priming at an internal site in the mRNA during preparation of the hLIF-R cDNA.

LIF-binding activity resides in the extracellular domain. Thus, for applications requiring LIF-binding activity (but not the signal transducing activity conferred by the cytoplasmic domain), useful LIF-R proteins include those lacking all or part of the transmembrane region or the cytoplasmic domain of the protein. Human LIF-R fragments thus include those containing amino acids −44-x or, when the signal sequence is not desired, amino acids 1-x of the full length LIF-R sequence depicted in SEQ ID NO:5, wherein x represents an integer from 789 to 1052. Amino acid number 789 is the last amino acid of the extracellular domain (i.e., before the start of the transmembrane region). Polypeptides terminating in amino acid number 1052 lack the last C-terminal amino acid of the full length protein. The desirability of including the signal sequence depends on such factors as the position of LIF-R when it is a component of a fusion protein, and the intended host cells when the receptor is to be produced via recombinant DNA technology. Other LIF-R polypeptides may be chosen with regard to sequences that are conserved in the hematopoietin receptor family, (i.e., chosen to include the boxed sequence(s) shown in FIGS. 2a through 2e).

In one embodiment of the present invention, the LIF-R fragment is a soluble LIF-R polypeptide in which the transmembrane region and intracellular (cytoplasmic) domain of LIF-R are deleted or substituted with hydrophilic residues to facilitate secretion of the receptor into the cell culture medium. Soluble LIF-R proteins may also include part of the transmembrane region, provided that the soluble LIF-R protein is capable of being secreted from the cell. The resulting protein is referred to as a soluble LIF-R molecule which retains its ability to bind LIF. The present invention contemplates such soluble LIF-R constructs corresponding to all or part of the extracellular region of LIF-R. The resulting soluble LIF-R constructs are then inserted and expressed in appropriate expression vectors and assayed for the ability to bind LIF, as described in Example 1. Biologically active soluble LIF-Rs resulting from such constructions are also contemplated to be within the scope of the present invention.

Examples of soluble LIF-R proteins include, but are not limited to, the following. One soluble human LIF-R polypeptide comprises the entire extracellular domain, i.e. amino acids 1–789 of SEQ ID NO:2. Other soluble LIF-Rs are truncated upstream of the transmembrane region, but preferably include that portion of the protein that contains the residues conserved among the members of the hematopoietin receptor family (shown boxed in FIGS. 2a through 2e), i.e., amino acids 11–479 of SEQ ID NO:2. The N-terminus of such soluble LIF-Rs is any of amino acids 1–11, and the protein extends to a C-terminus selected from any of amino acids 479 through 789. Two such soluble proteins comprise amino acids 1–702 or 1–775 of SEQ ID NO:1. Constructs encoding these proteins may be prepared by techniques that involve cleaving the human LIF-R cDNA of clone 65 (example 1) with the restriction endonucleases Asp718 and Xmn1 or with Asp718 and Bsp1286I. Asp718 cleaves the vector upstream of the inserted LIF-R-encoding cDNA. Xmn1 cleaves within the codon for Asp at position 702 and Bsp1286I cleaves just 3' of the codon for Val at position 775. If desired, an oligonucleotide may be ligated to the 3' end of the Asp718/Bsp1286I fragment to extend the LIF-R sequence, e.g., through amino acid number 789.

Other soluble human LIF-Rs comprise amino acids 1–678 or 1–680. When the human and murine LIF-R amino acid sequences disclosed herein are aligned (with gaps introduced to maximize identity between the two sequences), amino acid 680 of the human sequence is aligned with the last amino acid of the murine protein, and amino acid 678 is the last amino acid of the human sequence that is identical to a corresponding amino acid in the murine sequence. Since the murine protein binds LIF, the murine LIF-R contains that portion of the protein required for LIF binding.

The murine cDNA isolated in example 2 encodes a naturally occurring soluble LIF-R protein. DNA sequences encoding soluble human LIF-R proteins may be derived from the isolated cDNA encoding membrane-bound human LIF-R (described in example 1) by conventional procedures, in view of the sequence information presented in SEQ ID NO:1. Among the procedures that may be employed to isolate and amplify a DNA fragment encoding truncated LIF-R is the well known polymerase chain reaction (PCR) procedure. See *Recombinant DNA Methodology*, Wu et al. eds., Academic Press Inc., San Diego (1989), pp 189–196. Alternative procedures include restriction endonuclease digestion of cloned LIF-R DNA, isolation of the desired fragment by gel electrophoresis, and subcloning of the fragment into an expression vector using conventional procedures. Oligonucleotides may be ligated to an isolated DNA fragment to regenerate the 5' or 3' terminus to a desired point in the sequence. The sequence of such oligonucleotides, as well as the primers employed in PCR, may be based upon the DNA sequence presented in SEQ ID NO: 1.

The N- or C-terminus of the LIF-R proteins of the present invention may vary according to such factors as the type of host cells employed when producing the protein via recombinant DNA technology and the particular cells from which the protein is purified when non-recombinant LIF-R is employed. Such variations may be attributable to differential post-translational processing of the protein in various types of cells, for example. Variations in the N- or C-terminal sequence also may result from the oligonucleotides chosen to reconstruct either terminus of the LIF-R encoding DNA sequence when constructing expression vectors.

Differential processing may result in mature LIF-R proteins having an N-terminal amino acid other than those shown at position 1 of SEQ ID NOS:2, 4, and 6. For example, in certain host cells, post-translational processing will remove the methionine residue encoded by an initiation codon, whereas the methionine residue will remain at the N-terminus of proteins produced in other types of host cells. Further, the N- and C-termini have been known to vary for the same protein, depending on the source of the protein. In some cases, the deletion of amino acids at either terminus of the protein may be due to proteolysis, occurring either intracellularly or during purification. Varying N-termini may also result from cleavage of the signal peptide in certain host cells at a point other than between amino acids −1 and 1 of the disclosed sequences.

The LIF-R proteins of the present invention thus include proteins having termini that vary from those shown in SEQ ID NOS:2 and 6 (human) or 4 (murine). The N-terminal amino acid of the mature protein may, for example, be any of the amino acids at positions 1 to 5 of SEQ ID NOS:2, 4, or 6. The C-terminus may be truncated deliberately during expression vector construction (e.g., in constructing vectors encoding soluble proteins as described above) or as a result of differential processing which may remove up to about five C-terminal amino acids, for example.

Mutations in nucleotide sequences constructed for expression of the above-described variant or analog LIF-R proteins should, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed LIF-R mutants screened for the desired activity.

Not all mutations in the nucleotide sequence which encodes LIF-R will be expressed in the final product. For example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression (see U.S. Pat. No. 4,425,437, column 6). The known degeneracy of the genetic code permits variation of a DNA sequence without altering the amino acid sequence, since a given amino acid may be encoded by more than one codon.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

The LIF-R proteins of the present invention encompass proteins encoded by (a) a DNA sequence derived from the coding region of a native LIF-R gene or (b) a DNA sequence capable of hybridization to a native LIF-R DNA of (a) under moderately stringent conditions and which encodes biologically active LIF-R. LIF-R proteins encoded by a DNA molecule that varies from the DNA sequences of SEQ ID NOS: 1, 3, and 5, wherein one strand of the DNA molecule will hybridize to the DNA sequence presented in SEQ ID NOS: 1, 3, or 5, include, but are not limited to, LIF-R fragments (soluble or membrane-bound) and LIF-R proteins comprising inactivated N-glycosylation site(s), inactivated KEX2 protease processing site(s), and/or conservative amino acid substitution(s), as described above. LIF-R proteins encoded by DNA derived from other mammalian species, wherein the DNA will hybridize to the human or murine DNA of SEQ ID NOS: 1, 3, or 5, are also encompassed.

Both monovalent forms and polyvalent forms of LIF-R are useful in the compositions and methods of this invention. Polyvalent forms possess multiple LIF-R binding sites for LIF ligand. For example, a bivalent soluble LIF-R may consist of two tandem repeats of the extracellular region of LIF-R, separated by a linker region. Two LIF-R polypeptides (each capable of binding LIF) may be joined via any suitable means, e.g., using one of the commercially available cross-linking reagents used to attach one polypeptide to another (Pierce Chemical Co., Rockford, Ill.). Alternatively, a fusion protein comprising multiple LIF-R polypeptides joined via peptide linkers may be produced using recombinant DNA technology. Suitable peptide linkers comprise a chain of amino acids, preferably from 20 to 100 amino acids in length. The linker advantageously comprises amino acids selected from the group consisting of glycine, asparagine, serine, threonine, and alanine. Examples of suitable peptide linkers include, but are not limited to, $(Gly_4Ser)_n$, wherein n is 4-12, and $(Gly_4SerGly_5Ser)_2$. The use of such peptide linkers is illustrated in U.S. Pat. No. 5,073,627, for example.

A DNA sequence encoding a desired peptide linker may be inserted between, and in the same reading frame as, two DNA sequences encoding LIF-R using any suitable conventional technique. For example, a chemically synthesized oligonucleotide encoding the linker and containing appropriate restriction endonuclease cleavage sites may be ligated between two LIF-R encoding sequences. The resulting gene fusion is inserted into an expression vector for production of the fusion protein in the desired host cells.

Alternate polyvalent forms may also be constructed, for example, by chemically coupling LIF-R to any clinically acceptable carrier molecule, a polymer selected from the group consisting of Ficoll, polyethylene glycol or dextran using conventional coupling techniques. Alternatively, LIF-R may be chemically coupled to biotin, and the biotin-LIF-R conjugate then allowed to bind to avidin, resulting in tetravalent avidin/biotin/LIF-R molecules. LIF-R may also be covalently coupled to dinitrophenol (DNP) or trinitrophenol (TNP) and the resulting conjugate precipitated with anti-DNP or anti-TNP-IgM, to form decameric conjugates with a valency of 10 for LIF-R binding sites.

A recombinant chimeric antibody molecule may also be produced having LIF-R sequences substituted for the variable domains of either or both of the immunoglobulin molecule heavy and light chains and having unmodified constant region domains. For example, chimeric LIF-R/IgG$_1$ may be produced from two chimeric genes—a LIF-R/human k light chain chimera (LIF-R/$C_k$) and a LIF-R/human g1 heavy chain chimera (LIF-R/$C_{g-1}$). Following transcription and translation of the two chimeric genes, the gene products assemble into a single chimeric antibody molecule having LIF-R displayed bivalently. Assembly of two sets of the two chimeric proteins results in a molecule comprising two LIF-R/light chain fusions and two LIF-R/heavy chain fusions. LIF-R is displayed tetravalently. Assembly occurs when disulfide bonds form between the polypeptide chains, as occurs in native antibodies. Such polyvalent forms of LIF-R may have enhanced binding affinity for LIF ligand. Additional details relating to the construction of such chimeric antibody molecules are disclosed in WO 89/09622 and EP 315062.

Alternatively, a LIF-R DNA sequence may be fused to a DNA sequence encoding an antibody Fc region polypeptide. Dimeric forms of LIF-R include homodimers comprising two LIF-R/Fc fusion proteins joined by disulfide bonds between the Fc moieties. Such homodimers preferably comprise one of the soluble LIF-R polypeptides described above, with an antibody Fc region polypeptide attached to the C-terminus of the LIF-R polypeptide. The LIF-R/Fc fusion proteins optionally comprise a peptide linker (described above) positioned between the LIF-R polypeptide and the antibody Fc polypeptide. One peptide linker is described in example 5.

By "antibody Fc region polypeptides" is meant polypeptides corresponding to the Fc region of an antibody, or fragments thereof comprising sufficient cysteine residues so that disulfide bonds will form between two Fc polypeptides. N-terminal fragments of an antibody Fc region that contain the cysteine residues involved in disulfide bond formation at the hinge region may be employed. Examples include the Fc polypeptide described in example 5 and fragments thereof comprising at least the first three cysteine residues (hinge region). Procedures for isolating the Fc region of an antibody are well-known and include proteolytic digestion with papain. Alternatively, an Fc polypeptide may be produced by recombinant cells or chemically synthesized.

In one embodiment, the present invention provides an isolated DNA sequence encoding a soluble fusion protein comprising an N-terminal signal peptide followed by a human LIF-R polypeptide (derived from the extracellular domain), which is followed by an antibody Fc polypeptide. The signal sequence may be the native human LIF-R signal peptide (amino acids −44 to −1 of SEQ ID NO: 1) or a heterologous signal peptide, chosen according to the host cells to be employed. Heterologous signal peptides include the yeast α factor leader peptide described below and the IL-7 leader peptide described in U.S. Pat. No. 4,965,195, for example.

Figure 3:
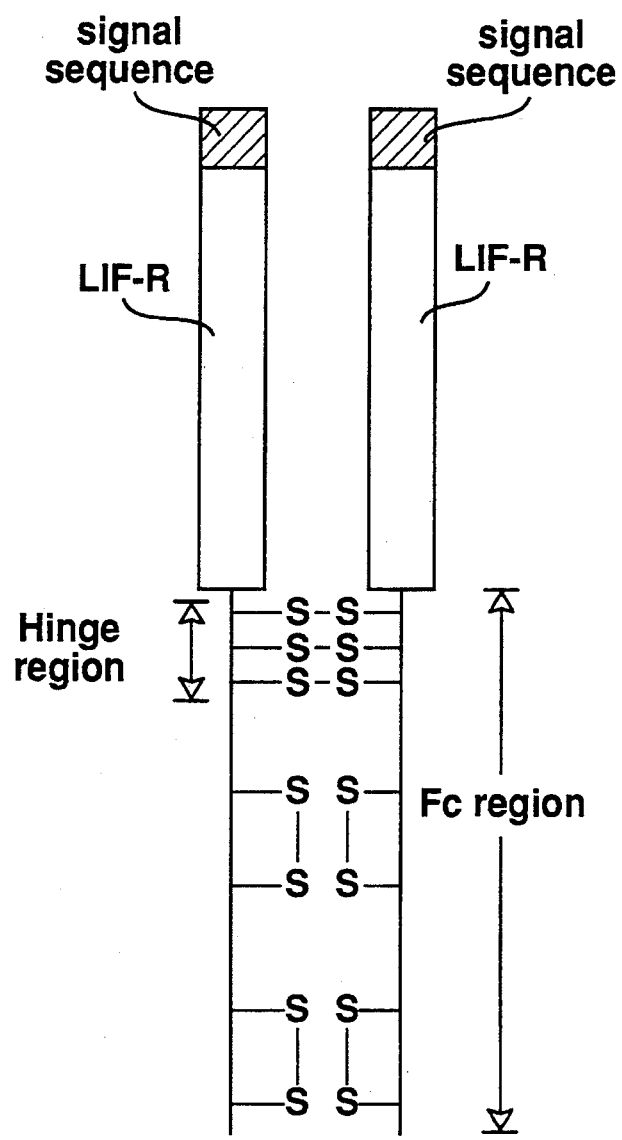
FIG. 3 is a schematic representation of a human LIF-R homodimer. The homodimeric receptor comprises two soluble human LIF-R/Fc fusion proteins joined by disulfide bonds between the Fc moieties.

One example of a dimeric receptor comprising two LIF-R/Fc polypeptides is illustrated in example 5 below. The receptor is depicted in FIG. 3. The number and position of disulfide bonds may vary from those shown in FIG. 3.

Expression Of Recombinant LIF-R

The present invention provides recombinant expression vectors to amplify or express DNA encoding LIF-R. Recombinant expression vectors are replicable DNA constructs which have synthetic or cDNA-derived DNA fragments encoding mammalian LIF-R or bioequivalent analogs operably linked to suitable transcriptional or translational regulatory elements derived from mammalian, microbial, vital or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements may include an operator sequence to control transcription, a sequence encoding suitable mRNA ribosomal binding sites. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

DNA sequences encoding mammalian LIF-Rs which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence. Other embodiments include sequences capable of hybridizing to clone 65 under moderately stringent conditions (50° C., 2×SSC) and other sequences hybridizing or degenerate to those which encode biologically active LIF-R polypeptides.

Recombinant LIF-R DNA is expressed or amplified in a recombinant expression system comprising a substantially homogeneous monoculture of suitable host microorganisms, for example, bacteria such as *E. coli* or yeast such as *S. cerevisiae*, which have stably integrated (by transformation or transfection) a recombinant transcriptional unit into chromosomal DNA or carry the recombinant transcriptional unit as a component of a resident plasmid. Mammalian host cells are preferred for expressing recombinant LIF-R. Generally, cells constituting the system are the progeny of a single ancestral transformant. Recombinant expression systems as defined herein will express heterologous protein upon induction of the regulatory elements linked to the DNA sequence or synthetic gene to be expressed.

Transformed host cells are cells which have been transformed or transfected with LIF-R vectors constructed using recombinant DNA techniques. Transformed host cells ordinarily express LIF-R, but host cells transformed for purposes of cloning or amplifying LIF-R DNA do not need to express LIF-R. Expressed LIF-R will be deposited in the cell membrane or secreted into the culture supernatant, depending on the LIF-R DNA selected. Suitable host cells for expression of mammalian LIF-R include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce mammalian LIF-R using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, New York, 1985), the relevant disclosure of which is hereby incorporated by reference.

Prokaryotic expression hosts may be used for expression of LIF-R that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 and pGEX (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the b-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage 1 PL promoter and cI857lts thermolabile repressor. Plasmid vectors available from the American Type Culture Collection which incorporate derivatives of the $1P_L$ promoter include plasmid pHUB2, resident in *E. coli* strain JMB9 (ATCC 37092) and pPLc28, resident in *E. coli* RR1 (ATCC 53082).

Recombinant LIF-R proteins may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2m yeast plasmid or an autonomously replicating sequence (ARS), promoter, DNA encoding LIF-R, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* TRP1 or URA3 gene, which provides a selection marker for a mutant strain of yeast lacking the ability to grow in tryptophan, and a promoter derived from a highly expressed yeast gene to induce transcription of a structural sequence downstream. The presence of the TRP1 or URA3 lesion in the yeast host cell genome then provides an effective environment for detecting transformation by growth in the absence of tryptophan or uracil.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pUC18 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 8:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil or URA+ transformants in medium consisting of 0.67% YNB, with amino acids and bases as described by Sherman et al., *Laboratory Course Manual for Methods in Yeast Genetics*, Cold Spring Harbor Laboratory, Cold Spring Harbor, N.Y., 1986.

Host strains transformed by vectors comprising the ADH2 promoter may be grown for expression in a rich medium consisting of 1% yeast extract, 2% peptone, and 1% or 4% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express recombinant protein. Expression of recombinant proteins in mammalian cells is particularly preferred because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing a heterologous gene in an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The transcriptional and translational control sequences in expression vectors to be used in transforming vertebrate cells may be provided by vital sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the Bgl1 site located in the viral origin of replication is included. Further, mammalian genomic LIF-R promoter, control and/or signal sequences may be utilized, provided such control sequences are compatible with the host cell chosen. Additional details regarding the use of a mammalian high expression vector to produce a recombinant mammalian LIF-R are provided in Example 1 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

In preferred aspects of the present invention, recombinant expression vectors comprising LIF-R cDNAs are stably integrated into a host cell's DNA. Elevated levels of expression product is achieved by selecting for cell lines having amplified numbers of vector DNA. Cell lines having amplified numbers of vector DNA are selected, for example, by transforming a host cell with a vector comprising a DNA sequence which encodes an enzyme which is inhibited by a known drug. The vector may also comprise a DNA sequence which encodes a desired protein. Alternatively, the host cell may be co-transformed with a second vector which comprises the DNA sequence which encodes the desired protein. The transformed or co-transformed host cells are then cultured in increasing concentrations of the known drug, thereby selecting for drug-resistant cells. Such drug-resistant cells survive in increased concentrations of the toxic drug by over-production of the enzyme which is inhibited by the drug, frequently as a result of amplification of the gene encoding the enzyme. Where drug resistance is caused by an increase in the copy number of the vector DNA encoding the inhibitable enzyme, there is a concomitant co-amplification of the vector DNA encoding the desired protein (e.g., LIF-R) in the host cell's DNA.

A preferred system for such co-amplification uses the gene for dihydrofolate reductase (DHFR), which can be inhibited by the drug methotrexate (MTX). To achieve co-amplification, a host cell which lacks an active gene encoding DHFR is either transformed with a vector which comprises DNA sequence encoding DHFR and a desired protein, or is co-transformed with a vector comprising a DNA sequence encoding DHFR and a vector comprising a DNA sequence encoding the desired protein. The transformed or co-transformed host cells are cultured in media containing increasing levels of MTX, and those cells lines which survive are selected.

A particularly preferred co-amplification system uses the gene for glutamine synthetase (GS), which is responsible for the synthesis of glutamine from glutamate and ammonia using the hydrolysis of ATP to ADP and phosphate to drive the reaction. GS is subject to inhibition by a variety of inhibitors, for example methionine sulphoximine (MSX). Thus, LIF-R can be expressed in high concentrations by co-amplifying cells transformed with a vector comprising the DNA sequence for GS and a desired protein, or co-transformed with a vector comprising a DNA sequence encoding GS and a vector comprising a DNA sequence encoding the desired protein, culturing the host cells in media containing increasing levels of MSX and selecting for surviving cells. The GS co-amplification system, appropriate recombinant expression vectors and cells lines, are described in the following PCT applications: WO 87/04462, WO 89/01036, WO 89/10404 and WO 86/05807.

Recombinant proteins are preferably expressed by co-amplification of DHFR or GS in a mammalian host cell, such as Chinese Hamster Ovary (CHO) cells, or alternatively in a murine myeloma cell line, such as SP2/0-Ag14 or NS0 or a rat myeloma cell line, such as YB2/3.0-Ag20, disclosed in PCT applications WO/89/10404 and WO 86/05807.

Vectors derived from retroviruses may be employed in mammalian host cells. A preferred retroviral expression vector is tgLS(+) HyTK, described in PCT application WO 92/08796.

A preferred eukaryotic vector for expression of LIF-R DNA is disclosed below in Example 1. This vector, referred to as pDC303, was derived from the mammalian high expression vector pDC201 and contains regulatory sequences from SV40, CMV and adenovirus.

In an especially preferred expression system, a LIF-R-encoding DNA sequence is inserted into the mammalian expression vector pCAV-DHFR. The resulting recombinant expression vector is transfected into a DHFR⁻ Chinese hamster ovary cell line, e.g., CHO-DXB11. pCAV-DHFR is an expression vector containing SV40 promoter sequences upstream of a multiple cloning site and a dihydrofolate reductase (DHFR) gene as a selectable marker. The DHFR gene confers a selective advantage on otherwise DHFR⁻ mammalian cells that have taken up the vector, when grown in the presence of methotrexate (MTX).

pCAV/DHFR was prepared by inserting a DHFR gene into the plasmid vector known as pCAV/NOT (described in PCT application WO 90/05183). pCAV/NOT was assembled from pDC201 (a derivative of pMLSV, previously described by Cosman et al., *Nature* 312:768, 1984), SV40 and cytomegalovirus DNA and comprises, in sequence with the direction of transcription from the origin of replication: (1) SV40 sequences from coordinates 5171–270 including the origin of replication, enhancer sequences and early and late promoters; (2) cytomegalovirus sequences including the promoter and enhancer regions (nucleotides 67 1 to +63 from the sequence published by Boechart et at. (*Cell* 41:521, 1985); (3) adenovirus-2 sequences containing the first exon and part of the intron between the first and second exons of the tripartite leader, the second exon and part of the third exon of the tripartite leader and a multiple cloning site (MCS) containing sites for Xho1, Kpn1, Sma1, Not1 and Bgl1; (4) SV40 sequences from coordinates 4127–4100 and 2770–2533 that include the polyadenylation and termination signals for early transcription; (5) sequences derived from pBR322 and virus-associated sequences VAI and VAII of pDC201, with adenovirus sequences 10532–11156 containing the VAI and VAII genes, followed by pBR322 sequences from 4363–2486 and 1094–375 containing the ampicillin resistance gene and origin of replication.

Purification of Recombinant LIF-R

Purified recombinant mammalian LIF-Rs or analogs are prepared by culturing suitable host/vector systems to express the recombinant translation products of the DNAs of the present invention, which are then purified from culture media or cell extracts.

For example, supernatants from systems which secrete recombinant soluble LIF-R protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise an LIF or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a LIF-R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian LIF-R can be disrupted by any convenient method, including freeze-thaw cycling, sonication, mechanical disruption, or use of cell lysing agents.

Fermentation of yeast which express soluble mammalian LIF-R as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Human LIF-R synthesized in recombinant culture is characterized by the presence of non-human cell components, including proteins, in amounts and of a character which depend upon the purification steps taken to recover human LIF-R from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of LIF-R free of proteins which may be normally associated with LIF-R as it is found in nature in its species of origin, e.g. in cells, cell exudates or body fluids.

Uses of LIF-R Proteins and Compositions Comprising LIF-R

The LIF-R proteins disclosed herein find use as research reagents, as diagnostic reagents in in vitro assays, and in in vivo therapeutic procedures. Pharmaceutical compositions comprising an effective amount of LIF-R and a suitable diluent or carrier are provided by the present invention.

Cells expressing a membrane-bound recombinant LIF-R protein may be employed in studies of signal transduction; in various assays to detect LIF binding to the cells; or to analyze the ability of a particular protein (e.g., a soluble LIF-R) to compete with the membrane-bound LIF-R for binding of LIF. Labeled (e.g., radiolabeled) LIF-R may be used to assay a biological sample for LIF. Soluble LIF-R proteins are preferred for therapeutic use.

The present invention provides methods of using therapeutic compositions comprising a therapeutically effective amount of soluble LIF-R proteins and a suitable diluent and carrier, and methods for suppressing LIF-dependent biological responses in humans comprising administering an effective amount of soluble LIF-R protein. The therapeutically effective amount is an amount effective in ameliorating a LIF-mediated condition, and will vary according to the nature of the condition, the route of administration, the size of the patient, etc.

For therapeutic use, purified soluble LIF-R protein is administered to a patient, preferably a human, for treatment in a manner appropriate to the indication. Thus, for example, soluble LIF-R protein compositions can be administered by bolus injection, continuous infusion, sustained release from implants, or other suitable technique. Typically, a soluble LIF-R therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the LIF-R with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials.

Because LIF-R proteins bind to LIF, soluble LIF-R proteins can be used to competitively bind to LIF and thereby inhibit binding of LIF to cell surface LIF-R proteins. Soluble LIF-R is therefore expected to inhibit LIF-dependent biological activities. Soluble LIF-R may, for example, be useful in therapy to inhibit the effects of LIF induced cachexia in cancer patients or to treat lipoprotein metabolism defects such as atherosclerosis and obesity. Soluble LIF-R may also be useful in the treatment of disorders of bone and calcium metabolism or disorders associated with LIF overproduction associated with hepatocytes, neurons, and leukocytes. The regulation of embryonic and hematopoietic stem cells by LIF may also be manipulated with soluble LIF-R. Soluble LIF-R may also be used to treat leukemic cells which respond to LIF by proliferating.

LIF-R or antibodies to LIF-R may also be useful as a diagnostic reagent to detect diseases characterized by the presence of abnormal LIF-R.

Sense and Antisense Sequences

The present invention provides both double-stranded and single-stranded LIF-R DNA, and LIF-R mRNA as well. The single-stranded LIF-R nucleic acids have use as probes to detect the presence of hybridizing LIF-R nucleic acids (e.g., in in vitro assays) and as sense and antisense molecules to block expression of LIF-R.

In one embodiment, the present invention provides antisense or sense molecules comprising a single-stranded nucleic acid sequence (either RNA or DNA) capable of binding to target LIF-R mRNA (sense) or LIF-R DNA (antisense) sequences. These antisense or sense molecules may comprise a fragment of the coding region of LIF-R cDNA, and, in one embodiment, are oligonucleotides comprising at least about 14 nucleotides, preferably from about 14 to about 30 nucleotides, of a LIF-R cDNA sequence. The ability to create an antisense or sense oligonucleotide based upon a cDNA sequence for a given protein is described in, for example, Stein and Cohen, *Cancer Res.* 48:2659, 1988 and van der Krol et al., *BioTechniques* 6:958, 1988, which are hereby incorporated by reference.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The oligonucleotides thus may be used to block expression of LIF-R proteins. Uses of the antisense and sense nucleic acid sequences include, but are not limited to, use as research reagents. The biological effects of blocking LIF-R expression in cultured cells may be studied, for example. The oligonucleotides also may be employed in developing therapeutic procedures that involve blocking LIF-R expression *in vivo*.

Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are relatively stable *in vivo* (i.e., capable of resisting enzymatic degradation) but retain sequence specificity for binding to target nucleotide sequences. Other examples of sense or antisense oligonucleotides include those oligonucleotides which are covalently linked to organic moieties such as those described in WO 90/10448, or to other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any suitable method, including, for example, CaPO$_4$-mediated DNA transfection, electroporation, or by using gene transfer vectors such as Epstein-Barr virus. A preferred method involves insertion of the antisense or sense oligonucleotide into a suitable retroviral vector, then contacting the target cell with the retrovirus vector containing the inserted sequence, either *in vivo* or *ex vivo*. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by attaching the oligonucleotide to a molecule that binds to the target cell, as described in WO 91/04753. The oligonucleotide may be attached to molecules that include, but are not limited to, antibodies, growth factors, other cytokines, or other ligands that bind to cell surface receptors.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are offered by way of illustration, and not by way of limitation.

EXAMPLES

Example 1

Isolation and Expression of cDNAs Encoding Human LIF-R

A. Radiolabeling of LIF. Recombinant human LIF was expressed in yeast and purified to homogeneity essentially as described by Hopp, et al., *Bio/Technology* 6:1204, 1988. The purified protein was radiolabeled using a commercially available enzymobead radioiodination reagent (BioRad). In this procedure 10 μg rLIF in 50 μl 0.2M sodium phosphate, pH 7.2, are combined with 50 μl enzymobead reagent, 2 MCi of sodium iodide in 20 μl of 0.05M sodium phosphate pH 7.0 and 10 μl of 2.5% b-D-glucose. After 10 min at 25° C., sodium azide (20 μl of 50 mM) and sodium metabisulfite (10 μl of 5 mg/ml) were added and incubation continued for 5 min. at 25° C. The reaction mixture was fractionated by gel filtration on a 2 ml bed volume of Sephadex® G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-LIF was diluted to a working stock solution of $3 \times 10^{-8}$M in binding medium and stored for up to one month at 4° C. without detectable loss of receptor binding activity. The specific activity is routinely in the range of $6-8 \times 10^{15}$ cpm/mmole LIF.

B. Membrane Binding Assays. Human placental membranes were incubated at 4° C. for 2 hr with $^{125}$I-LIF in binding medium, 0.1% bacitracin, 0.02% aprotinin, and 0.4% BSA in a total volume of 1.2 ml. Control tubes containing in addition a 100-fold molar excess of unlabeled LIF were also included to determine nonspecific binding. The reaction mixture was then centrifuged at 15,000×g in a microfuge for 5 minutes. Supernatants were discarded, the surface of the membrane pellets carefully rinsed with ice-cold binding medium, and the radioactivity counted on a gamma counter. Using this assay, it was determined that the LIF-R was present on placental membranes, and up to 96 fmols of $^{125}$I-LIF could be bound per mg of placental membrane protein.

C. Construction and Screening of Placental cDNA Library. A tissue source for LIF-R was selected by screening various human cell lines and tissues for expression of LIF-R based on their ability to bind $^{125}$I-labeled LIF, prepared as described above in Example 1A. An unsized cDNA library was constructed by reverse transcription of polyadenylated mRNA isolated from total RNA extracted from the human placental tissue (Ausubel et al., eds., *Current Protocols in Molecular Biology*, Vol. 1, 1987). The cells were harvested by lysing the tissue cells in a guanidinium isothiocyanate solution and total RNA was isolated using standard techniques as described by Maniatis, *Molecular Cloning: A Laboratory Manual*, Cold Spring Harbor Laboratory, 1982.

Polyadenylated RNA was isolated by oligo dT cellulose chromatography and double-stranded cDNA was prepared by a method similar to that of Gubler and Hoffman, *Gene* 25:263, 1983. Briefly, the polyadenylated RNA was converted to an RNA-cDNA hybrid with reverse transcriptase using oligo dT as a primer. The RNA-cDNA hybrid was then converted into double-stranded cDNA using RNAase H in combination with DNA polymerase I. The resulting double stranded cDNA was blunt-ended with T4 DNA polymerase. BglII adaptors were ligated to the 5' ends of the resulting blunt-ended cDNA as described by Haymerle, et al., *Nucleic Acids Research* 14:8615, 1986. The non-ligated adaptors were removed by gel filtration chromatography at 68° C., leaving 24 nucleotide non-self-complementary overhangs on the cDNA. The same procedure was used to convert the 5' BglII ends of the mammalian expression vector pDC303 to 24 nucleotide overhangs complementary to those added to the cDNA.

The eukaryotic expression vector pDC303 was designed to express cDNA sequences inserted at its multiple cloning site when transfected into mammalian cells, and also replicates in *E. coli*. pDC303 was deposited in *E. coli* cells with the America Type Culture Collection on Feb. 27, 1992, under the designation *E. coli* DH5α, SF CAV, and was assigned accession no. 68922. pDC303 was assembled from pDC201 (a derivative of pMLSV, previously described by Cosman et al., *Nature* 312:768, 1984), SV40 and cytomegalovirus DNA and comprises, in sequence: (1) SV40 sequences from coordinates 5171-270 containing the origin of replication, enhancer sequences and early and late promoters; (2) cytomegalovirus sequences containing the promoter and enhancer regions (nucleotides 6711 to +63 from the sequence published by Boechart et al., *Cell* 41:521, 1985; (3) adenovirus-2 sequences from coordinates 5779-6079 containing sequences for the first exon of the tripartite leader (TPL), coordinates 7101-7172 and 9634-9693 containing the second exon and pan of the third exon of the TPL and a multiple cloning site (MCS) containing sites for XhoI, KpnI, SmaI and BglI; (4) SV40 sequences from coordinates 4127-4100 and 2770-2533 containing the polyadenylation and termination signals for early transcription; (5) adenovirus sequences from coordinates 10532-11156 of the virus-associated RNA genes VAI and VAII; and (6) pBR322 sequences from coordinates 4363-486 and 1094-375 containing the ampicillin resistance gene and origin of replication.

Optimal proportions of adaptoted vector and cDNA were ligated in the presence of T4 polynucleotide kinase. Dialyzed ligation mixtures were electroporated into *E. coli* strain DH5α and transformants selected on ampicillin plates. Transformed *E. coli* cells were plated to provide approximately 2,400 colonies per plate and sufficient plates to provide approximately 240,000 total colonies per screen. Colonies were scraped from each plate, pooled, and plasmid DNA prepared from each pool. The pooled DNA was then used to transfect a subconfluent layer of monkey COS-7 cells. COS-7 cells were prepared for transfection by being maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and then plated at a density of $2 \times 10^5$ cells/well in either 6 well dishes (Falcon) or single well chambered slides (Lab-Tek). Both dishes and slides were pretreated with 1 ml human fibronectin (10 µg/ml in PBS) for 30 minutes followed by 1 wash with PBS. Media was removed from the adherent cell layer and replaced with 1.5 ml complete medium containing 134 mM chloroquine sulfate. 0.2 mls of DNA solution (2 µg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for $2\frac{1}{2}$ to 20 minutes followed by replacement of the solution with fresh complete medium. The cells were grown in culture to permit transient expression of the inserted sequences. These conditions led to an 80% transfection frequency in surviving COS-7 cells.

After 48 to 72 hours, transfected monolayers of COS-7 cells were assayed for expression of LIF binding proteins by binding radioiodinated LIF (prepared as described above) using the following slide autoradiography technique. Transfected COS-7 cells were washed once with binding medium (RPMI media 1640 containing 25 mg/ml bovine serum albumin (BSA), 2 mg/ml sodium azide, 20 mM HEPES, pH 7.2, and 50 mg/ml nonfat dry milk (NFDM) and incubated for 2 hours at 4° C. with 1 ml binding medium+NFDM containing $1.25 \times 10^{-9}$ $^{125}$I-LIF. After incubation, cells in the chambered slides were washed three times with binding buffer+NFDM, followed by 2 washes with PBS, pH 7.3, to remove unbound $^{125}$I-LIF. The cells were fixed by incubating for 30 minutes at room temperature in 10% glutaraldehyde in PBS, pH 7.3, washed twice in PBS, and air dried. The slides were dipped in Kodak NTB-2 photographic emulsion (5× dilution in water) and exposed in the dark for 12 hours to 7 days at 4° C. in a light proof box. The slides were then developed for approximately 5 minutes in Kodak D 19 developer (40 g/500 ml water), rinsed in water and fixed in Agfa G433C fixer. The slides were individually examined with a microscope at 25–40× magnification and positive cells expressing LIF-R were identified by the presence of autoradiographic silver grains against a light background.

Cells in the 6 well plates were washed once with binding buffer+NFDM followed by washings with PBS, pH 7.3, to remove unbound $^{125}$I-LIF. The bound cells were then trypsinized to remove them from the plate and bound $^{125}$I-LIF were counted on a gamma counter.

Using the slide autoradiography approach, approximately 240,000 cDNAs were screened in pools of approximately 2,400 cDNAs until assay of one transfectant pool showed multiple cells clearly positive for LIF binding. This pool was then partitioned into pools of 600 and again screened by slide autoradiography and a positive pool was identified. This pool was further partitioned into pools of 60 and screened against by slide autoradiography until a positive pool was identified. Individual colonies from this pool of 60 were screened until a single clone (clone 65) was identified which directed synthesis of a surface protein with detectable LIF binding activity. This clone was isolated, and its insert is sequenced to determine the sequence of the human LIF-R cDNA clone 65. The pDC303 cloning vector containing the human LIF-R cDNA clone 65 was deposited with the American Type Culture Collection, Rockville, Md., USA (ATCC) on Dec. 11, 1990, under the name pHLIFR-65, and was assigned ATCC Accession Number 68491.

The nucleotide sequence of the cDNA insert of clone 65 is presented, along with the amino acid sequence encoded thereby, in SEQ ID NOS:1 and 2. Amino acids −44 through −1 constitute the signal peptide.

D. Binding to Intact Cells. Binding assays done with DA-1 cells grown in suspension culture were performed by a phthalate oil separation method (Dower et al., *J. Immunol.* 132:751, 1984) essentially as described by Park et al., *J. Biol. Chem* 261:4177, 1986 and Park et al., *Proc. Natl. Acad. Sci. USA* 84:5267, 1987. Nonspecific binding of $^{125}$I-LIF was measured in the presence of a 200-fold or greater molar excess of unlabeled LIF. Sodium azide (0.2%) was included in all binding assays to inhibit internalization of $^{125}$I-LIF at 37° C. The DA-1 cells bound $^{125}$I-LIF, and approximately 200 LIF receptors were determined to be present on the surface cells with an affinity constant ($K_a$) of about $7.4 \times 10^8$ M$^{-1}$.

Plasmid DNA from LIF receptor expression plasmid was used to transfect a subconfluent layer of monkey COS-7 cells using DEAE-dextran followed by chloroquine treatment, as described by Luthman et al. (*Nucl Acids Res.* 11:1295, 1983) and McCutchan et al. (*J. Natl. Cancer Inst.* 41:351, 1968). The cells were then grown in culture for three days to permit transient expression of the inserted sequences. After three days the cell monolayers were assayed for $^{125}$I-LIF binding essentially as described by Mosley et al., *Cell* 59:335, 1989. Nonspecific binding of $^{125}$I-LIF was measured in the presence of 200-fold or greater excess of unlabeled LIF. Initial binding studies of $^{125}$I-LIF to COS cells transfected with LIF-R cDNA clone 65 indicated that high affinity binding ($K_a > 1 \times 10^9$ M$^{-1}$) was apparent following Scatchard analysis. pDC303 control vector transfected cells indicated that background endogenous LIF receptors are present on COS-7 cells. Control vector transfected cells expressed 130 high-affinity LIF receptors ($K_a = 4.2 \times 10^{10}$ M$^{-1}$) and 2,400 receptors with lower affinity ($K_a = 7.8 \times 10^8$ M$^{-1}$). COS-7 cells were transfected with pDC303 containing LIF-R clone 65, and transfected cells were diluted 1:10 in cells that had been transfected with control pDC303 vector. This strategy was utilized as recombinant receptor expression can often be too great to allow accurate determinations of ligand-receptor affinity. Results of these experiments indicate that both affinity classes of LIF receptors were present following transfection with LIF-R clone 65. Approximately 178 high-affinity sites ($K_a = 1.4 \times 10^{-11}$ M$^{-1}$) and 9800 lower affinity sites ($K_a = 1.4 \times 10^{11}$ M$^{-1}$) were present on the LIF-R transfectants.

E. $^{35}$S-Labeling and Affinity Purification of LIF-R. COS-7 cells transfected with pDC303 or pDC303 containing the human LIF-R cDNA clone 65 were radiolabeled with $^{35}$S-cysteine/methionine. Detergent extracts of radiolabeled cells were prepared as described (Mosley et al., supra). LIF affinity matrices were prepared by coupling recombinant human LIF to cyanogen bromide-activated Sepharose (Pharmacia) or Hydrazide Affigel (Biorad), according to manufacturer's recommendations. A protein of $M_r$ approximately 190,000 was detected following affinity purification with either matrix, and SDS-PAGE analysis of LIF-R clone 65 COS-7 cell lysates, but was undetectable in control vector transfectants. The LIF-R clone 65 cDNA predicts a molecular weight of 111,374 and likely a high degree of glycosylation makes up the difference between this size and the observed $M_r$ of 190,000. Additionally, since the clone 65 LIF-R does not contain a stop codon in the 3' end of the cDNA, translation terminates 3 amino acids into the expression vector. Thus 401 daltons of the 190,000 LIF-R protein are encoded by these vector sequences.

F. Assay for Soluble LIF-R Proteins. Subclones derived from the extracellular domain of LIF-R cDNA clone 65 are assayed for the ability to encode soluble LIF-R proteins. COS-7 cells transfected with an expression vector containing the subcloned LIF-R cDNA are cultured to allow expression and secretion of the LIF-R protein. The presence of soluble LIF receptors in COS-7 supernatants is measured by inhibition of [$^{125}$I]-LIF binding to pHLIFR-65 transfected COS-7 cells. Supernatants from control and soluble LIFR subclone transfected COS-7 cells are harvested in DMEM with 0.1% FCS three days post-transfection. [$^{125}$I]LIF binding was assessed as described above in the presence of 0.5 ml conditioned media, or in the presence or absence of 200-fold molar excess unlabeled LIF. Analogous procedures may be employed to test for the presence of other soluble LIF-R proteins (e.g., soluble murine LIF-R) in culture supernatants.

A probe derived from clone 65 was used to isolate additional human LIF-R clones, as described in Example 4. A composite human LIF-R sequence, derived by sequencing and alignment of cDNA and genomic clones, is presented in SEQ ID NOS:5 and 6.

Example 2

Isolation and Purification of cDNA Clones Encoding Murine LIF-R

A murine LIF-R cDNA was isolated from a library made from mouse liver cDNA (Stratagene, San Diego, Cat. #35302), by cross-species hybridization with a human LIF-R probe. A double-stranded human LIF-R probe was produced by excising a BglII fragment of the human LIF-R clone 65 and 32P-labeling the cDNA using random primers (Boehringer-Mannheim). A total of about $5 \times 10^5$ plaques were screened with the human probe in 35% formamide. Murine LIF-R cDNA clone 3 was isolated. This particular clone encoded a soluble version of the LIF receptor. The coding region encodes a LIF-R having about 70% identity at the amino acid level (80% similarity) and about 78% identity at the nucleotide level to the human LIF-R in the region of overlap.

The nucleotide sequence of the murine LIF-R cDNA of clone 3, and the amino acid sequence encoded thereby, are presented in SEQ ID NOS:3 and 4. The protein comprises a signal peptide (amino acids −43 to −1).

Example 3

Preparation of Monoclonal Antibodies to LIF-R

Preparations of purified recombinant LIF-R, for example, human LIF-R, or transfected COS cells expressing high levels of LIF-R are employed to generate monoclonal antibodies against LIF-R using conventional techniques. The immunogen may comprise a LIF-R protein (or fragment thereof, such as the extracellular domain) fused to the peptide Asp-Tyr-Lys-Asp-Asp-Asp-Asp-Lys (DYKDDDDK) (Hopp et al., *Bio/Technology* 6:1204, 1988 and U.S. Pat. No. 5,011,912) or fused to the Fc portion of an antibody, as described above. Procedures for producing monoclonal antibodies include, for example, those disclosed in U.S. Pat. No. 4,411,993. Such antibodies are likely to be useful in interfering with LIF binding to LIF-R, for example, in ameliorating toxic or other undesired effects of LIF, or as components of diagnostic or research assays for LIF or soluble LIF-R.

To immunize mice, LIF-R immunogen is emulsified in complete Freund's adjuvant and injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS. Other suitable known myeloma cell lines may be employed in place of NS1. A prefered murine myeloma cell line is P3x63Ag8.653 (ATCC CRL 1580). Hybridoma cell lines generated by this procedure are plated in multiple microliter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with LIF-R, for example, by adaptations of the techniques disclosed by Engvall et al., *Immunochem.* 8:871 (1971) and in U.S. Pat. No. 4,703,004. A preferred screening technique is the antibody capture technique described in Beckmann et al., (*J. Immunol.* 144:4212, 1990). Positive clones are then injected into the peritoneal cavities of syngeneic Balb/c mice to produce ascites containing high concentrations (>1 mg/ml) of anti-LIF-R monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

Example 4

Isolation of Additional Human LIF-R Clones

Additional human LIF-R DNA sequences were isolated by screening human cDNA and genomic libraries with a probe derived from the human LIF-R cDNA isolated in Example 1. Sequencing and alignment of these clones produced the composite human LIF-R sequence presented in SEQ ID NOS:5 and 6.

The entire cDNA insert of pHLIFR-65 (Example 1) was excised by digestion with BglII, radiolabeled using a random priming kit (Stratagene Cloning Systems, La Jolla, Calif.), and used as a hybridization probe to screen the human placental cDNA library from which pHLIFR-65 was derived (Example 1). Hybridization procedures were essentially as described by Goodwin et al., supra, 1989. Positive clones were detected following high stringency washing conditions (0.2×XSSC, 0.1% SDS at 65° C.).

DNA sequences of hybridizing clones were determined using vector- and cDNA-derived oligonucleotide primers on denatured double-stranded templates following shotgun and directed subcloning according to standard procedures (Sambrook, J., Fritsch, E. F. and Maniatis, T. (1989) *Molecular Cloning: A Laboratory Manual*, 2nd Edition, Cold Spring Harbor Laboratory Press, New York).

As shown in SEQ ID NO:1, the cDNA insert in pHLIFR-65 (from Example 1) encoded a single large open reading frame that had no in-frame translation termination signal at its 3' end and, instead, ended in a stretch of 15 adenines (beginning after nucleotide 3143 in SEQ ID NO:1) that were not preceded by a typical polyadenylation signal. The open reading frame was terminated by an in-frame translational stop codon following 15 additional amino acids encoded by the Bgl II adaptors employed in library construction and by the expression vector. The 3' end of each additional isolated cDNA clone coincided with this poly-A stretch. Determination of the complete DNA sequence of one cDNA clone indicated that the sequences upstream of the poly A segment were identical to that of pHLIFR-65. Partial sequences were determined for the other clones, which matched corresponding portions of the pHLIFR-65 cDNA.

Based on the assumption that these cDNAs were the result of oligo(dT) priming at an internal site in the human LIFR mRNA during construction of the libraries, a human genomic library was screened with both the above-described probe containing the entire pHLIFR cDNA insert, and also with a $^{32}$P-labeled oligonucleotide having the sequence of nucleotides 3099–3115 of SEQ ID NO:1 (near the 3' end of human clone 65). Four hybridizing clones were isolated. A subclone derived from one of the genomic clones (HLIFR-gen1) contained sequence that extended the cDNA sequence beyond the point at which the poly-A stretch of nucleotides began in the cDNA clones.

The sequence of the open reading frame deduced by alignment of pHLIFR-65 cDNA with the 3' genomic sequence (until the first in-frame stop codon was encountered) is presented in FIGS. 2a through 2e and in SEQ ID NOS:5 and 6. In FIG. 2, the signal peptide comprises amino acids −44 to −1. The transmembrane domain is heavily underlined. Potential N-linked glycosylation sites are marked with asterisks. Hallmark residues associated with the hematopoietin family of receptors (Cosman et al., *Trends Biochem. Sci.*, 15:265 (1990) are shown boxed. The horizontal arrow marks the point at which genomic sequence was used to derive the 3' coding region of the HLIFR. All cDNA clones terminated with a stretch of A nucleotides at this point.

Comparison and alignment of the sequences of the positive clones produced the composite map of FIG. 1. In FIG. 1, clones isolated from the placental cDNA and genomic libraries are designated by "p" and "gen", respectively. The HLIFR open reading frame is shown boxed. The signal sequence is shown as a hatched box and the transmembrane domain is shown as a solid box. Some restriction endonuclease cleavage sites are shown.

In order to confirm that the genomic sequence used to complete the amino acid sequence of the HLIFR cytoplasmic domain was exonic, we used a PCR-based approach to detect the contiguous sequence assembled in FIGS. 2a through 2e in human placental cDNA. First strand cDNA was prepared on a human placental mRNA template, using random primers in place of the oligo dT primer suspected of annealing to an internal poly-A site in the previously-described cDNA library. The first strand cDNA was used as a template in a PCR reaction primed with oligonucleotides that span two introns in the HLIFR gene (intron 1 of >700 bp @nt 2770 and intron 2 of >900 bp @nt 2848 in FIG. 2d. The 5' primer employed in the PCR reaction (an oligonucleotide, the 5' end of which is at position 2720 of FIG. 2d) anneals within the transmembrane region of the human LIF-R DNA. One 3' primer (an oligonucleotide having a 5' end at position 3233 of FIG. 2e) anneals downstream of the point at which a poly-A segment is found in the previously isolated cDNAs (but within the coding region). The second 3' primer (an oligonucleotide having a 5' end at position 3529 of FIG. 2e) anneals within the 3' non-coding region of the FIG. 2e LIF-R sequence. The 5' oligonucleotide is based on the sequence of pHLIFR-65 and the 3' oligonucleotides are based on the sequence of the genomic clone. The PCR reaction products were separated by electrophoresis on an agarose gel, then transferred to nitrocellulose. The blot was probed with a 17-mer $^{32}$P-labeled oligonucleotide (nucleotides 3099-3115 of FIG. 2). First strand cDNA synthesis, the polymerase chain reaction and blotting from agarose gels were performed by procedures analogous to those described by Gearing et al., *EMBO J.* 8:3667-3676 (1989).

Amplification products expected if the composite FIG. 2 DNA sequence is exonic are 513 base pairs (5' primer to first 3' primer) and 809 base pairs (5' primer to the 3' primer in the noncoding region) in length. Specific amplification products of the predicted size were detected following PCR with the cDNA but not with genomic DNA as template. Since no bands were detected in the genomic PCR products it is likely that the distance between the primers (which includes the two introns discussed above) was too great for efficient PCR under the conditions used. The assembled sequence in FIGS. 2a through 2e and SEQ ID NO:5 therefore corresponds to the true sequence of the human LIFR cDNA.

A DNA sequence comprising the full length coding region shown in FIGS. 2a through 2e prepared by a number of different techniques. PCR reaction products produced as described above (with the 5' primer and the 3' primer that anneals in the 3' non-coding region) may be joined to the LIF-R cDNA of pHLIF-R-65 (example 1; contains 5' end of LIF-R sequence) by using a restriction endonuclease that cleaves within the region of overlap with the LIF-R cDNA of pHLIF-R-65. Computer programs that print out restriction sites within a given DNA sequence are known and available. In another approach, the genomic LIF-R DNA isolated above may be substituted for the PCR-amplified DNA, and joined to the pHLIF-R cDNA. Alternatively, the 3' end of the full length human LIF-R sequence may be chemically synthesized by conventional procedures and ligated to the pHLIF-R-65 cDNA (digested with a suitable restriction enzyme). As an additional alternative, a human placental cDNA library prepared using random primers for first strand cDNA synthesis may be screened with a probe derived from pHLIF-R-65 or the genomic clone isolated above to identify a full length cDNA clone.

The extracellular domain of the human LIF-R has homology to members of the hematopoietin receptor family (Cosman et al., supra) and contains two hematopoietin receptor domains (defined from the first conserved Cys residue to the Trp-Ser-X-Trp-Ser motif) and three repeats of a fibronectin type III-like module (FN III). The three FNIII domains span amino acids 487 (Thr) through 789 (Ser) of the SEQ ID NOS:2 and 6 sequences.

The presence of human LIFR cDNA clones in libraries prepared from placenta and liver suggests that the LIFR mRNA is normally expressed in these tissues. In order to define the size of the full-length LIFR mRNA, the cDNA insert of pHLIFR-65 was used to detect LIFR transcripts in human placental RNA. Resolution of RNA samples in agarose gels and transfer to nylon filters was accomplished as described previously (Goodwin et al., supra 1989). Blots were hybridized overnight with the entire insert of pHLIFR-65 that had been radiolabeled using a random priming kit (Stratagene), and washed using high stringency conditions.

Two major RNA species of ~6 kb and ~4.5 kb and a minor band of 5 kb were detected. These RNA species may represent alternately spliced transcripts, such as transcripts for membrane bound and soluble forms of the human LIF receptor, or transcripts utilizing different poly(A) addition signals.

Example 5

Soluble Human LIF-R/Fc Homodimer

An expression vector encoding a fragment of the human LIF-R extracellular domain fused to a polypeptide derived from the Fc region of an antibody was constructed as follows. Disulfide bonds form between the Fc portions of the expressed fusion proteins, creating homodimers.

Plasmid pHLIF-R-65, which contains human LIF-R cDNA in expression vector pDC303 as described in example 1, was digested with the restriction enzymes Asp718 and XmnI. Asp718 cleaves the vector upstream of the LIF-R cDNA insert. XmnI is a blunt cutter that cleaves within the codon for amino acid number 702 (Asp) of SEQ ID NO:1, upstream of the transmembrane region. The desired Asp718/XmnI fragment (about 2,444 bp in length) was separated by electrophoresis on an agarose gel and purified by conventional procedures, using an Elutip column.

CDNA encoding a single chain polypeptide derived from the Fc region of a human IgG1 antibody has been cloned into a pBLUESCRIPT SK® vector (Stratagene Cloning Systems, La Jolla, Calif.) to produce a recombinant vector designated hIgG1Fc. A polylinker region comprising a number of restriction sites is positioned immediately upstream of the Fc cDNA. The DNA and encoded amino acid sequences of the cloned Fc cDNA are presented in SEQ ID NO:7 and SEQ ID NO:8 (amino acids 14-245). Amino acids 1-13 of SEQ ID NOS:7 and 8 are encoded by the poly linker DNA segment. FIG. 4 shows the positions of cleavage sites for a number of restriction enzymes in the polylinker and the 5' end of the Fc DNA.

The Fc polypeptide encoded by the cDNA extends from the N-terminal hinge region to the native C-terminus, i.e., is an essentially full-length antibody Fc region. Fc fragments, e.g., those that are truncated at the C-terminal end, also may be employed. The fragments should contain multiple cysteine residues (at least the cysteine residues in the hinge reaction). The antibody from which the Fc polypeptide is derived is preferably of the same species as the patient to be treated with the fusion protein prepared therefrom.

Plasmid hIgG1Fc was digested with Asp718 and StuI, which cleave within the polylinker. The Asp 718/XmnI LIF-R fragment prepared above was ligated into the cleaved hIgG1Fc vector by conventional techniques. StuI and XmnI both produce blunt ends, which will ligate together. In the resulting recombinant vector, the Fc encoding sequence is positioned downstream of, and in the same reading frame as, the LIF-R sequence. The encoded LIF-R/Fc fusion protein comprises amino acids −44 to 702 of SEQ ID NO: 1, followed by amino acids 8 to 245 of SEQ ID NO:7. Amino acids 8 to 13 of SEQ ID NO:7 constitute a peptide linker encoded by the polylinker segment in this fusion protein. *E. coli* cells were transformed with the ligation mixture and plasmids were isolated therefrom by standard procedures. Plasmid vectors containing the desired DNA insert were identified by restriction endonuclease digestion analysis.

The cloned DNA segment encoding the LIF-R/Fc fusion polypeptide was excised from the recombinant vector by digestion with Asp718 and NotI. The NotI enzyme cleaves the vector in a polylinker region just downstream of the Fc cDNA insert. The excised DNA segment (3.2 kb) is inserted into an appropriate expression vector, depending on the type of host cell that is desired. One suitable expression vector is pDC304, a mammalian expression vector that is virtually identical to pDC303 (ATCC 68922, described in example 1) except that pDC304 contains a NotI site in the multiple cloning site (mcs). pDC304 is designed to express cDNA inserted into the mcs after transfection into mammalian cells.

pDC304 was cleaved with Asp718 and NotI, both of which cleave in the mcs. The LIF-R/Fc-encoding Asp718/NotI DNA fragment prepared above was ligated into the vector. COS-7 (monkey kidney) cells were transfected with the expression vector encoding the LIF-R/Fc fusion. The transfected cells were cultivated to allow expression of the fusion protein comprising the Fc polypeptide fused in frame (via the peptide linker) to the C-terminus of the LIF-R fragment. Disulfide bonds that form between the two Fc regions covalently link the two separate fusion polypeptides into a homodimer comprising two LIF-R polypeptides joined via disulfide bonds between the Fc moieties fused thereto. The LIF-R/Fc homodimer is a soluble protein.

The homodimer receptor protein may be purified using any of a number of conventional protein purification techniques. Since antibody Fc regions bind to protein A and protein G, affinity chromatography employing protein A or protein G attached to an insoluble support material may be employed in the purification process. In one procedure, one liter of culture supernatant containing the receptor is passed over a solid phase protein G column, and the column is then washed thoroughly with phosphate-buffered saline (PBS). The adsorbed Fc-containing fusion protein is eluted with 50 mM glycine buffer, pH 3, and brought to pH 7 with 2M Tris buffer, pH 9. Further purification may involve immunoaffinity column(s), e.g., affinity columns having LIF bound thereto.

In order to confirm dimer formation, COS-7 cells transfected with the hLIF-R/Fc-encoding expression vector were incubated with a mixture of $^{35}$S-methionine and $^{35}$S-cysteine for 3 hours. Duplicate 1-ml aliquots of the culture supernatant were incubated with 50 μl Protein G Sepharose beads (20% v/v, available from Pharmacia) overnight at 4° C. The beads were then pelleted by centrifugation, and protein was recovered from the beads with protein sample buffer ±β-mercaptoethanol (BME). The molecular weight of the recovered protein was analyzed by SDS-PAGE. As expected, a protein band corresponding to the LIF-R/Fc monomer (about 160 kd) was visualized for samples treated with the BME reducing agent. A band corresponding to a protein of about 320 kd (double the monomer size) was seen on the −BME sample gel. No 160 kd (monomer) band was visible on the −BME sample gel. The dimer is believed to form either intracellularly or upon secretion from the transfected cells.

The binding affinity of the homodimeric receptor for LIF was determined by performing a variation of a standard Scatchard analysis. The binding assay procedure was similar to that described by Mosley et al. (*Cell* 59:335, 1989) except that the receptor is attached to Protein G Sepharose beads, rather than being on the surface of transfected cells, during the assay. The LIF-R/FC fusion protein attached to the beads is believed to be at least predominantly in dimeric form, as indicated above.

COS cells transfected with the hLIF-R/Fc-encoding expression vector were cultivated for 3 days to allow expression and secretion of the hLIF-R/Fc protein. 14 mls of culture supernatant were mixed with 700 μl of 20% (v/v) Protein G Sepharose beads in PBS+0.1% Triton X, and incubated overnight at 4° C. on a rocking platform. The beads were then washed twice with Binding Media (RPMI 1640 medium containing 2.5% bovine serum albumin, 0.2% (v/v) sodium azide and 20 mM Hepes, pH 7.4) and resuspended to 1.7 mls with Binding Media. In a 96-well microtiter plate, samples comprising 50 μl of the resuspended beads plus 50 μBinding Medium plus one of ten 1:2 serial dilutions of $^{125}$I-LIF were incubated for 2 hours at 4° C. with shaking.

Tubes containing 250 μnewborn calf serum (NCS) were used in place of the phthalate oil-containing tubes used in the separation method referred to in example 1, section D. Duplicate 50 μsamples from the microtiter plate were applied to the tubes, which were then spun in a microfuge. Tubes were then cut, the radioactivity counted, and processed as for standard Scatchard analysis. The binding affinity of the homodimer for LIF ($9 \times 10^8$ M$^{-1}$) was comparable to that of the LIF-R encoded by clone 65 cDNA ($1.1 \times 10^9$ M$^{-1}$).

In an alternative construct, vector pHLIF-R-65 is cleaved with the restriction enzymes Asp718 and Bsp1286I. Asp718 cleaves in the vector upstream of the LIF-R cDNA insert. Bsp1286I cleaves just 3' of the codon for Val (amino acid 775 in SEQ ID NO: 1). The Asp718/Bsp1286I LIF-R DNA fragment may be fused to an Fc polypeptide-encoding DNA fragment using suitable oligonucleotide linkers if desired. An additional alternative construct may be prepared by digesting hIgG1Fc with Asp718 and BglII. The BglII site shown in FIG. 4 (within the Fc sequence, near the 5' end) is unique. An oligonucleotide may be employed to regenerate the 5' end of the Fc sequence (through the codon for Glu at position 13) and add a suitable restriction site (e.g., for XmnI or Bsp1286I) for joining a LIF-R sequence to the Fc sequence.

Description of the Sequence Listing

SEQ ID NO:1 and SEQ ID NO:2 show the nucleotide sequence and encoded amino acid sequence of human LIF-R clone 65. This particular clone is a 5' fragment, lacking the the 3' end of the coding region. The coding region spans from nucleotides 179-3182. The partial amino acid sequence of the mature peptide encoded by this nucleotide sequence is defined by amino acids 1-957. The predicted signal peptide is defined by amino acids −44 through −1. Though truncated at the C-terminus, the LIF-R protein encoded by clone 65 is capable of binding LIF, as described in Example 1.

SEQ ID NO:3 and SEQ ID NO:4 show the nucleotide sequence and encoded amino acid sequence of murine LIF-R clone 3. This particular clone is a naturally occurring soluble form of the murine LIF-R and has no transmembrane region. The absence of the transmembrane region allows the protein molecule to be transported through the cell membrane. The coding region spans from nucleotides 53–2212. The amino acid sequence of the mature peptide encoded by this nucleotide sequence is defined by amino acids 1–676. The predicted signal peptide is defined by amino acids −43 through −1.

SEQ ID NO:5 and SEQ ID NO:6 show a full length human LIF-R nucleotide sequence and the amino acid sequence encoded thereby. These sequences are composites derived from the sequencing of cDNA and genomic clones, as described in Example 4. The protein comprises a signal sequence (amino acids −44 through −1) followed by an extracellular domain (amino acids 1–789), a transmembrane region (amino acids 790–815), and a cytoplasmic domain (amino acids 816–1054).

SEQ ID NO:7 and SEQ ID NO:8 show the nucleotide sequence and amino acid sequence of a polylinker-encoded peptide (amino acids 1–13) fused to a polypeptide derived from the Fc region of a human IgG1 antibody (amino acids 14–245). The Fc polypeptide extends from the hinge region to the native C-terminus.

SEQUENCE LISTING ( 1 ) GENERAL INFORMATION:

( i ) APPLICANT: Gearing, David P.
                           Beckmann, M. P.
    ( i i ) TITLE OF INVENTION: Leukemia Inhibitory Factor Receptors
    ( i i i ) NUMBER OF SEQUENCES: 8
    ( i v ) CORRESPONDENCE ADDRESS:

( 2 ) INFORMATION FOR SEQ ID NO:1:

( i ) SEQUENCE CHARACTERISTICS:
        ( A ) LENGTH: 3182 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( i v ) ANTI-SENSE: N ( v ) FRAGMENT TYPE: N-terminal ( v i ) ORIGINAL SOURCE:
        ( F ) TISSUE TYPE-: Placenta ( v i i ) IMMEDIATE SOURCE:
        ( B ) CLONE: hulifr.65

( i x ) FEATURE:
        ( A ) NAME/KEY: CDS
        ( B ) LOCATION: 179..3182
        ( D ) OTHER INFORMATION:

( i x ) FEATURE:
        ( A ) NAME/KEY: matpeptide
        ( B ) LOCATION: 311..3179
        ( D ) OTHER INFORMATION:

( i x ) FEATURE:
        ( A ) NAME/KEY: sigpeptide
        ( B ) LOCATION: 179..310
        ( D ) OTHER INFORMATION:

( x i ) SEQUENCE DESCRIPTION: SEQ ID NO:1:

```
AGATCTTGGA  ACGAGACGAC  CTGCTCTCTC  TCCCAGAACG  TGTCTCTGCT  GCAAGGCACC           60

GGGCCCTTTC  GCTCTGCAGA  ACTGCACTTG  CAAGACCATT  ATCAACTCCT  AATCCCAGCT          120

CAGAAAGGGA  GCCTCTGCGA  CTCATTCATC  GCCCTCCAGG  ACTGACTGCA  TTGCACAG           178

ATG  ATG  GAT  ATT  TAC  GTA  TGT  TIG  AAA  CGA  CCA  TCC  TGG  ATG  GTG  GAC     226
Met  Met  Asp  Ile  Tyr  Val  Cys  Leu  Lys  Arg  Pro  Ser  Trp  Met  Val  Asp
-44            -40                      -35                      -30

AAT  AAA  AGA  ATG  AGG  ACT  GCT  TCA  AAT  TTC  CAG  TGG  CTG  TTA  TCA  ACA     274
Asn  Lys  Arg  Met  Arg  Thr  Ala  Ser  Asn  Phe  Gln  Tru  Leu  Leu  Ser  Thr
              -25                      -20                      -15

TTT  ATT  CTT  CTA  TAT  CTA  ATG  AAT  CAA  GTA  AAT  AGC  CAG  AAA  AAG  GGG     322
Phe  Ile  Leu  Leu  Tyr  Leu  Met  Asn  Gln  Val  Asn  Ser  Gln  Lys  Lys  Gly
         -10                       -5                        1

GCT  CCT  CAT  GAT  TTG  AAG  TGT  GTA  ACT  AAC  AAT  TTG  CAA  GTG  TGG  AAC     370
```

| | | | | | | | | | | | | | | | | |
|---|---|---|---|---|---|---|---|---|---|---|---|---|---|---|---|---|
| Ala | Pro | His | Asp | Leu | Lys | Cys | Val | Thr | Asn | Asn | Leu | Gln | Val | Trp | Asn | |
| 5 | | | | 10 | | | | | 15 | | | | | | 20 | |

| TGT | TCT | TGG | AAA | GCA | CCC | TCT | GGA | ACA | GGC | CGT | GGT | ACT | GAT | TAT | GAA | 418 |
|---|---|---|---|---|---|---|---|---|---|---|---|---|---|---|---|---|
| Cys | Ser | Trp | Lys | Ala | Pro | Ser | Gly | Thr | Gly | Arg | Gly | Thr | Asp | Tyr | Glu | |
| | | | | 25 | | | | | 30 | | | | | 35 | | |

| GTT | TGC | ATT | GAA | AAC | AGG | TCC | CGT | TCT | TGT | TAT | CAG | TTG | GAG | AAA | ACC | 466 |
|---|---|---|---|---|---|---|---|---|---|---|---|---|---|---|---|---|
| Val | Cys | Ile | Glu | Asn | Arg | Ser | Arg | Ser | Cys | Tyr | Gln | Leu | Glu | Lys | Thr | |
| | | | 40 | | | | | 45 | | | | | 50 | | | |

| AGT | ATT | AAA | ATT | CCA | GCT | CTT | TCA | CAT | GGT | GAT | TAT | GAA | ATA | ACA | ATA | 514 |
|---|---|---|---|---|---|---|---|---|---|---|---|---|---|---|---|---|
| Ser | Ile | Lys | Ile | Pro | Ala | Leu | Ser | His | Gly | Asp | Tyr | Glu | Ile | Thr | Ile | |
| | | 55 | | | | | 60 | | | | | 65 | | | | |

| AAT | TCT | CTA | CAT | GAT | TTT | GGA | AGT | TCT | ACA | AGT | AAA | TTC | ACA | CTA | AAT | 562 |
|---|---|---|---|---|---|---|---|---|---|---|---|---|---|---|---|---|
| Asn | Ser | Leu | His | Asp | Phe | Gly | Ser | Ser | Thr | Ser | Lys | Phe | Thr | Leu | Asn | |
| | 70 | | | | | 75 | | | | | 80 | | | | | |

| GAA | CAA | AAC | GTT | TCC | TTA | ATT | CCA | GAT | ACT | CCA | GAG | ATC | TTG | AAT | TTG | 610 |
|---|---|---|---|---|---|---|---|---|---|---|---|---|---|---|---|---|
| Glu | Gln | Asn | Val | Ser | Leu | Ile | Pro | Asp | Thr | Pro | Glu | Ile | Leu | Asn | Leu | |
| 85 | | | | | 90 | | | | | 95 | | | | | 100 | |

| TCT | GCT | GAT | TTC | TCA | ACC | TCT | ACA | TTA | TAC | CTA | AAG | TGG | AAC | GAC | AGG | 658 |
|---|---|---|---|---|---|---|---|---|---|---|---|---|---|---|---|---|
| Ser | Ala | Asp | Phe | Ser | Thr | Ser | Thr | Leu | Tyr | Leu | Lys | Trp | Asn | Asp | Arg | |
| | | | | 105 | | | | | 110 | | | | | 115 | | |

| GGT | TCA | GTT | TTT | CCA | CAC | CGC | TCA | AAT | GTT | ATC | TGG | GAA | ATT | AAA | GTT | 706 |
|---|---|---|---|---|---|---|---|---|---|---|---|---|---|---|---|---|
| Gly | Ser | Val | Phe | Pro | His | Arg | Ser | Asn | Val | Ile | Trp | Glu | Ile | Lys | Val | |
| | | | 120 | | | | | 125 | | | | | 130 | | | |

| CTA | CGT | AAA | GAG | AGT | ATG | GAG | CTC | GTA | AAA | TTA | GTG | ACC | CAC | AAC | ACA | 754 |
|---|---|---|---|---|---|---|---|---|---|---|---|---|---|---|---|---|
| Leu | Arg | Lys | Glu | Ser | Met | Glu | Leu | Val | Lys | Leu | Val | Thr | His | Asn | Thr | |
| | | 135 | | | | | 140 | | | | | 145 | | | | |

| ACT | CTG | AAT | GGC | AAA | GAT | ACA | CTT | CAT | CAC | TGG | AGT | TGG | GCC | TCA | GAT | 802 |
|---|---|---|---|---|---|---|---|---|---|---|---|---|---|---|---|---|
| Thr | Leu | Asn | Gly | Lys | Asp | Thr | Leu | His | His | Trp | Ser | Trp | Ala | Ser | Asp | |
| | 150 | | | | | 155 | | | | | 160 | | | | | |

| ATG | CCC | TTG | GAA | TGT | GCC | ATT | CAT | TTT | GTG | GAA | ATT | AGA | TGC | TAC | ATT | 850 |
|---|---|---|---|---|---|---|---|---|---|---|---|---|---|---|---|---|
| Met | Pro | Leu | Glu | Cys | Ala | Ile | His | Phe | Val | Glu | Ile | Arg | Cys | Tyr | Ile | |
| 165 | | | | | 170 | | | | | 175 | | | | | 180 | |

| GAC | AAT | CTT | CAT | TTT | TCT | GGT | CTC | GAA | GAG | TAG | AGT | GAC | TGG | AGC | CCT | 898 |
|---|---|---|---|---|---|---|---|---|---|---|---|---|---|---|---|---|
| Asp | Asn | Leu | His | Phe | Ser | Gly | Leu | Glu | Glu | Trp | Ser | Asp | Trp | Ser | Pro | |
| | | | | 185 | | | | | 190 | | | | | 195 | | |

| GTG | AAG | AAC | ATT | TCT | TGG | ATA | CCT | GAT | TCT | CAG | ACT | AAG | GTT | TTT | CCT | 946 |
|---|---|---|---|---|---|---|---|---|---|---|---|---|---|---|---|---|
| Val | Lys | Asn | Ile | Ser | Trp | Ile | Pro | Asp | Ser | Gln | Thr | Lys | Val | Phe | Pro | |
| | | | 200 | | | | | 205 | | | | | 210 | | | |

| CAA | GAT | AAA | GTG | ATA | CTT | GTA | GGC | TCA | GAC | ATA | ACA | TTT | TGT | TGT | GTG | 994 |
|---|---|---|---|---|---|---|---|---|---|---|---|---|---|---|---|---|
| Gln | Asp | Lys | Val | Ile | Leu | Val | Gly | Ser | Asp | Ile | Thr | Phe | Cys | Cys | Val | |
| | | 215 | | | | | 220 | | | | | 225 | | | | |

| AGT | CAA | GAA | AAA | GTG | TTA | TCA | GCA | CTG | ATT | GGC | CAT | ACA | AAC | TGC | CCC | 1042 |
|---|---|---|---|---|---|---|---|---|---|---|---|---|---|---|---|---|
| Ser | Gln | Glu | Lys | Val | Leu | Ser | Ala | Leu | Ile | Gly | His | Thr | Asn | Cys | Pro | |
| | 230 | | | | | 235 | | | | | 240 | | | | | |

| TTG | ATC | CAT | CTT | GAT | GGG | GAA | AAT | GTT | GCA | ATC | AAG | ATT | CGT | AAT | ATT | 1090 |
|---|---|---|---|---|---|---|---|---|---|---|---|---|---|---|---|---|
| Leu | Ile | His | Leu | Asp | Gly | Glu | Asn | Val | Ala | Ile | Lys | Ile | Arg | Asn | Ile | |
| 245 | | | | | 250 | | | | | 255 | | | | | 260 | |

| TCT | GTT | TCT | GCA | AGT | AGT | GGA | ACA | AAT | GTA | GTT | TTT | ACA | ACC | GAA | GAT | 1138 |
|---|---|---|---|---|---|---|---|---|---|---|---|---|---|---|---|---|
| Ser | Val | Ser | Ala | Ser | Ser | Gly | Thr | Asn | Val | Val | Phe | Thr | Thr | Glu | Asp | |
| | | | | 265 | | | | | 270 | | | | | 275 | | |

| AAC | ATA | TTT | GGA | ACC | GTT | ATT | TTT | GCT | GGA | TAT | CCA | CCA | GAT | ACT | CCT | 1186 |
|---|---|---|---|---|---|---|---|---|---|---|---|---|---|---|---|---|
| Asn | Ile | Phe | Gly | Thr | Val | Ile | Phe | Ala | Gly | Tyr | Pro | Pro | Asn | Thr | Pro | |
| | | | 280 | | | | | 285 | | | | | 290 | | | |

| CAA | CAA | CTG | AAT | TGT | GAG | ACA | CAT | GAT | TTA | AAA | GAA | ATT | ATA | TGT | AGT | 1234 |
|---|---|---|---|---|---|---|---|---|---|---|---|---|---|---|---|---|
| Gln | Gln | Leu | Asn | Cys | Glu | Thr | His | Asp | Leu | Lys | Glu | Ile | Ile | Cys | Ser | |
| | | 295 | | | | | 300 | | | | | 301 | | | | |

| TGG | AAT | CCA | GGA | AGG | GTG | ACA | GCG | TTG | GTG | GGC | CCA | CGT | GCT | ACA | AGC | 1282 |
|---|---|---|---|---|---|---|---|---|---|---|---|---|---|---|---|---|
| Trp | Asn | Pro | Gly | Arg | Val | Thr | Ala | Leu | Val | Gly | Pro | Arg | Ala | Thr | Ser | |
| | 310 | | | | | 315 | | | | | 320 | | | | | |

| TAC | ACT | TTA | GTT | GAA | AGT | TTT | TCA | GGA | AAA | TAT | GTT | AGA | CTT | AAA | AGA | 1330 |
|---|---|---|---|---|---|---|---|---|---|---|---|---|---|---|---|---|
| Tyr | Thr | Leu | Val | Glu | Ser | Phe | Ser | Gly | Lys | Tyr | Val | Arg | Leu | Lys | Arg | |
| 325 | | | | | 330 | | | | | 335 | | | | | 340 | |

| | | | | | | | | | | | | | | | |
|---|---|---|---|---|---|---|---|---|---|---|---|---|---|---|---|
| GCT | GAA | GCA | CCT | ACA | AAC | GAA | AGC | TAT | CAA | TTA | TTA | TTT | CAA | ATG | CTT | 1378 |
| Ala | Glu | Ala | Pro<br>345 | Thr | Asn | Glu | Ser | Tyr<br>350 | Gln | Leu | Leu | Phe | Gln<br>355 | Met | Leu |
| CCA | AAT | CAA | GAA | ATA | TAT | AAT | TTT | ACT | TTG | AAT | GCT | CAC | AAT | CCG | CTG | 1426 |
| Pro | Asn | Gln<br>360 | Glu | Ile | Tyr | Asn | Phe<br>365 | Thr | Leu | Asn | Ala | His<br>370 | Asn | Pro | Leu |
| GGT | CGA | TCA | CAA | TCA | ACA | ATT | TTA | GTT | AAT | ATA | ACT | GAA | AAA | GTT | TAT | 1474 |
| Gly | Arg | Ser<br>375 | Gln | Ser | Thr | Ile | Leu<br>380 | Val | Asn | Ile | Thr | Glu<br>385 | Lys | Val | Tyr |
| CCC | CAT | ACT | CCT | ACT | TCA | TTC | AAA | GTG | AAG | GAT | ATT | AAT | TCA | ACA | GCT | 1522 |
| Pro | His<br>390 | Thr | Pro | Thr | Ser | Phe<br>395 | Lys | Val | Lys | Asp | Ile<br>400 | Asn | Ser | Thr | Ala |
| GTT | AAA | CTT | TCT | TGG | CAT | TTA | CCA | GGC | AAC | TTT | GCA | AAG | ATT | AAT | TTT | 1570 |
| Val<br>405 | Lys | Leu | Ser | Trp | His<br>410 | Leu | Pro | Gly | Asn | Phe<br>415 | Ala | Lys | Ile | Asn | Phe<br>420 |
| TTA | TGT | GAA | ATT | GAA | ATT | AAG | AAA | TCT | AAT | TCA | GTA | CAA | GAG | CAG | CGG | 1618 |
| Leu | Cys | Glu | Ile | Glu<br>425 | Ile | Lys | Lys | Ser | Asn<br>430 | Ser | Val | Gln | Glu | Gln<br>435 | Arg |
| AAT | GTC | ACA | ATC | AAA | GGA | GTA | GAA | AAT | TCA | AGT | TAT | CTT | GTT | GCT | CTG | 1666 |
| Asn | Val | Thr | Ile<br>440 | Lys | Gly | Val | Glu | Asn<br>445 | Ser | Ser | Tyr | Leu | Val<br>450 | Ala | Leu |
| GAC | AAG | TTA | AAT | CCA | TAC | ACT | CTA | TAT | ACT | TTT | CGG | ATT | CGT | TGT | TCT | 1714 |
| Asp | Lys | Leu<br>455 | Asn | Pro | Tyr | Thr | Leu<br>460 | Tyr | Thr | Phe | Arg | Ile<br>465 | Arg | Cys | Ser |
| ACT | GAA | ACT | TTC | TGG | AAA | TGG | ACC | AAA | TGG | AGC | AAT | AAA | AAA | CAA | CAT | 1762 |
| Thr | Glu<br>470 | Thr | Phe | Trp | Lys | Trp<br>475 | Thr | Lys | Trp | Ser | Asn<br>480 | Lys | Lys | Gln | His |
| TTA | ACA | ACA | GAA | GCC | AGT | CCT | TCA | AAG | GGG | CCT | GAT | ACT | TGG | AGA | GAG | 1810 |
| Leu<br>485 | Thr | Thr | Glu | Ala | Ser<br>490 | Pro | Ser | Lys | Gly | Pro<br>495 | Asn | Thr | Trp | Arg | Glu<br>500 |
| TGG | AGT | TCT | GAT | GGA | AAA | AAT | TTA | ATA | ATC | TAT | TGG | AAG | CCT | TTA | CCC | 1858 |
| Trp | Ser | Ser | Asp | Gly<br>505 | Lys | Asn | Leu | Ile | Ile<br>510 | Tyr | Trp | Lys | Pro | Leu<br>515 | Pro |
| ATT | AAT | GAA | GCT | AAT | GGA | AAA | ATA | CTT | TCC | TAC | AAT | GTA | TCG | TGT | TCA | 1906 |
| Ile | Asn | Glu | Ala<br>520 | Asn | Gly | Lys | Ile | Leu<br>525 | Ser | Tyr | Asn | Val | Ser<br>530 | Cys | Ser |
| TCA | GAT | GAG | GAA | ACA | CAG | TCC | CTT | TCT | GAA | ATC | CCT | GAT | CCT | CAG | CAC | 1954 |
| Ser | Asp | Glu<br>535 | Glu | Thr | Gln | Ser | Leu<br>540 | Ser | Glu | Ile | Pro | Asp<br>545 | Pro | Gln | His |
| AAA | GCA | GAG | ATA | CGA | CTT | GAT | AAG | AAT | GAC | TAC | ATC | ATC | AGC | GTA | GTG | 2002 |
| Lys | Ala<br>550 | Glu | Ile | Arg | Leu | Asp<br>555 | Lys | Asn | Asp | Tyr | Ile<br>560 | Ile | Ser | Val | Val |
| GCT | AAA | AAT | TCT | GTG | GGC | TCA | TCA | CCA | CCT | TCC | AAA | ATA | GCG | AGT | ATG | 2050 |
| Ala<br>565 | Lys | Asn | Ser | Val | Gly<br>570 | Ser | Ser | Pro | Pro | Ser<br>575 | Lys | Ile | Ala | Ser | Met<br>580 |
| GAA | ATT | CCA | AAT | GAT | GAT | CTC | AAA | ATA | GAA | CAA | GTT | GTT | GGG | ATG | GGA | 2098 |
| Glu | Ile | Pro | Asn | Asp<br>585 | Asp | Leu | Lys | Ile | Glu<br>590 | Gln | Val | Val | Gly | Met<br>595 | Gly |
| AAG | GGG | ATT | CTC | CTC | ACC | TGG | CAT | TAC | GAC | CCC | AAC | ATG | ACT | TGC | GAC | 2146 |
| Lys | Gly | Ile | Leu<br>600 | Leu | Thr | Trp | His | Tyr<br>605 | Asp | Pro | Asn | Met | Thr<br>610 | Cys | Asp |
| TAC | GTC | ATT | AAG | TGG | TGT | AAC | TCG | TCT | CGG | TCG | GAA | CCA | TGC | CTT | ATG | 2194 |
| Tyr | Val | Ile<br>615 | Lys | Trp | Cys | Asn | Ser<br>620 | Ser | Arg | Ser | Glu | Pro<br>625 | Cys | Leu | Met |
| GAC | TGG | AGA | AAA | GTT | CCC | TCA | AAC | AGC | ACT | GAA | ACT | GTA | ATA | GAA | TCT | 2242 |
| Asp | Trp | Arg<br>630 | Lys | Val | Pro | Ser | Asn<br>635 | Ser | Thr | Glu | Thr | Val<br>640 | Ile | Glu | Ser |
| GAT | GAG | TTT | CGA | CCA | GGT | ATA | AGA | TAT | AAT | TTT | TTC | CTG | TAT | GGA | TGC | 2290 |
| Asp<br>645 | Glu | Phe | Arg | Pro | Gly<br>650 | Ile | Arg | Tyr | Asn | Phe<br>655 | Phe | Leu | Tyr | Gly | Cys<br>660 |
| AGA | AAT | CAA | GGA | TAT | CAA | TTA | TTA | CGC | TCC | ATG | ATT | GGA | TAT | ATA | GAA | 2338 |

```
Arg Asn Gln Gly Tyr Gln Leu Leu Arg Ser Met Ile Gly Tyr Ile Glu
            665                 670                 675

GAA TTG GCT CCC ATT GTT GCA CCA AAT TTT ACT GTT GAG GAT ACT TCT        2386
Glu Leu Ala Pro Ile Val Ala Pro Asn Phe Thr Val Glu Asp Thr Ser
            680                 685                 690

GCA GAT TCG ATA TTA GTA AAA TGG GAA GAC ATT CCT GTG GAA GAA CTT        2434
Ala Asp Ser Ile Leu Val Lys Trp Glu Asp Ile Pro Val Glu Glu Leu
            695                 700                 705

AGA GGC TTT TTA AGA GGA TAT TTG TTT TAC TTT GGA AAA GGA GAA AGA        2482
Arg Gly Phe Leu Arg Gly Tyr Leu Phe Tyr Phe Gly Lys Gly Glu Arg
            710                 715                 720

GAC ACA TCT AAG ATG AGG GTT TTA GAA TCA GGT CGT TCT GAC ATA AAA        2530
Asp Thr Ser Lys Met Arg Val Leu Glu Ser Gly Arg Ser Asp Ile Lys
725                 730                 735                 740

GTT AAG AAT ATT ACT GAC ATA TCC CAG AAG ACA CTG AGA ATT GCT GAT        2578
Val Lys Asn Ile Thr Asp Ile Ser Gln Lys Thr Leu Arp Ile Ala Asp
                    745                 750                 755

CTT CAA GGT AAA ACA AGT TAC CAC CTG GTC TTG CGA GCC TAT ACA GAT        2626
Leu Gln Gly Lys Thr Ser Tyr His Leu Val Leu Arg Ala Tyr Thr Asp
                760                 765                 770

GGT GGA GTG GGC CCG GAG AAG AGT ATG TAT GTG GLG ACA AAG GAA AAT        2674
Gly Gly Val Gly Pro Glu Lys Ser Met Tyr Val Val Thr Lys Glu Asn
            775                 780                 785

TCT GTG GGA TTA ATT ATT GCC ATT CTC ATC CCA GTG GCA GTG GCT GTC        2722
Ser Val Gly Leu Ile Ile Ala Ile Leu Ile Pro Val Ala Val Ala Val
            790                 795                 800

ATT GTT GGA GTG GUG ACA AGT ATC CTT TGC TAT CGG AAA CGA GAA TGG        2770
Ile Val Gly Val Val Thr Ser Ile Leu Cys Tyr Arg Lys Arg Glu Trp
805                 810                 815                 820

ATT AAA GAA ACC TTC TAC CCT GAT ATT CCA AAT CCA GAA AAC TGT AAA        2818
Ile Lys Glu Thr Phe Tyr Pro Asp Ile Pro Asn Pro Glu Asn Cys Lys
                    825                 830                 835

GCA TTA CAG TTT CAA AAG AGT GTC TGT GAG GGA AGC AGT GCT CTT AAA        2866
Ala Leu Gln Phe Gln Lys Ser Val Cys Glu Gly Ser Ser Ala Leu Lys
                840                 845                 850

ACA TTG GAA ATG AAT CCT TGT ACC CCA AAT AAT GTT GAG GTT CTG GAA        2914
Thr Leu Glu Met Asn Pro Cys Thr Pro Asn Asn Val Glu Val Leu Glu
            855                 860                 865

ACT CGA TCA GCA TTT CCT AAA ATA GAA GAT ACA GAA ATA ATT TCC CCA        2962
Thr Arg Ser Ala Phe Pro Lys Ile Glu Asp Thr Glu Ile Ile Ser Pro
870                 875                 880

GTA GCT GAG CGT CCT GAA GAT CGC TCT GAT GCA GAG CCT GAA AAC CAT        3010
Val Ala Glu Arg Pro Glu Asp Arg Ser Asp Ala Glu Pro Glu Asn His
885                 890                 895                 900

GTG GTT GTG TCC TAT TGT CCA CCC ATC ATT GAG GAA GAA ATA CCA AAC        3058
Val Val Val Ser Tyr Cys Pro Pro Ile Ile Glu Glu Glu Ile Pro Asn
                905                 910                 915

CCA GCC GCA GAT GAA CCT GGA GGG ACT GCA CAG GTT ATT TAC ATT GAT        3106
Pro Ala Ala Asp Glu Ala Gly Gly Thr Ala Gln Val Ile Tyr Ile Asp
                920                 925                 930

GTT CAG TCG ATG TAT CAG CCT CAA GCA AAA CCA GAA GAA AAA AAA AAA        3154
Val Gln Ser Met Tyr Gln Pro Gln Ala Lys Pro Glu Glu Lys Lys Lys
            935                 940                 945

AAA AGC AGG TCG TCT CGT TCC AAG ATC T                                  3182
Lys Ser Arg Ser Ser Arg Ser Lys Ile
950                 955
```

( 2 ) INFORMATION FOR SEQ ID NO:2:

( i ) SEQUENCE CHARACTERISTICS:

( A ) LENGTH: 1001 amino acids
        ( B ) TYPE: amino acid ( D ) TOPOLOGY: linear ( i i ) MOLECULE TYPE: protein ( x i ) SEQUENCE DESCRIPTION: SEQ ID NO:2:

| Met | Met | Asp | Ile | Tyr | Val | Cys | Leu | Lys | Arg | Pro | Ser | Trp | Met | Val | Asp |
|-----|-----|-----|-----|-----|-----|-----|-----|-----|-----|-----|-----|-----|-----|-----|-----|
| -44 |     |     |     | -40 |     |     |     |     | -35 |     |     |     |     |     | -30 |

| Asn | Lys | Arg | Met | Arg | Thr | Ala | Ser | Asn | Phe | Gln | Trp | Leu | Leu | Ser | Thr |
|-----|-----|-----|-----|-----|-----|-----|-----|-----|-----|-----|-----|-----|-----|-----|-----|
|     |     |     | -25 |     |     |     |     | -20 |     |     |     |     |     | -15 |     |

| Phe | Ile | Leu | Leu | Tyr | Leu | Met | Asn | Gln | Val | Asn | Ser | Gln | Lys | Lys | Gly |
|-----|-----|-----|-----|-----|-----|-----|-----|-----|-----|-----|-----|-----|-----|-----|-----|
|     |     |     | -10 |     |     |     |     | -5  |     |     |     |     | 1   |     |     |

| Ala | Pro | His | Asp | Leu | Lys | Cys | Val | Thr | Asn | Asn | Leu | Gln | Val | Trp | Asn |
|-----|-----|-----|-----|-----|-----|-----|-----|-----|-----|-----|-----|-----|-----|-----|-----|
| 5   |     |     |     |     | 10  |     |     |     |     | 15  |     |     |     |     | 20  |

| Cys | Ser | Trp | Lys | Ala | Pro | Ser | Gly | Thr | Gly | Arg | Gly | Thr | Asp | Tyr | Glu |
|-----|-----|-----|-----|-----|-----|-----|-----|-----|-----|-----|-----|-----|-----|-----|-----|
|     |     |     |     | 25  |     |     |     |     | 30  |     |     |     |     | 35  |     |

| Val | Cys | Ile | Glu | Asn | Arg | Ser | Arg | Ser | Cys | Tyr | Gln | Leu | Glu | Lys | Thr |
|-----|-----|-----|-----|-----|-----|-----|-----|-----|-----|-----|-----|-----|-----|-----|-----|
|     |     |     |     | 40  |     |     |     |     | 45  |     |     |     |     | 50  |     |

| Ser | Ile | Lys | Ile | Pro | Ala | Leu | Ser | His | Gly | Asp | Tyr | Glu | Ile | Thr | Ile |
|-----|-----|-----|-----|-----|-----|-----|-----|-----|-----|-----|-----|-----|-----|-----|-----|
|     |     | 55  |     |     |     |     | 60  |     |     |     |     | 65  |     |     |     |

| Asn | Ser | Leu | His | Asn | Phe | Gly | Ser | Ser | Thr | Ser | Lys | Phe | Thr | Leu | Asn |
|-----|-----|-----|-----|-----|-----|-----|-----|-----|-----|-----|-----|-----|-----|-----|-----|
|     | 70  |     |     |     |     | 75  |     |     |     |     | 80  |     |     |     |     |

| Glu | Gln | Asn | Val | Ser | Leu | Ile | Pro | Asp | Thr | Pro | Glu | Ile | Leu | Asn | Leu |
|-----|-----|-----|-----|-----|-----|-----|-----|-----|-----|-----|-----|-----|-----|-----|-----|
| 85  |     |     |     |     | 90  |     |     |     |     | 95  |     |     |     |     | 100 |

| Ser | Ala | Asn | Phe | Ser | Thr | Ser | Thr | Leu | Tyr | Leu | Lys | Trp | Asn | Asp | Arg |
|-----|-----|-----|-----|-----|-----|-----|-----|-----|-----|-----|-----|-----|-----|-----|-----|
|     |     |     |     | 105 |     |     |     |     | 110 |     |     |     |     | 115 |     |

| Gly | Ser | Val | Phe | Pro | His | Arg | Ser | Asn | Val | Ile | Trp | Glu | Ile | Lys | Val |
|-----|-----|-----|-----|-----|-----|-----|-----|-----|-----|-----|-----|-----|-----|-----|-----|
|     |     |     | 120 |     |     |     |     | 125 |     |     |     |     | 130 |     |     |

| Leu | Arg | Lys | Glu | Ser | Met | Glu | Leu | Val | Lys | Leu | Val | Thr | His | Asn | Thr |
|-----|-----|-----|-----|-----|-----|-----|-----|-----|-----|-----|-----|-----|-----|-----|-----|
|     |     | 135 |     |     |     |     | 140 |     |     |     |     | 145 |     |     |     |

| Thr | Leu | Asn | Gly | Lys | Asp | Thr | Leu | His | His | Trp | Ser | Trp | Ala | Ser | Asp |
|-----|-----|-----|-----|-----|-----|-----|-----|-----|-----|-----|-----|-----|-----|-----|-----|
|     | 150 |     |     |     |     | 155 |     |     |     |     | 160 |     |     |     |     |

| Met | Pro | Leu | Glu | Cys | Ala | Ile | His | Phe | Val | Glu | Ile | Arg | Cys | Tyr | Ile |
|-----|-----|-----|-----|-----|-----|-----|-----|-----|-----|-----|-----|-----|-----|-----|-----|
| 165 |     |     |     |     | 170 |     |     |     |     | 175 |     |     |     |     | 180 |

| Asp | Asn | Leu | His | Phe | Ser | Gly | Leu | Glu | Glu | Trp | Ser | Asn | Trp | Ser | Pro |
|-----|-----|-----|-----|-----|-----|-----|-----|-----|-----|-----|-----|-----|-----|-----|-----|
|     |     |     |     | 185 |     |     |     |     | 190 |     |     |     |     | 195 |     |

| Val | Lys | Asn | Ile | Ser | Trp | Ile | Pro | Asn | Ser | Gln | Thr | Lys | Val | Phe | Pro |
|-----|-----|-----|-----|-----|-----|-----|-----|-----|-----|-----|-----|-----|-----|-----|-----|
|     |     |     | 200 |     |     |     |     | 205 |     |     |     |     | 210 |     |     |

| Gln | Asp | Lys | Val | Ile | Leu | Val | Gly | Ser | Asn | Ile | Thr | Phe | Cys | Cys | Val |
|-----|-----|-----|-----|-----|-----|-----|-----|-----|-----|-----|-----|-----|-----|-----|-----|
|     |     | 215 |     |     |     |     | 220 |     |     |     |     | 225 |     |     |     |

| Ser | Gln | Glu | Lys | Val | Leu | Ser | Ala | Leu | Ile | Gly | His | Thr | Asn | Cys | Pro |
|-----|-----|-----|-----|-----|-----|-----|-----|-----|-----|-----|-----|-----|-----|-----|-----|
|     | 230 |     |     |     |     | 235 |     |     |     |     | 240 |     |     |     |     |

| Leu | Ile | His | Leu | Asp | Gly | Glu | Asn | Val | Ala | Ile | Lys | Ile | Arg | Asn | Ile |
|-----|-----|-----|-----|-----|-----|-----|-----|-----|-----|-----|-----|-----|-----|-----|-----|
| 250 |     |     |     |     | 255 |     |     |     |     | 260 |     |     |     |     |     |

| Ser | Val | Ser | Ala | Ser | Ser | Gly | Thr | Asn | Val | Val | Phe | Thr | Thr | Glu | Asp |
|-----|-----|-----|-----|-----|-----|-----|-----|-----|-----|-----|-----|-----|-----|-----|-----|
|     |     |     |     | 265 |     |     |     |     | 270 |     |     |     |     | 275 |     |

| Asn | Ile | Phe | Gly | Thr | Val | Ile | Phe | Ala | Gly | Tyr | Pro | Pro | Asp | Thr | Pro |
|-----|-----|-----|-----|-----|-----|-----|-----|-----|-----|-----|-----|-----|-----|-----|-----|
|     |     |     |     | 280 |     |     |     |     | 285 |     |     |     |     | 290 |     |

| Gln | Gln | Leu | Asn | Cys | Glu | Thr | His | Asp | Leu | Lys | Glu | Ile | Ile | Cys | Ser |
|-----|-----|-----|-----|-----|-----|-----|-----|-----|-----|-----|-----|-----|-----|-----|-----|
|     |     |     | 295 |     |     |     |     | 300 |     |     |     |     | 305 |     |     |

| Trp | Asn | Pro | Gly | Arg | Val | Thr | Ala | Leu | Val | Gly | Pro | Arg | Ala | Thr | Ser |
|-----|-----|-----|-----|-----|-----|-----|-----|-----|-----|-----|-----|-----|-----|-----|-----|
|     | 310 |     |     |     |     | 315 |     |     |     |     | 320 |     |     |     |     |

| Tyr | Thr | Leu | Val | Glu | Ser | Phe | Ser | Gly | Lys | Tyr | Val | Arg | Leu | Lys | Arg |
|-----|-----|-----|-----|-----|-----|-----|-----|-----|-----|-----|-----|-----|-----|-----|-----|
| 330 |     |     |     |     | 335 |     |     |     |     | 340 |     |     |     |     |     |

| Ala | Glu | Ala | Pro | Thr | Asn | Glu | Ser | Tyr | Gln | Leu | Leu | Phe | Gln | Met | Leu |
|-----|-----|-----|-----|-----|-----|-----|-----|-----|-----|-----|-----|-----|-----|-----|-----|
|     |     |     |     | 345 |     |     |     |     | 350 |     |     |     |     | 355 |     |

| Pro | Asn | Gln | Glu | Ile | Tyr | Asn | Phe | Thr | Leu | Asn | Ala | His | Asn | Pro | Leu |

|     |     |     | 360 |     |     |     | 365 |     |     |     | 370 |     |     |
| --- | --- | --- | --- | --- | --- | --- | --- | --- | --- | --- | --- | --- | --- |
| Gly | Arg | Ser | Gln | Ser | Thr | Ile | Leu | Val | Asn | Ile | Thr | Glu | Lys | Val | Tyr |
|     |     |     | 375 |     |     |     | 380 |     |     |     | 385 |     |     |
| Pro | His | Thr | Pro | Thr | Ser | Phe | Lys | Val | Lys | Asp | Ile | Asn | Ser | Thr | Ala |
|     |     |     | 390 |     |     |     | 395 |     |     |     | 400 |     |     |
| Val | Lys | Leu | Ser | Trp | His | Leu | Pro | Gly | Asn | Phe | Ala | Lys | Ile | Asn | Phe |
| 410 |     |     |     |     | 425 |     |     |     | 420 |     |     |     |     |
| Leu | Cys | Glu | Ile | Glu | Ile | Lys | Lys | Ser | Asn | Ser | Val | Gln | Glu | Gln | Arg |
|     |     |     |     | 425 |     |     |     | 430 |     |     |     |     | 435 |
| Asn | Val | Thr | Ile | Lys | Gly | Val | Glu | Asn | Ser | Ser | Tyr | Leu | Val | Ala | Leu |
|     |     |     | 440 |     |     |     | 445 |     |     |     |     | 450 |
| Asp | Lys | Leu | Asn | Pro | Tyr | Thr | Leu | Tyr | Thr | Phe | Arg | Ile | Arg | Cys | Ser |
|     |     |     | 455 |     |     |     | 460 |     |     |     | 465 |     |     |
| Thr | Glu | Thr | Phe | Trp | Lys | Trp | Ser | Lys | Trp | Ser | Asn | Lys | Lys | Gln | His |
|     | 470 |     |     |     |     | 475 |     |     |     | 480 |     |     |
| Leu | Thr | Thr | Glu | Ala | Ser | Pro | Ser | Lys | Gly | Pro | Asp | Thr | Trp | Arg | Glu |
| 490 |     |     |     |     | 495 |     |     |     | 500 |     |     |     |     |
| Trp | Ser | Ser | Asp | Gly | Lys | Asn | Leu | Ile | Ile | Tyr | Try | Lys | Pro | Leu | Pro |
|     |     |     |     | 505 |     |     |     | 510 |     |     |     |     | 515 |
| Ile | Asn | Glu | Ala | Asn | Gly | Lys | Ile | Leu | Ser | Tyr | Asn | Val | Ser | Cys | Ser |
|     |     |     |     | 520 |     |     |     | 525 |     |     |     | 530 |     |
| Ser | Asp | Glu | Glu | Thr | Gln | Ser | Leu | Ser | Glu | Ile | Pro | Asp | Pro | Gln | His |
|     |     | 535 |     |     |     |     | 540 |     |     |     | 545 |     |     |
| Lys | Ala | Glu | Ile | Arg | Leu | Asp | Lys | Asn | Asp | Tyr | Ile | Ile | Ser | Val | Val |
|     | 550 |     |     |     |     | 555 |     |     |     | 560 |     |     |     |
| Ala | Lys | Asn | Ser | Val | Gly | Ser | Ser | Pro | Pro | Ser | Lys | Ile | Ala | Ser | Met |
| 565 |     |     |     |     | 570 |     |     |     | 575 |     |     |     |     | 580 |
| Glu | Ile | Pro | Asn | Asp | Asp | Leu | Lys | Ile | Glu | Gln | Val | Val | Gly | Met | Gly |
|     |     |     |     | 585 |     |     |     | 590 |     |     |     |     | 595 |
| Lys | Gly | Ile | Leu | Leu | Thr | Trp | His | Tyr | Asp | Pro | Asn | Met | Thr | Cys | Asp |
|     |     |     | 600 |     |     |     | 605 |     |     |     | 610 |     |     |
| Tyr | Val | Ile | Lys | Trp | Cys | Asn | Ser | Arg | Ser | Glu | Pro | Cys | Leu | Met |
|     |     | 615 |     |     |     | 620 |     |     |     | 625 |     |     |     |
| Asp | Trp | Arg | Lys | Val | Pro | Ser | Asn | Ser | Thr | Glu | Thr | Val | Ile | Glu | Ser |
|     | 630 |     |     |     |     | 635 |     |     |     | 640 |     |     |     |
| Asp | Glu | Phe | Arg | Pro | Gly | Ile | Arg | Tyr | Asn | Phe | Phe | Leu | Tyr | Gly | Cys |
| 650 |     |     |     |     | 655 |     |     |     | 660 |     |     |     |     |
| Arg | Asn | Gln | Gly | Tyr | Gln | Leu | Leu | Arg | Ser | Met | Ile | Gly | Tyr | Ile | Glu |
|     |     |     |     | 665 |     |     |     | 670 |     |     |     |     | 675 |
| Glu | Leu | Ala | Pro | Ile | Val | Ala | Pro | Asn | Phe | Thr | Val | Glu | Asn | Thr | Ser |
|     |     |     | 680 |     |     |     |     | 685 |     |     |     | 690 |     |
| Ala | Asp | Ser | Ile | Leu | Val | Lys | Trp | Glu | Asp | Ile | Pro | Val | Glu | Glu | Leu |
|     |     |     | 695 |     |     |     | 700 |     |     |     | 705 |     |     |
| Arg | Gly | Phe | Leu | Arg | Gly | Tyr | Leu | Phe | Tyr | Phe | Gly | Lys | Gly | Glu | Arg |
|     |     | 710 |     |     |     |     | 715 |     |     |     | 720 |     |     |
| Asp | Thr | Ser | Lys | Met | Arg | Val | Leu | Glu | Ser | Gly | Arg | Ser | Asp | Ile | Lys |
| 730 |     |     |     |     | 735 |     |     |     | 740 |     |     |     |     |
| Val | Lys | Asn | Ile | Thr | Asp | Ile | Ser | Gln | Lys | Thr | Leu | Arg | Ile | Ala | Asp |
|     |     |     | 745 |     |     |     | 750 |     |     |     |     | 755 |
| Leu | Gln | Gly | Lys | Thr | Ser | Tyr | His | Leu | Val | Leu | Arg | Ala | Tyr | Thr | Asp |
|     |     |     | 760 |     |     |     | 765 |     |     |     | 770 |     |     |
| Gly | Gly | Val | Gly | Pro | Glu | Lys | Ser | Met | Tyr | Val | Val | Thr | Lys | Glu | Asn |
|     |     |     | 775 |     |     |     | 780 |     |     |     | 785 |     |     |
| Ser | Val | Gly | Leu | Ile | Ile | Ala | Ile | Leu | Ile | Pro | Val | Ala | Val | Ala | Val |
|     | 790 |     |     |     |     | 795 |     |     |     | 800 |     |     |     |

```
Ile  Val  Gly  Val  Val  Thr  Ser  Ile  Leu  Cys  Tyr  Arg  Lys  Arg  Glu  Trp
810                 815                      820

Ile  Lys  Glu  Thr  Phe  Tyr  Pro  Asn  Ile  Pro  Asn  Pro  Glu  Asn  Cys  Lys
                    825                 830                           835

Ala  Leu  Gln  Phe  Gln  Lys  Ser  Val  Cys  Glu  Gly  Ser  Ser  Ala  Leu  Lys
                    840                 845                      850

Thr  Leu  Glu  Met  Asn  Pro  Cys  Thr  Pro  Asn  Asn  Val  Glu  Val  Leu  Glu
          855                      860                      865

Thr  Arg  Ser  Ala  Phe  Pro  Lys  Ile  Glu  Asp  Thr  Glu  Ile  Ile  Ser  Pro
     870                      875                 880

Val  Ala  Glu  Arg  Pro  Glu  Asp  Arg  Ser  Asp  Ala  Glu  Pro  Glu  Asn  His
885                      890                 895                           900

Val  Val  Val  Ser  Tyr  Cys  Pro  Pro  Ile  Ile  Glu  Glu  Glu  Ile  Pro  Asn
                    905                      910                      915

Pro  Ala  Ala  Asp  Glu  Ala  Gly  Gly  Thr  Ala  Gln  Val  Ile  Tyr  Ile  Asp
               920                      925                      930

Val  Gln  Ser  Met  Tyr  Gln  Pro  Gln  Ala  Lys  Pro  Glu  Glu  Lys  Lys  Lys
          935                      940                 945

Lys  Ser  Arg  Ser  Ser  Arg  Ser  Lys  Ile
950                      955
```

( 2 ) INFORMATION FOR SEQ ID NO:3:

( i ) SEQUENCE CHARACTERISTICS:
    ( A ) LENGTH: 2498 base pairs
    ( B ) TYPE: nucleic acid
    ( C ) STRANDEDNESS: single
    ( D ) TOPOLOGY: linear ( i i ) MOLECULE TYPE: CDNA to mRNA ( i i i ) HYPOTHETICAL: N ( i v ) ANTISENSE: N ( v i i ) IMMEDIATE SOURCE:
    ( B ) CLONE: mulifr3

( i x ) FEATURE:
    ( A ) NAME/KEY: CDS
    ( B ) LOCATION: 532212
    ( D ) OTHER INFORMATION:

( i x ) FEATURE:
    ( A ) NAME/KEY: matpeptide
    ( B ) LOCATION: 1822209
    ( D ) OTHER INFORMATION:

( i x ) FEATURE:
    ( A ) NAME/KEY: sigpeptide
    ( B ) LOCATION: 53181
    ( D ) OTHER INFORMATION:

( x i ) SEQUENCE DESCRIPTION: SEQ ID NO:3:

```
CCCCCTCCGT  GGCATTGGCT  CCTGCCCAGG  GGCTGACTGA  ACAGCAAGGA  CA ATG            55
                                                              Met
                                                              -43

GCA  GCT  TAC  TCA  TGG  TGG  AGA  CAG  CCA  TCG  TGG  ATG  GTA  GAC  AAT  AAA   103
Ala  Ala  Tyr  Ser  Trp  Trp  Arg  Gln  Pro  Ser  Trp  Met  Val  Asp  Asn  Lys
          -40                      -35                      -30

AGA  TCG  AGG  ATG  ACT  CCA  AAC  CTG  CCA  TGG  CTC  CTG  TCA  GCT  CTG  ACC   151
Arg  Ser  Arg  Met  Thr  Pro  Asn  Leu  Pro  Trp  Leu  Leu  Ser  Ala  Leu  Thr
     -25                      -20                      -15

CTC  CTG  CAT  CTG  ACG  ATG  CAT  GCA  AAC  GGT  CTG  AAG  AGA  GGG  GTA  CAA   199
Leu  Leu  His  Leu  Thr  Met  His  Ala  Asn  Gly  Leu  Lys  Arg  Gly  Val  Gln
-10                 -5                         1                    5
```

```
GAC TTG AAA TGC ACA ACC AAC AAC ATG CGA GTG TGG GAC TGC ACG TGG            247
Asp Leu Lys Cys Thr Thr Asn Asn Met Arg Val Trp Asp Cys Thr Trp
        10                  15                  20

CCA GCT CCC CTC GGG GTC AGC CCT GGA ACT GTT AAA GAT ATT TGC ATT            295
Pro Ala Pro Leu Gly Val Ser Pro Gly Thr Val Lys Asp Ile Cys Ile
            25                  30                  35

AAA GAC AGG TTC CAT TCT TGT CAC CCA TTA GAG ACA ACA AAC GTT AAA            343
Lys Asp Arg Phe His Ser Cys His Pro Leu Glu Thr Thr Asn Val Lys
        40                  45                  50

ATT CCA GCT CTT TCA CCT GGT GAT CAC GAA GTC ACA ATA AAT TAT CTA            391
Ile Pro Ala Leu Ser Pro Gly Asp His Glu Val Thr Ile Asn Tyr Leu
55                  60                  65                  70

AAT GGC TTT CAG AGT AAA TTC ACG TTG AAT GAA AAA GAT GTC TCT TTA            439
Asn Gly Phe Gln Ser Lys Phe Thr Leu Asn Glu Lys Asp Val Ser Leu
                75                  80                  85

ATT CCA GAG ACT CCC GAG ATC CTG GAT TTG TCT GCT GAC TTC TTC ACC            487
Ile Pro Glu Thr Pro Glu Ile Leu Asp Leu Ser Ala Asp Phe Phe Thr
            90                  95                  100

TCC TCC TTA CTA CTG AAG TGG AAC GAC AGA GGG TCT GCT CTG CCT CAC            535
Ser Ser Leu Leu Leu Lys Trp Asn Asp Arg Gly Ser Ala Leu Pro His
        105                 110                 115

CCC TCC AAT GCC ACC TGG GAG ATT AAG GTT CTA CAG AAT CCA AGG ACG            583
Pro Ser Asn Ala Thr Trp Glu Ile Lys Val Leu Gln Asn Pro Arg Thr
120                 125                 130

GAA CCA GTA GCA CTC GTG TTA CTC LAC ACA ATG CTG AGT GGT AAA GAT            631
Glu Pro Val Ala Leu Val Leu Leu Asn Thr Met Leu Ser Gly Lys Asp
135                 140                 145                 150

ACC GTT CAG CAC TGG AAC TGG ACC TCA GAC CTG CCC TTG CAA TGT GCC            679
Thr Val Gln His Trp Asn Trp Thr Ser Asp Leu Pro Leu Gln Cys Ala
                155                 160                 165

ACT CAC TCG GTG AGC ATT CGA TGG CAC ATT GAC TCG CCT CAT TTC TCC            727
Thr His Ser Val Ser Ile Arg Trp His Ile Asp Ser Pro His Phe Ser
            170                 175                 180

GGT TAC AAA GAG TGG AGT GAC TGG AGC CCG CTG LAG AAC ATC TCC TGG            775
Gly Tyr Lys Glu Trp Ser Asp Trp Ser Pro Leu Lys Asn Ile Ser Trp
        185                 190                 195

ATT CGT AAT ACA GAG ACT AAT GTT TTT CCT CAA GAC AAA GTG GTG CTC            823
Ile Arg Asn Thr Glu Thr Asn Val Phe Pro Gln Asp Lys Val Val Leu
    200                 205                 210

GCA GGC TCA AAC ATG ACA ATT TGT TGT ATG AGT CCA ACG AAA GTG CTT            871
Ala Gly Ser Asn Met Thr Ile Cys Cys Met Ser Pro Thr Lys Val Leu
215                 220                 225                 230

TCA GGA CAG ATC GGC AAT ACC CTT CGT CCT CTC ATC CAT CTG TAC GGG            919
Ser Gly Gln Ile Gly Asn Thr Leu Arg Pro Leu Ile His Leu Tyr Gly
                235                 240                 245

CAA ACC GTT GCG ATC CAT ATC CTG AAC ATC CCC GTT TCT GAA AAC AGT            967
Gln Thr Val Ala Ile His Ile Leu Asn Ile Pro Val Ser Glu Asn Ser
            250                 255                 260

GGC ACA AAC ATC ATT TTC ATC ACA GAC GAC GAT GTG TAC GGA ACG GTG           1015
Gly Thr Asn Ile Ile Phe Ile Thr Asp Asp Asp Val Tyr Gly Thr Val
        265                 270                 275

GTC TTT GCA GGC TAT CCT CCC GAT GTT CCT CAG AAG CTG AGC TGT GAG           1063
Val Phe Ala Gly Tyr Pro Pro Asp Val Pro Gln Lys Leu Ser Cys Glu
    280                 285                 290

ACA CAT GAC TTA AAA GAG ATT ATA TGT AGC TGG AAT CCA GGA AGG ATA           1111
Thr His Asp Leu Lys Glu Ile Ile Cys Ser Trp Asn Pro Gly Arg Ile
295                 300                 305                 310

ACT GGA CTG GTG GGC CCA CGA AAT ACA GAA TAC ACC CTG TTT GAA AGC           1159
Thr Gly Leu Val Gly Pro Arg Asn Thr Glu Tyr Thr Leu Phe Glu Ser
                315                 320                 325

ATT TCA GGA AAA TCG GCA GTA TAT CAC AGG ATT GAA GGA CTT ACA AAC           1207
Ile Ser Gly Lys Ser Ala Val Phe His Arg Ile Glu Gly Leu Thr Asn
```

-continued

| | | | | |
|---|---|---|---|---|
| | 330 | 335 | 340 | |
| GAG ACC TAC CGG TTA Glu Thr Tyr Arg Leu 345 | GGC GTG CAA ATG CAT Gly Val Gln Met His 350 | CCC GGC CAA GAA ATC CAT Pro Gly Gln Glu Ile His 355 | | 1255 |
| AAC TTC ACC CTG ACT Asn Phe Thr Leu Thr 360 | GGT CGC AAT CCA CTG Gly Arg Asn Pro Leu 365 | GGG CAG GCA CAG TCA GCA Gly Gln Ala Gln Ser Ala 370 | | 1303 |
| GTG GTC ATC AAT GTG Val Val Ile Asn Val 375 | ACT GAG AGA GTT GCT Thr Glu Arg Val Ala 380 | CCT CAT GAT CCG ACT TCG Pro His Asp Pro Thr Ser 385 390 | | 1351 |
| TTG AAA GTG AAG GAC Leu Lys Val Lys Asp | ATC AAT TCA ACA GTT Ile Asn Ser Thr Val | GTT ACA TTT TCT TGG TAT Val Thr Phe Ser Trp Tyr | | 1399 |
| | 395 | 400 | 405 | |
| TTA CCA GGA AAT TTT Leu Pro Gly Asn Phe | ACA AAG ATT AAT CTT Thr Lys Ile Asn Leu | TTA TGT CAA ATT GAA ATT Leu Cys Gln Ile Glu Ile | | 1447 |
| | 410 | 415 | 420 | |
| TGT ALA GCT AAT TCC Cys Lys Ala Asn Ser | AAG AAA GAA GTG AGG Lys Lys Glu Val Arg | AAT GCC ACA ATC AGA GGA Asn Ala Thr Ile Arg Gly | | 1495 |
| | 425 | 430 | 435 | |
| GCC GAG GAT TCA ACT Ala Glu Asp Ser Thr | TAC CAT GTT GCT GTA Tyr His Val Ala Val | GAC AAA TTA AAT CCA TAC Asp Lys Leu Asn Pro Tyr | | 1543 |
| | 440 | 445 | 450 | |
| ACT GCA TAC ACT TTC Thr Ala Tyr Thr Phe 455 | CGG GTT CGT TGT TCT Arg Val Arg Cys Ser 460 | TCC AAG ACT TTC TGG AAG Ser Lys Thr Phe Trp Lys 465 470 | | 1591 |
| TGG AGC AGG TGG AGT Trp Ser Arg Trp Ser | GAT GAG AAG CGA CAT Asp Glu Lys Arg His | CTA ACC ACA GAA GCC ACT Leu Thr Thr Glu Ala Thr | | 1639 |
| | 475 | 490 | 485 | |
| CCT TCA AAG GGA CCA Pro Ser Lys Gly Pro | GAC ACT TGG AGA GAG Asp Thr Trp Arg Glu | TGG AGT TCT GAT GGA AAA Trp Ser Ser Asp Gly Lys | | 1687 |
| | 490 | 495 | 500 | |
| AAT CTA ATC GTC TAC Asn Leu Ile Val Tyr | TGG AAG CCT TTA CCT Trp Lys Pro Leu Pro | ATT AAT GAA GCT AAT GGA Ile Asn Glu Ala Asn Gly | | 1735 |
| | 505 | 510 | 515 | |
| AAA ATA CTT TCC TAC Lys Ile Leu Ser Tyr | AAT GTT TCG TGT TCA Asn Val Ser Cys Ser | TTG AAC GAG GAG ACA CAG Leu Asn Glu Glu Thr Gln | | 1783 |
| | 520 | 525 | 530 | |
| TCA GTT TTG GAG ATC Ser Val Leu Glu Ile 535 | TTC GAT CCT CAA CAC Phe Asp Pro Gln His 540 | AGA GCA GAG ATA CAG CTT Arg Ala Glu Ile Gln Leu 545 550 | | 1831 |
| AGT AAA AAT GAC TAC Ser Lys Asn Asp Tyr | ATC ATC AGT GTG GTG Ile Ile Ser Val Val | GCA AGA AAT TCT GCT GGC Ala Arg Asn Ser Ala Gly | | 1879 |
| | 555 | 560 | 565 | |
| TCA TCA CCA CCT TCG Ser Ser Pro Pro Ser | AAA ATA GCT AGT ATG Lys Ile Ala Ser Met | GAA ATC CCA AAT GAC GAC Glu Ile Pro Asn Asp Asp | | 1927 |
| | 570 | 575 | 580 | |
| ATC ACA GTA GAG CAA Ile Thr Val Glu Gln | GCG GTG GGG CTA GGA Ala Val Gly Leu Gly | AAC ACG ATC TTC CTC ACC Asn Thr Ile Phe Leu Thr | | 1975 |
| | 585 | 590 | 595 | |
| TGG CGT CAC GAC CCC Trp Arg His Asp Pro 600 | AAC ATG ACT TGT GAC Asn Met Thr Cys Asp 605 | TAC GTA ATT AAA TGG TCC Tyr Val Ile Lys Trp Cys 610 | | 2023 |
| AAC TCA TCT CGG TCT Asn Ser Ser Arg Ser 620 | GAG CCC TGC CTC CTG Glu Pro Cys Leu Leu 625 | GAC TGG AGA AAG GTT CCT Asp Trp Arg Lys Val Pro 630 | | 2071 |
| TCA LAC AGC ACG GAG Ser Asn Ser Thr Glu | ACT GTC ATA GAG TCT Thr Val Ile Glu Ser | GAT CAG TTT CAG CCA GGA Asp Gln Phe Gln Pro Gly | | 2119 |
| | 635 | 640 | 645 | |
| GTA AGA TAC AAC TTT Val Arg Tyr Asn Phe | TAC CTC TAT GGG TGC Tyr Leu Tyr Gly Cys | ACT AAC CAG CGA TAC CAA Thr Asn Gln Arg Tyr Gln | | 2167 |
| | 650 | 655 | 660 | |

| | |
|---|---|
| CTG TTA CGT TCC ATA ATT GGA TAC GTA GAA GAA CTG GAA GCT TAA<br>Leu Leu Arg Ser Ile Ile Gly Tyr Val Glu Glu Leu Glu Ala<br>665   670   675 | 2212 |
| AAACTTGGAA ATGTATCCAG GCCTAACACC AGAGAGGGGA GTATCCCTGA AGTCTGTTTG | 2272 |
| AGCGGTCACT TAAAATATGC GGCACATGGG GGGCTGGAGA GAAGGCACCG ACTGCTCTTC | 2332 |
| CAGAGGTCCT GAGTTCAATT CCCAGCAACC ACATGGTGAC TCACAACCAT CTGTAATGGG | 2392 |
| GTCTGGTGCC CTCTTCTGGT GTGTCTGAAG AGAGCAATGG TGGCATACTC ATATGTATAA | 2452 |
| AATAAATAAA TAAAACTTTT TAAAAAACCA AAAAAAAAA AAAAAA | 2498 |

( 2 ) INFORMATION FOR SEQ ID NO:4:

( i ) SEQUENCE CHARACTERISTICS:
  ( A ) LENGTH: 719 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

```
Met Ala Ala Tyr Ser Trp Trp Arg Gln Pro Ser Try Met Val Asp Asn
-43         -40                 -35                 -30

Lys Arg Ser Arg Met Thr Pro Asn Leu Pro Trp Leu Leu Ser Ala Leu
        -25                 -20                 -15

Thr Leu Leu His Leu Thr Met His Ala Asn Gly Leu Lys Arg Gly Val
    -10                  -5                   1                 5

Gln Asp Leu Lys Cys Thr Thr Asn Asn Met Arg Val Tro Asp Cys Thr
                10                 15                 20

Trp Pro Ala Pro Leu Gly Val Ser Pro Gly Thr Val Lys Asp Ile Cys
            25                 30                 35

Ile Lys Asp Arg Phe His Ser Cys His Pro Leu Glu Thr Thr Asn Val
        40                 45                 50

Lys Ile Pro Ala Leu Ser Pro Gly Asp His Glu Val Thr Ile Asn Tyr
    55                 60                 65

Leu Asn Gly Phe Gln Ser Lys Phe Thr Leu Asn Glu Lys Asp Val Ser
70                 75                 80                 85

Leu Ile Pro Glu Thr Pro Glu Ile Leu Asp Leu Ser Ala Asp Phe Phe
            90                 95                 100

Thr Ser Ser Leu Leu Leu Lys Trp Asn Asp Arg Gly Ser Ala Leu Pro
                105                110                115

His Pro Ser Asn Ala Thr Trp Glu Ile Lys Val Leu Gln Asn Pro Arg
        120                125                130

Thr Glu Pro Val Ala Leu Val Leu Leu Asn Thr Met Leu Ser Gly Lys
    135                140                145

Asp Thr Val Gln His Trp Asn Trp Thr Ser Asp Leu Pro Leu Gln Cys
150                155                160                165

Ala Thr His Ser Val Ser Ile Arg Trp His Ile Asn Ser Pro His Phe
            170                175                180

Ser Gly Tyr Lys Glu Trp Ser Asp Trp Ser Pro Leu Lys Asn Ile Ser
                185                190                195

Trp Ile Arg Asn Thr Glu Thr Asn Val Phe Pro Gln Asp Lys Val Val
        200                205                210

Leu Ala Gly Ser Asn Met Thr Ile Cys Cys Met Ser Pro Thr Lys Val
    215                220                225

Leu Ser Gly Gln Ile Gly Asn Thr Leu Arg Pro Leu Ile His Leu Tyr
230                235                240                245

Gly Gln Thr Val Ala Ile His Ile Leu Asn Ile Pro Val Ser Glu Asn
            250                255                260
```

-continued

| | | | | | | | | | | | | | |
|---|---|---|---|---|---|---|---|---|---|---|---|---|---|
|Ser|Gly|Thr|Asn 265|Ile|Ile|Phe|Ile Thr 270|Asp|Asp|Asp|Val Tyr 275|Gly|Thr|
|Val|Val|Phe 280|Ala|Gly|Tyr|Pro|Pro Asp 285|Val|Pro|Gln|Lys Leu 290|Ser|Cys|
|Glu|Thr 295|His|Asp|Leu|Lys|Glu 300|Ile Ile|Cys|Ser|Trp 305|Asn Pro|Gly|Arg|
|Ile 310|Thr|Gly|Leu|Val|Gly 315|Pro|Arg Asn|Thr|Glu 320|Tyr|Thr Leu|Phe|Glu 325|
|Ser|Ile|Ser|Gly|Lys 330|Ser|Ala|Val Phe|His 335|Arg|Ile|Glu Gly|Leu|Thr 340|
|Asn|Glu|Thr|Tyr 345|Arg|Leu|Gly|Val Gln 350|Met|His|Pro|Gly Gln 355|Glu|Ile|
|His|Asn|Phe 360|Thr|Leu|Thr|Gly|Arg Asn 365|Pro|Leu|Gly|Gln Ala 370|Gln|Ser|
|Ala|Val 375|Val|Ile|Asn|Val|Thr 380|Glu Arg|Val|Ala|Pro 385|His Asp|Pro|Thr|
|Ser 390|Leu|Lys|Val|Lys|Asp 395|Ile|Asn Ser|Thr|Val 400|Val|Thr Phe|Ser|Trp 405|
|Tyr|Leu|Pro|Gly|Asn 410|Phe|Thr|Lys Ile|Asn 415|Leu|Leu|Cys Gln|Ile|Glu 420|
|Ile|Cys|Lys|Ala 425|Asn|Ser|Lys|Lys Glu 430|Val|Arg|Asn|Ala Thr 435|Ile|Arg|
|Gly|Ala|Glu 440|Asp|Ser|Thr|Tyr|His Val 445|Ala|Val|Asp|Lys Leu 450|Asn|Pro|
|Tyr|Thr 455|Ala|Tyr|Thr|Phe|Arg 460|Val Arg|Cys|Ser|Ser 465|Lys Thr|Phe|Trp|
|Lys 470|Trp|Ser|Arg|Trp|Ser 475|Asp|Glu Lys|Arg|His 480|Leu|Thr Thr|Glu|Ala 485|
|Thr|Pro|Ser|Lys|Gly 490|Pro|Asp|Thr Trp|Arg 495|Glu|Trp|Ser Ser|Asp 500|Gly|
|Lys|Asn|Leu|Ile 505|Val|Tyr|Trp|Lys Pro 510|Leu|Pro|Ile|Asn Glu 515|Ala|Asn|
|Gly|Lys|Ile 520|Leu|Ser|Tyr|Asn|Val Ser 525|Cys|Ser|Leu|Asn Glu 530|Glu|Thr|
|Gln|Ser 535|Val|Leu|Glu|Ile|Phe 540|Asn Pro|Gln|His|Arg 545|Ala Glu|Ile|Gln|
|Leu 550|Ser|Lys|Asn|Asp|Tyr 555|Ile|Ile Ser|Val|Val 560|Ala|Arg Asn|Ser|Ala 565|
|Gly|Ser|Ser|Pro|Pro 570|Ser|Lys|Ile Ala|Ser 575|Met|Glu|Ile Pro|Asn 580|Asp|
|Asp|Ile|Thr|Val 585|Glu|Gln|Ala|Val Gly 590|Leu|Gly|Asn|Arg Ile 595|Phe|Leu|
|Thr|Trp|Arg 600|His|Asp|Pro|Asn|Met Thr 605|Cys|Asp|Tyr|Val Ile 610|Lys|Trp|
|Cys|Asn 615|Ser|Ser|Arg|Ser|Glu 620|Pro Cys|Leu|Leu|Asp 625|Trp Arg|Lys|Val|
|Pro 630|Ser|Asn|Ser|Thr|Glu 635|Thr|Val Ile|Glu|Ser 640|Asp|Gln Phe|Gln|Pro 645|
|Gly|Val|Arg|Tyr|Asn 650|Phe|Tyr|Leu Tyr|Gly 655|Cys|Thr|Asn Gln|Gly 660|Tyr|
|Gln|Leu|Leu|Arg 665|Ser|Ile|Ile|Gly Tyr 670|Val|Glu|Glu|Leu Glu 675|Ala| |

( 2 ) INFORMATION FOR SEQ ID NO:5:

( i ) SEQUENCE CHARACTERISTICS:

(A) LENGTH: 3591 base pairs
(B) TYPE: nucleic acid
(C) STRANDEDNESS: single
(D) TOPOLOGY: linear (ii) MOLECULE TYPE: cDNA to mRNA (iii) HYPOTHETICAL: NO (iv) ANTISENSE: NO (vii) IMMEDIATE SOURCE:
    (B) CLONE: hulifr.65- gen (ix) FEATURE:
    (A) NAME/KEY: CDS
    (B) LOCATION: 179..3492

(ix) FEATURE:
    (A) NAME/KEY: matpeptide
    (B) LOCATION: 311..3469

(ix) FEATURE:
    (A) NAME/KEY: sigpeptide
    (B) LOCATION: 179..310

(xi) SEQUENCE DESCRIPTION: SEQ ID NO:5:

```
AGATCTTGGA ACGAGACGAC CTGCTCTCTC TCCCAGAACG TGTCTCTGCT GCAAGGCACC     60

GGGCCCTTTC GCTCTGCAGA ACTGCACTTG CAAGACCATT ATCAACTCCT AATCCCAGCT    120

CAGAAAGGGA GCCTCTGCGA CTCATTCATC GCCCTCCAGG ACTGACTGCA TTGCACAG      178

ATG ATG GAT ATT TAC GTA TGT TTG AAA CGA CCA TCC TGG ATG GTG GAC     226
Met Met Asp Ile Tyr Val Cys Leu Lys Arg Pro Ser Trp Met Val Asp
-44         -40                 -35                 -30

AAT AAA AGA ATG AGG ACT GCT TCA AAT TTC CAG TGG CTG TTA TCA ACA     274
Asn Lys Arg Met Arg Thr Ala Ser Asn Phe Gln Trp Leu Leu Ser Thr
            -25                 -20                 -15

TTT ATT CTT CTA TAT CTA ATG AAT CAA GTA AAT AGC CAG AAA AAG GGG     322
Phe Ile Leu Leu Tyr Leu Met Asn Gln Val Asn Ser Gln Lys Lys Gly
        -10                 -5                   1

GCT CCT CAT GAT TTG AAG TGT GTA ACT AAC AAT TTG CAA GTG TGG AAC     370
Ala Pro His Asp Leu Lys Cys Val Thr Asn Asn Leu Gln Val Trp Asn
  5                10                  15                  20

TGT TCT TGG AAA GCA CCC TCT GGA ACA GGC CGT GGT ACT GAT TAT GAA     418
Cys Ser Trp Lys Ala Pro Ser Gly Thr Gly Arg Gly Thr Asp Tyr Glu
              25                  30                  35

GTT TGC ATT GAA AAC AGG TCC CGT TCT TGT TAT CAG TTG GAG AAA ACC     466
Val Cys Ile Glu Asn Arg Ser Arg Ser Cys Tyr Gln Leu Glu Lys Thr
              40                  45                  50

AGT ATT AAA ATT CCA GCT CTT TCA CAT GGT GAT TAT GAA ATA ACA ATA     514
Ser Ile Lys Ile Pro Ala Leu Ser His Gly Asp Tyr Glu Ile Thr Ile
          55                  60                  65

AAT TCT CTA CAT GAT TTT GGA AGT TCT ACA AGT AAA TTC ACA CTA AAT     562
Asn Ser Leu His Asp Phe Gly Ser Ser Thr Ser Lys Phe Thr Leu Asn
      70                  75                  80

GAA CAA AAC GTT TCC TTA ATT CCA GAT ACT CCA GAG ATC TTG AAT TTG     610
Glu Gln Asn Val Ser Leu Ile Pro Asp Thr Pro Glu Ile Leu Asn Leu
 85                  90                  95                 100

TCT GCT GAT TTC TCA ACC TCT ACA TTA TAC CTA AAG TGG AAC GAC AGG     658
Ser Ala Asp Phe Ser Thr Ser Thr Leu Tyr Leu Lys Trp Asn Asp Arg
                    105                 110                 115

GGT TCA GTT TTT CCA CAC CGC TCA AAT GTT ATC TGG GAA ATT AAA GTT     706
Gly Ser Val Phe Pro His Arg Ser Asn Val Ile Trp Glu Ile Lys Val
                120                 125                 130

CTA CGT AAA GAG AGT ATG GAG CTC GTA AAA TTA GTG ACC CAC AAC ACA     754
Leu Arg Lys Glu Ser Met Glu Leu Val Lys Leu Val Thr His Asn Thr
            135                 140                 145
```

| | | | | | | | | | | | | | | | | |
|---|---|---|---|---|---|---|---|---|---|---|---|---|---|---|---|---|
| ACT | CTG | AAT | GGC | AAA | GAT | ACA | CTT | CAT | CAC | TGG | AGT | TGG | GCC | TCA | GAT | 802 |
| Thr | Leu | Asn | Gly | Lys | Asp | Thr | Leu | His | His | Trp | Ser | Trp | Ala | Ser | Asp | |
| | | 150 | | | | | 155 | | | | | 160 | | | | |
| ATG | CCC | TTG | GAA | TGT | GCC | ATT | CAT | TTT | GTG | GAA | ATT | AGA | TGC | TAC | ATT | 850 |
| Met | Pro | Leu | Glu | Cys | Ala | Ile | His | Phe | Val | Glu | Ile | Arg | Cys | Tyr | Ile | |
| 165 | | | | 170 | | | | | 175 | | | | | 180 | | |
| GAC | AAT | CTT | CAT | TTT | TCT | GGT | CTC | GAA | GAG | TGG | AGT | GAC | TGG | AGC | CCT | 898 |
| Asp | Asn | Leu | His | Phe | Ser | Gly | Leu | Glu | Glu | Trp | Ser | Asp | Trp | Ser | Pro | |
| | | | | 185 | | | | | 190 | | | | | 195 | | |
| GTG | AAG | AAC | ATT | TCT | TGG | ATA | CCT | GAT | TCT | CAG | ACT | AAG | GTT | TTT | CCT | 946 |
| Val | Lys | Asn | Ile | Ser | Trp | Ile | Pro | Asp | Ser | Gln | Thr | Lys | Val | Phe | Pro | |
| | | | 200 | | | | | 205 | | | | | 210 | | | |
| CAA | GAT | AAA | GTG | ATA | CTT | GTA | GGC | TCA | GAC | ATA | ACA | TTT | TGT | TGT | GTG | 994 |
| Gln | Asp | Lys | Val | Ile | Leu | Val | Gly | Ser | Asp | Ile | Thr | Phe | Cys | Cys | Val | |
| | | 215 | | | | | 220 | | | | | 225 | | | | |
| AGT | CAA | GAA | AAA | GTG | TTA | TCA | GCA | CTG | ATT | GGC | CAT | ACA | AAC | TGC | CCC | 1042 |
| Ser | Gln | Glu | Lys | Val | Leu | Ser | Ala | Leu | Ile | Gly | His | Thr | Asn | Cys | Pro | |
| | 230 | | | | | 235 | | | | | 240 | | | | | |
| TTG | ATC | CAT | CTT | GAT | GGG | GAA | AAT | GTT | GCA | ATC | AAG | ATT | CGT | AAT | ATT | 1090 |
| Leu | Ile | His | Leu | Asp | Gly | Glu | Asn | Val | Ala | Ile | Lys | Ile | Arg | Asn | Ile | |
| 245 | | | | | 250 | | | | | 255 | | | | | 260 | |
| TCT | GTT | TCT | GCA | AGT | AGT | GGA | ACA | AAT | GTA | GTT | TTT | ACA | ACC | GAA | GAT | 1138 |
| Ser | Val | Ser | Ala | Ser | Ser | Gly | Thr | Asn | Val | Val | Phe | Thr | Thr | Glu | Asp | |
| | | | | 265 | | | | | 270 | | | | | 275 | | |
| AAC | ATA | TTT | GGA | ACC | GTT | ATT | TTT | GCT | GGA | TAT | CCA | CCA | GAT | ACT | CCT | 1186 |
| Asn | Ile | Phe | Gly | Thr | Val | Ile | Phe | Ala | Gly | Tyr | Pro | Pro | Asp | Thr | Pro | |
| | | | 280 | | | | | 285 | | | | | 290 | | | |
| CAA | CAA | CTG | AAT | TGT | GAG | ACA | CAT | GAT | TTA | AAA | GAA | ATT | ATA | TGT | AGT | 1234 |
| Gln | Gln | Leu | Asn | Cys | Glu | Thr | His | Asp | Leu | Lys | Glu | Ile | Ile | Cys | Ser | |
| | | 295 | | | | | 300 | | | | | 305 | | | | |
| TGG | AAT | CCA | GGA | AGG | GTG | ACA | GCG | TTG | GTG | GGC | CCA | CGT | GCT | ACA | AGC | 1282 |
| Trp | Asn | Pro | Gly | Arg | Val | Thr | Ala | Leu | Val | Gly | Pro | Arg | Ala | Thr | Ser | |
| | 310 | | | | | 315 | | | | | 320 | | | | | |
| TAC | ACT | TTA | GTT | GAA | AGT | TTT | TCA | GGA | AAA | TAT | GTT | AGA | CTT | AAA | AGA | 1330 |
| Tyr | Thr | Leu | Val | Glu | Ser | Phe | Ser | Gly | Lys | Tyr | Val | Arg | Leu | Lys | Arg | |
| 325 | | | | | 330 | | | | | 335 | | | | | 340 | |
| GCT | GAA | GCA | CCT | ACA | AAC | GAA | AGC | TAT | CAA | TTA | TTA | TTT | CAA | ATG | CTT | 1378 |
| Ala | Glu | Ala | Pro | Thr | Asn | Glu | Ser | Tyr | Gln | Leu | Leu | Phe | Gln | Met | Leu | |
| | | | | 345 | | | | | 350 | | | | | 355 | | |
| CCA | AAT | CAA | GAA | ATA | TAT | AAT | TTT | ACT | TTG | AAT | GCT | CAC | AAT | CCG | CTG | 1426 |
| Pro | Asn | Gln | Glu | Ile | Tyr | Asn | Phe | Thr | Leu | Asn | Ala | His | Asn | Pro | Leu | |
| | | | 360 | | | | | 365 | | | | | 370 | | | |
| GGT | CGA | TCA | CAA | TCA | ACA | ATT | TTA | GTT | AAT | ATA | ACT | GAA | AAA | GTT | TAT | 1474 |
| Gly | Arg | Ser | Gln | Ser | Thr | Ile | Leu | Val | Asn | Ile | Thr | Glu | Lys | Val | Tyr | |
| | | 375 | | | | | 380 | | | | | 385 | | | | |
| CCC | CAT | ACT | CCT | ACT | TCA | TTC | AAA | GTG | AAG | GAT | ATT | AAT | TCA | ACA | GCT | 1522 |
| Pro | His | Thr | Pro | Thr | Ser | Phe | Lys | Val | Lys | Asp | Ile | Asn | Ser | Thr | Ala | |
| | 390 | | | | | 395 | | | | | 400 | | | | | |
| GTT | AAA | CTT | TCT | TGG | CAT | TTA | CCA | GGC | AAC | TTT | GCA | AAG | ATT | AAT | TTT | 1570 |
| Val | Lys | Leu | Ser | Trp | His | Leu | Pro | Gly | Asn | Phe | Ala | Lys | Ile | Asn | Phe | |
| 405 | | | | | 410 | | | | | 415 | | | | | 420 | |
| TTA | TGT | GAA | ATT | GAA | ATT | AAG | AAA | TCT | AAT | TCA | GTA | CAA | GAG | CAG | CGG | 1618 |
| Leu | Cys | Glu | Ile | Glu | Ile | Lys | Lys | Ser | Asn | Ser | Val | Gln | Glu | Gln | Arg | |
| | | | | 425 | | | | | 430 | | | | | 435 | | |
| AAT | GTC | ACA | ATC | AAA | GGA | GTA | GAA | AAT | TCA | AGT | TAT | CTT | GTT | GCT | CTG | 1666 |
| Asn | Val | Thr | Ile | Lys | Gly | Val | Glu | Asn | Ser | Ser | Tyr | Leu | Val | Ala | Leu | |
| | | | 440 | | | | | 445 | | | | | 450 | | | |
| GAC | AAG | TTA | AAT | CCA | TAC | ACT | CTA | TAT | ACT | TTT | CGG | ATT | CGT | TGT | TCT | 1714 |
| Asp | Lys | Leu | Asn | Pro | Tyr | Thr | Leu | Tyr | Thr | Phe | Arg | Ile | Arg | Cys | Ser | |
| | | 455 | | | | | 460 | | | | | 465 | | | | |
| ACT | GAA | ACT | TTC | TGG | AAA | TGG | AGC | AAA | TGG | AGC | AAT | AAA | AAA | CAA | CAT | 1762 |
| Thr | Glu | Thr | Phe | Trp | Lys | Trp | Ser | Lys | Trp | Ser | Asn | Lys | Lys | Gln | His | |

-continued

| | | | | | | | | | | | | | | | | |
|---|---|---|---|---|---|---|---|---|---|---|---|---|---|---|---|---|
| | | | 470 | | | | | 475 | | | | | 480 | | | |
| TTA | ACA | ACA | GAA | GCC | AGT | CCT | TCA | AAG | GGG | CCT | GAT | ACT | TGG | AGA | GAG | 1810 |
| Leu | Thr | Thr | Glu | Ala | Ser | Pro | Ser | Lys | Gly | Pro | Asp | Thr | Trp | Arg | Glu | |
| 485 | | | | 490 | | | | | 495 | | | | | 500 | | |
| TGG | AGT | TCT | GAT | GGA | AAA | AAT | TTA | ATA | ATC | TAT | TGG | AAG | CCT | TTA | CCC | 1858 |
| Trp | Ser | Ser | Asp | Gly | Lys | Asn | Leu | Ile | Ile | Tyr | Trp | Lys | Pro | Leu | Pro | |
| | | | | 505 | | | | | 510 | | | | | 515 | | |
| ATT | AAT | GAA | GCT | AAT | GGA | AAA | ATA | CTT | TCC | TAC | AAT | GTA | TCG | TGT | TCA | 1906 |
| Ile | Asn | Glu | Ala | Asn | Gly | Lys | Ile | Leu | Ser | Tyr | Asn | Val | Ser | Cys | Ser | |
| | | | | 520 | | | | | 525 | | | | | 530 | | |
| TCA | GAT | GAG | GAA | ACA | CAG | TCC | CTT | TCT | GAA | ATC | CCT | GAT | CCT | CAG | CAC | 1954 |
| Ser | Asp | Glu | Glu | Thr | Gln | Ser | Leu | Ser | Glu | Ile | Pro | Asp | Pro | Gln | His | |
| | | 535 | | | | | 540 | | | | | 545 | | | | |
| AAA | GCA | GAG | ATA | CGA | CTT | GAT | AAG | AAT | GAC | TAC | ATC | ATC | AGC | GTA | GTG | 2002 |
| Lys | Ala | Glu | Ile | Arg | Leu | Asp | Lys | Asn | Asp | Tyr | Ile | Ile | Ser | Val | Val | |
| | 550 | | | | | 555 | | | | | 560 | | | | | |
| GCT | AAA | AAT | TCT | GTG | GGC | TCA | TCA | CCA | CCT | TCC | AAA | ATA | GCG | AGT | ATG | 2050 |
| Ala | Lys | Asn | Ser | Val | Gly | Ser | Ser | Pro | Pro | Ser | Lys | Ile | Ala | Ser | Met | |
| 565 | | | | | 570 | | | | | 575 | | | | | 580 | |
| GAA | ATT | CCA | AAT | GAT | GAT | CTC | AAA | ATA | GAA | CAA | GTT | GTT | GGG | ATG | GGA | 2098 |
| Glu | Ile | Pro | Asn | Asp | Asp | Leu | Lys | Ile | Glu | Gln | Val | Val | Gly | Met | Gly | |
| | | | | 585 | | | | | 590 | | | | | 595 | | |
| AAG | GGG | ATT | CTC | CTC | ACC | TGG | CAT | TAC | GAC | CCC | AAC | ATG | ACT | TGC | GAC | 2146 |
| Lys | Gly | Ile | Leu | Leu | Thr | Trp | His | Tyr | Asp | Pro | Asn | Met | Thr | Cys | Asp | |
| | | | 600 | | | | | 605 | | | | | 610 | | | |
| TAC | GTC | ATT | AAG | TGG | TGT | AAC | TCG | TCT | CGG | TCG | GAA | CCA | TGC | CTT | ATG | 2194 |
| Tyr | Val | Ile | Lys | Trp | Cys | Asn | Ser | Ser | Arg | Ser | Glu | Pro | Cys | Leu | Met | |
| | | 615 | | | | | 620 | | | | | 625 | | | | |
| GAC | TGG | AGA | ALA | GTT | CCC | TCA | AAC | AGC | ACT | GAA | ACT | GTA | ATA | GAA | TCT | 2242 |
| Asp | Trp | Arg | Lys | Val | Pro | Ser | Asn | Ser | Thr | Glu | Thr | Val | Ile | Glu | Ser | |
| | 630 | | | | | 635 | | | | | 640 | | | | | |
| CAT | GAG | TTT | CGA | CCA | GGT | ATA | AGA | TAT | AAT | TTT | TTC | CTG | TAT | GGA | TGC | 2290 |
| Asp | Glu | Phe | Arg | Pro | Gly | Ile | Arg | Tyr | Asn | Phe | Phe | Leu | Tyr | Gly | Cys | |
| 645 | | | | | 650 | | | | | 655 | | | | | 660 | |
| AGA | AAT | CAA | GGA | TAT | CAA | TTA | TTA | CGC | TCC | ATG | ATT | GGA | TAT | ATA | GAA | 2338 |
| Arg | Asn | Gln | Gly | Tyr | Gln | Leu | Leu | Arg | Ser | Met | Ile | Gly | Tyr | Ile | Glu | |
| | | | | 665 | | | | | 670 | | | | | 675 | | |
| GAA | TTG | GCT | CCC | ATT | GTT | GCA | CCA | AAT | TTT | ACT | GTT | GAG | GAT | ACT | TCT | 2386 |
| Glu | Leu | Ala | Pro | Ile | Val | Ala | Pro | Asn | Phe | Thr | Val | Glu | Asp | Thr | Ser | |
| | | | 680 | | | | | 685 | | | | | 690 | | | |
| GCA | GAT | TCG | ATA | TTA | GTA | AAA | TGG | GAA | GAC | ATT | CCT | GTG | GAA | GAA | CTT | 2434 |
| Ala | Asp | Ser | Ile | Leu | Val | Lys | Trp | Glu | Asp | Ile | Pro | Val | Glu | Glu | Leu | |
| | | 695 | | | | | 700 | | | | | 705 | | | | |
| AGA | GGC | TTT | TTA | AGA | GGA | TAT | TTG | TTT | TAC | TTT | GGA | AAA | GGA | GAA | AGA | 2482 |
| Arg | Gly | Phe | Leu | Arg | Gly | Tyr | Leu | Phe | Tyr | Phe | Gly | Lys | Gly | Glu | Arg | |
| | 710 | | | | | 715 | | | | | 720 | | | | | |
| GAC | ACA | TCT | AAG | ATG | AGG | GTT | TTA | GAA | TCA | GGT | CGT | TCT | GAC | ATA | AAA | 2530 |
| Asp | Thr | Ser | Lys | Met | Arg | Val | Leu | Glu | Ser | Gly | Arg | Ser | Asp | Ile | Lys | |
| 725 | | | | | 730 | | | | | 735 | | | | | 740 | |
| GTT | AAG | AAT | ATT | ACT | GAC | ATA | TCC | CAG | AAG | ACA | CTG | AGA | ATT | GCT | GAT | 2578 |
| Val | Lys | Asn | Ile | Thr | Asp | Ile | Ser | Gln | Lys | Thr | Leu | Arg | Ile | Ala | Asp | |
| | | | | 745 | | | | | 750 | | | | | 755 | | |
| CTT | CAA | GGT | AAA | ACA | AGT | TAC | CAC | CTG | GTC | TTG | CGA | GCC | TAT | ACA | GAT | 2626 |
| Leu | Gln | Gly | Lys | Thr | Ser | Tyr | His | Leu | Val | Leu | Arg | Ala | Tyr | Thr | Asp | |
| | | | 760 | | | | | 765 | | | | | 770 | | | |
| GGT | GGA | GTG | GGC | CCG | GAG | AAG | AGT | ATG | TAT | GTG | GTG | ACA | AAG | GAA | AAT | 2674 |
| Gly | Gly | Val | Gly | Pro | Glu | Lys | Ser | Met | Tyr | Val | Val | Thr | Lys | Glu | Asn | |
| | | 775 | | | | | 780 | | | | | 785 | | | | |
| TCT | GTG | GGA | TTA | ATT | ATT | GCC | ATT | CTC | ATC | CCA | GTG | GCA | GTG | GCT | GTC | 2722 |
| Ser | Val | Gly | Leu | Ile | Ile | Ala | Ile | Leu | Ile | Pro | Val | Ala | Val | Ala | Val | |
| | 790 | | | | | 795 | | | | | 800 | | | | | |

| | | | | | | | | | | | | | | | | |
|---|---|---|---|---|---|---|---|---|---|---|---|---|---|---|---|---|
| ATT | GTT | GGA | GTG | GTG | ACA | AGT | ATC | CTT | TGC | TAT | CGG | AAA | CGA | GAA | TGG | 2770 |
| Ile | Val | Gly | Val | Val | Thr | Ser | Ile | Leu | Cys | Tyr | Arg | Lys | Arg | Glu | Trp | |
| 805 | | | | 810 | | | | | 815 | | | | | | 820 | |
| ATT | AAA | GAA | ACC | TTC | TAC | CCT | GAT | ATT | CCA | AAT | CCA | GAA | AAC | TGT | AAA | 2818 |
| Ile | Lys | Glu | Thr | Phe | Tyr | Pro | Asp | Ile | Pro | Asn | Pro | Glu | Asn | Cys | Lys | |
| | | | | 825 | | | | 830 | | | | | | 835 | | |
| GCA | TTA | CAG | TTT | CAA | AAG | AGT | GTC | TGT | GAG | GGA | AGC | AGT | GCT | CTT | AAA | 2866 |
| Ala | Leu | Gln | Phe | Gln | Lys | Ser | Val | Cys | Glu | Gly | Ser | Ser | Ala | Leu | Lys | |
| | | | 840 | | | | | 845 | | | | | 850 | | | |
| ACA | TTG | GAA | ATG | AAT | CCT | TGT | ACC | CCA | AAT | AAT | GTT | GAG | GTT | CTG | GAA | 2914 |
| Thr | Leu | Glu | Met | Asn | Pro | Cys | Thr | Pro | Asn | Asn | Val | Glu | Val | Leu | Glu | |
| | | 855 | | | | 860 | | | | | 865 | | | | | |
| ACT | CGA | TCA | GCA | TTT | CCT | AAA | ATA | GAA | GAT | ACA | GAA | ATA | ATT | TCC | CCA | 2962 |
| Thr | Arg | Ser | Ala | Phe | Pro | Lys | Ile | Glu | Asp | Thr | Glu | Ile | Ile | Ser | Pro | |
| | 870 | | | | 875 | | | | 880 | | | | | | | |
| GTA | GCT | GAG | CGT | CCT | GAA | GAT | CGC | TCT | GAT | GCA | GAG | CCT | GAA | AAC | CAT | 3010 |
| Val | Ala | Glu | Arg | Pro | Glu | Asp | Arg | Ser | Asp | Ala | Glu | Pro | Glu | Asn | His | |
| 885 | | | | 890 | | | | 895 | | | | | | | 900 | |
| GTG | GTT | GTG | TCC | TAT | TGT | CCA | CCC | ATC | ATT | GAG | GAA | GAA | ATA | CCA | AAC | 3058 |
| Val | Val | Val | Ser | Tyr | Cys | Pro | Pro | Ile | Ile | Glu | Glu | Glu | Ile | Pro | Asn | |
| | | | | 905 | | | | 910 | | | | | | 915 | | |
| CCA | GCC | GCA | GAT | GAA | GCT | GGA | GGG | ACT | GCA | CAG | GTT | ATT | TAC | ATT | GAT | 3106 |
| Pro | Ala | Ala | Asp | Glu | Ala | Gly | Gly | Thr | Ala | Gln | Val | Ile | Tyr | Ile | Asp | |
| | | | 920 | | | | | 925 | | | | | 930 | | | |
| GTT | CAG | TCG | ATG | TAT | CAG | CCT | CAA | GCA | AAA | CCA | GAA | GAA | GAA | CAA | GAA | 3154 |
| Val | Gln | Ser | Met | Tyr | Gln | Pro | Gln | Ala | Lys | Pro | Glu | Glu | Glu | Gln | Glu | |
| | | 935 | | | | | 940 | | | | | 945 | | | | |
| AAT | GAC | CCT | GTA | GGA | GGG | GCA | GGC | TAT | AAG | CCA | CAG | ATG | CAC | CTC | CCC | 3202 |
| Asn | Asp | Pro | Val | Gly | Gly | Ala | Gly | Tyr | Lys | Pro | Gln | Met | His | Leu | Pro | |
| | 950 | | | | | 955 | | | | | 960 | | | | | |
| ATT | AAT | TCT | ACT | GTG | GAA | GAT | ATA | GCT | GCA | GAA | GAG | GAC | TTA | GAT | AAA | 3250 |
| Ile | Asn | Ser | Thr | Val | Glu | Asp | Ile | Ala | Ala | Glu | Glu | Asp | Leu | Asp | Lys | |
| 965 | | | | | 970 | | | | 975 | | | | | | 980 | |
| ACT | GCG | GGT | TAC | AGA | CCT | CAG | GCC | AAT | GTA | AAT | ACA | TGG | AAT | TTA | GTG | 3298 |
| Thr | Ala | Gly | Tyr | Arg | Pro | Gln | Ala | Asn | Val | Asn | Thr | Trp | Asn | Leu | Val | |
| | | | | 985 | | | | | 990 | | | | | 995 | | |
| TCT | CCA | GAC | TCT | CCT | AGA | TCC | ATA | GAC | AGC | AAC | AGT | GAG | ATT | GTC | TCA | 3346 |
| Ser | Pro | Asp | Ser | Pro | Arg | Ser | Ile | Asp | Ser | Asn | Ser | Glu | Ile | Val | Ser | |
| | | | | 1000 | | | | 1005 | | | | | | 1010 | | |
| TTT | GGA | AGT | CCA | TGC | TCC | ATT | AAT | TCC | CGA | CAA | TTT | TTG | ATT | CCT | CCT | 3394 |
| Phe | Gly | Ser | Pro | Cys | Ser | Ile | Asn | Ser | Arg | Gln | Phe | Leu | Ile | Pro | Pro | |
| | | | 1015 | | | | | 1020 | | | | | 1025 | | | |
| AAA | GAT | GAA | GAC | TCT | CCT | AAA | TCT | AAT | GGA | GGA | GGG | TGG | TCC | TTT | ACA | 3442 |
| Lys | Asp | Glu | Asp | Ser | Pro | Lys | Ser | Asn | Gly | Gly | Gly | Trp | Ser | Phe | Thr | |
| | | 1030 | | | | | 1035 | | | | | 1040 | | | | |
| AAC | TTT | TTT | CAG | LAC | AAA | CCA | AAC | GAT | TAACAGTGTC | ACCGTGTCAC | | | | | | 3489 |
| Asn | Phe | Phe | Gln | Asn | Lys | Pro | Asn | Asp | | | | | | | | |
| 1045 | | | | | 1050 | | | | | | | | | | | |

TTCAGTCAGC CATCTCAATA AGCTCTTACT GCTAGTGTTG CTACATCAGC ACTGGGCATT  3549

CTTGGAGGGA TCCTGTGAAG TATTGTTAGG AGGTGAACTT CA  3591

( 2 ) INFORMATION FOR SEQ ID NO:6:

( i ) SEQUENCE CHARACTERISTICS:
        ( A ) LENGTH: 1097 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Met | Asp | Ile | Tyr | Val | Cys | Leu | Lys | Arg | Pro | Ser | Trp | Met | Val | Asp |
|---|---|---|---|---|---|---|---|---|---|---|---|---|---|---|---|
| -44 | | | | -40 | | | | | -35 | | | | | -30 | |

-continued

| | | | | | | | | | | | | | |
|---|---|---|---|---|---|---|---|---|---|---|---|---|---|
| Asn | Lys | Arg | Met -25 | Arg | Thr | Ala | Ser | Asn -20 | Phe | Gln | Trp | Leu -15 | Leu | Ser | Thr |
| Phe | Ile | Leu -10 | Leu | Tyr | Leu | Met | Asn -5 | Gln | Val | Asn | Ser | Gln | Lys | Lys | Gly 1 |
| Ala | Pro | His | Asp | Leu | Lys 10 | Cys | Val | Thr | Asn | Leu 15 | Gln | Val | Trp | Asn 20 |
| Cys | Ser | Trp | Lys | Ala 25 | Pro | Ser | Gly | Thr | Gly 30 | Arg | Gly | Thr | Asp | Tyr 35 | Glu |
| Val | Cys | Ile | Glu 40 | Asn | Arg | Ser | Arg | Ser 45 | Cys | Tyr | Gln | Leu | Glu 50 | Lys | Thr |
| Ser | Ile | Lys 55 | Ile | Pro | Ala | Leu | Ser 60 | His | Gly | Asp | Tyr | Glu 65 | Ile | Thr | Ile |
| Asn | Ser 70 | Leu | His | Asp | Phe | Gly 75 | Ser | Ser | Thr | Ser | Lys 80 | Phe | Thr | Leu | Asn |
| Glu 90 | Gln | Asn | Val | Ser | Leu 95 | Ile | Pro | Asp | Thr | Pro 100 | Glu | Ile | Leu | Asn | Leu |
| Ser | Ala | Asp | Phe | Ser 105 | Thr | Ser | Thr | Leu | Tyr 110 | Leu | Lys | Trp | Asn | Asp 115 | Arg |
| Gly | Ser | Val | Phe 120 | Pro | His | Arg | Ser | Asn 125 | Val | Ile | Trp | Glu | Ile 130 | Lys | Val |
| Leu | Arg | Lys 135 | Glu | Ser | Met | Glu | Leu 140 | Val | Lys | Leu | Val | Thr 145 | His | Asn | Thr |
| Thr | Leu | Asn 150 | Gly | Lys | Asp | Thr | Leu 155 | His | His | Trp | Ser | Trp 160 | Ala | Ser | Asp |
| Met 165 | Pro | Leu | Glu | Cys | Ala 170 | Ile | His | Phe | Val | Glu 175 | Ile | Arg | Cys | Tyr | Ile 180 |
| Asp | Asn | Leu | His | Phe 185 | Ser | Gly | Leu | Glu | Glu 190 | Trp | Ser | Asp | Trp | Ser 195 | Pro |
| Val | Lys | Asn | Ile 200 | Ser | Trp | Ile | Pro | Asp 205 | Ser | Gln | Thr | Lys | Val 210 | Phe | Pro |
| Gln | Asp | Lys 215 | Val | Ile | Leu | Val | Gly 220 | Ser | Asp | Ile | Thr | Phe 225 | Cys | Cys | Val |
| Ser | Gln 230 | Glu | Lys | Val | Leu | Ser 235 | Ala | Leu | Ile | Gly | His 240 | Thr | Asn | Cys | Pro |
| Leu 245 | Ile | His | Leu | Asp | Gly 250 | Glu | Asn | Val | Ala | Ile 255 | Lys | Ile | Arg | Asn | Ile 260 |
| Ser | Val | Ser | Ala | Ser 265 | Ser | Gly | Thr | Asn | Val 270 | Val | Phe | Thr | Thr | Glu 275 | Asp |
| Asn | Ile | Phe | Gly 280 | Thr | Val | Ile | Phe | Ala 285 | Gly | Tyr | Pro | Pro | Asp 290 | Thr | Pro |
| Gln | Gln | Leu 295 | Asn | Cys | Glu | Thr | His 300 | Asp | Leu | Lys | Glu | Ile 305 | Ile | Cys | Ser |
| Trp | Asn 310 | Pro | Gly | Arg | Val | Thr 315 | Ala | Leu | Val | Gly | Pro 320 | Arg | Ala | Thr | Ser |
| Tyr 330 | Thr | Leu | Val | Glu | Ser 335 | Phe | Ser | Gly | Lys | Tyr 340 | Val | Arg | Leu | Lys | Arg |
| Ala | Glu | Ala | Pro | Thr 345 | Asn | Glu | Ser | Tyr | Gln 350 | Leu | Leu | Phe | Gln | Met 355 | Leu |
| Pro | Asn | Gln | Glu 360 | Ile | Tyr | Asn | Phe | Thr 365 | Leu | Asn | Ala | His | Asn 370 | Pro | Leu |
| Gly | Arg | Ser 375 | Gln | Ser | Thr | Ile | Leu 380 | Val | Asn | Ile | Thr | Glu 385 | Lys | Val | Tyr |
| Pro | His 390 | Thr | Pro | Thr | Ser | Phe 395 | Lys | Val | Lys | Asp | Ile 400 | Asn | Ser | Thr | Ala |
| Val | Lys | Leu | Ser | Trp | His | Leu | Pro | Gly | Asn | Phe | Ala | Lys | Ile | Asn | Phe |

```
405                      410                      415                      420
Leu Cys Glu Ile Glu Ile Lys Lys Ser Asn Ser Val Gln Glu Gln Arg
                    425             430             435
Asn Val Thr Ile Lys Gly Val Glu Asn Ser Ser Tyr Leu Val Ala Leu
                440             445             450
Asp Lys Leu Asn Pro Tyr Thr Leu Tyr Thr Phe Arg Ile Arg Cys Ser
            455             460             465
Thr Glu Thr Phe Trp Lys Trp Ser Lys Trp Ser Asn Lys Lys Gln His
        470             475             480
Leu Thr Thr Glu Ala Ser Pro Ser Lys Gly Pro Asp Thr Trp Arg Glu
485             490             495                         500
Trp Ser Ser Asp Gly Lys Asn Leu Ile Ile Tyr Trp Lys Pro Leu Pro
                505             510             515
Ile Asn Glu Ala Asn Gly Lys Ile Leu Ser Tyr Asn Val Ser Cys Ser
                520             525             530
Ser Asp Glu Glu Thr Gln Ser Leu Ser Glu Ile Pro Asp Pro Gln His
        535             540             545
Lys Ala Glu Ile Arg Leu Asp Lys Asn Asp Tyr Ile Ile Ser Val Val
    550             555             560
Ala Lys Asn Ser Val Gly Ser Ser Pro Pro Ser Lys Ile Ala Ser Met
565             570             575                         580
Glu Ile Pro Asn Asp Asp Leu Lys Ile Glu Gln Val Val Gly Met Gly
                585             590             595
Lys Gly Ile Leu Leu Thr Trp His Tyr Asp Pro Asn Met Thr Cys Asp
            600             605             610
Tyr Val Ile Lys Trp Cys Asn Ser Ser Arg Ser Glu Pro Cys Leu Met
        615             620             625
Asp Trp Arg Lys Val Pro Ser Asn Ser Thr Glu Thr Val Ile Glu Ser
630                 635             640
Asp Glu Phe Arg Pro Gly Ile Arg Tyr Asn Phe Phe Leu Tyr Gly Cys
645             650             655                         660
Arg Asn Gln Gly Tyr Gln Leu Leu Arg Ser Met Ile Gly Tyr Ile Glu
                665             670             675
Glu Leu Ala Pro Ile Val Ala Pro Asn Phe Thr Val Glu Asp Thr Ser
            680             665             690
Ala Asp Ser Ile Leu Val Lys Trp Glu Asp Ile Pro Val Glu Glu Leu
        695             700             705
Arg Gly Phe Leu Arg Gly Tyr Leu Phe Tyr Phe Gly Lys Gly Glu Arg
    710             715             720
Asp Thr Ser Lys Met Arg Val Leu Glu Ser Gly Arg Ser Asp Ile Lys
725             730             735                         740
Val Lys Asn Ile Thr Asp Ile Ser Gln Lys Thr Leu Arg Ile Ala Asp
                745             750             755
Leu Gln Gly Lys Thr Ser Tyr His Leu Val Leu Arg Ala Tyr Thr Asp
            760             765             770
Gly Gly Val Gly Pro Glu Lys Ser Met Tyr Val Val Thr Lys Glu Asn
        775             780             785
Ser Val Gly Leu Ile Ile Ala Ile Leu Ile Pro Val Ala Val Ala Val
    790             795             800
Ile Val Gly Val Val Thr Ser Ile Leu Cys Tyr Arg Lys Arg Glu Trp
805             810             815                         820
Ile Lys Glu Thr Phe Tyr Pro Asp Ile Pro Asn Pro Glu Asn Cys Lys
                825             830             835
Ala Leu Gln Phe Gln Lys Ser Val Cys Glu Gly Ser Ser Ala Leu Lys
            840             845             850
```

-continued

```
Thr Leu Glu Met Asn Pro Cys Thr Pro Asn ASn Val Glu Val Leu Glu
        855             860             865
Thr Arg Ser Ala Phe Pro Lys Ile Glu Asp Thr Glu Ile Ile Ser Pro
    870             875             880
Val Ala Glu Arg Pro Glu Asp Arg Ser Asp Ala Glu Pro Glu Asn His
885             890             895                             900
Val Val Val Ser Tyr Cys Pro Pro Ile Ile Glu Glu Glu Ile Pro Asn
                905             910                         915
Pro Ala Ala Asp Glu Ala Gly Gly Thr Ala Gln Val Ile Tyr Ile Asp
            920             925                     930
Val Gln Ser Met Tyr Gln Pro Gln Ala Lys Pro Glu Glu Glu Gln Glu
        935             940             945
Asn Asp Pro Val Gly Gly Ala Gly Tyr Lys Pro Gln Met His Leu Pro
        950             955             960
Ile Asn Ser Thr Val Glu Asp Ile Ala Ala Glu Asp Leu Asp Lys
965             970             975                         980
Thr Ala Gly Tyr Arg Pro Gln Ala Asn Val Asn Thr Trp Asn Leu Val
                985             990                         995
Ser Pro Asp Ser Pro Arg Ser Ile Asp Ser Asn Ser Glu Ile Val Ser
            1000            1005                    1010
Phe Gly Ser Pro Cys Ser Ile Asn Ser Arg Gln Phe Leu Ile Pro Pro
            1015            1020                    1025
Lys Asp Glu Asp Ser Pro Lys Ser Asn Gly Gly Gly Trp Ser Phe Thr
    1030            1035                    1040
Asn Phe Phe Gln Asn Lys Pro Asn Asp
1045            1050
```

( 2 ) INFORMATION FOR SEQ ID NO:7:

( i ) SEQUENCE CHARACTERISTICS:
        ( A ) LENGTH: 745 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i i ) IMMEDIATE SOURCE:
        ( B ) CLONE: hIgG1Fc ( i x ) FEATURE:
        ( A ) NAME/KEY: CDS
        ( B ) LOCATION: 2739

( x i ) SEQUENCE DESCRIPTION: SEQ ID NO:7:

```
G GTA CCG CTA GCG TCG ACA GGC CTA GGA TAT CGA TAC GTA GAG CCC         46
  Val Pro Leu Ala Ser Thr Gly Leu Gly Tyr Arg Tyr Val Glu Pro
  1               5                   10                  15

AGA TCT TGT GAC AAA ACT CAC ACA TGC CCA CCG TGC CCA GCA CCT GAA       94
Arg Ser Cys Asp Lys Thr His Thr Cys Pro Pro Cys Pro Ala Pro Glu
                20                  25                  30

CTC CTG GGG GGA CCG TCA GTC TTC CTC TTC CCC CCA AAA CCC AAG GAC      142
Leu Leu Gly Gly Pro Ser Val Phe Leu Phe Pro Pro Lys Pro Lys Asp
            35                  40                  45

ACC CTC ATG ATC TCC CGG ACC CCT GAG GTC ACA TGC GTG GTG GTG GAC      190
Thr Leu Met Ile Ser Arg Thr Pro Glu Val Thr Cys Val Val Val Asp
        50                  55                  60

GTG AGC CAC GAA GAC CCT GAG GTC AAG TTC AAC TGG TAC GTG GAC GGC      238
Val Ser His Glu Asp Pro Glu Val Lys Phe Asn Trp Tyr Val Asp Gly
    65                  70                  75

GTG GAG GTG CAT AAT GCC AAG ACA AAG CCG CGG GAG GAG CAG TAC AAC      286
```

| | | | | | | | | | | | | | | | | |
|---|---|---|---|---|---|---|---|---|---|---|---|---|---|---|---|---|
| Val | Glu | Val | His | Asn | Ala | Lys | Thr | Lys | Pro | Arg | Glu | Glu | Gln | Tyr | Asn | |
| 80 | | | | 85 | | | | | 90 | | | | | 95 | | |

| AGC | ACG | TAC | CGG | GTG | GTC | AGC | GTC | CTC | ACC | GTC | CTG | CAC | CAG | GAC | TGG | 334 |
|---|---|---|---|---|---|---|---|---|---|---|---|---|---|---|---|---|
| Ser | Thr | Tyr | Arg | Val | Val | Ser | Val | Leu | Thr | Val | Leu | His | Gln | Asp | Trp | |
| | | | | 100 | | | | | 105 | | | | | 110 | | |

| CTG | AAT | GGC | AAG | GAC | TAC | AAG | TGC | AAG | GTC | TCC | AAC | AAA | GCC | CTC | CCA | 382 |
|---|---|---|---|---|---|---|---|---|---|---|---|---|---|---|---|---|
| Leu | Asn | Gly | Lys | Asp | Tyr | Lys | Cys | Lys | Val | Ser | Asn | Lys | Ala | Leu | Pro | |
| | | | 115 | | | | | 120 | | | | | 125 | | | |

| GCC | CCC | ATG | CAG | AAA | ACC | ATC | TCC | AAA | GCC | AAA | GGG | CAG | CCC | CGA | GAA | 430 |
|---|---|---|---|---|---|---|---|---|---|---|---|---|---|---|---|---|
| Ala | Pro | Met | Gln | Lys | Thr | Ile | Ser | Lys | Ala | Lys | Gly | Gln | Pro | Arg | Glu | |
| | | 130 | | | | | 135 | | | | | 140 | | | | |

| CCA | CAG | GTG | TAC | ACC | CTG | CCC | CCA | TCC | CGG | GAT | GAG | CTG | ACC | AAG | AAC | 478 |
|---|---|---|---|---|---|---|---|---|---|---|---|---|---|---|---|---|
| Pro | Gln | Val | Tyr | Thr | Leu | Pro | Pro | Ser | Arg | Asp | Glu | Leu | Thr | Lys | Asn | |
| 145 | | | | | 150 | | | | | 155 | | | | | | |

| CAG | GTC | AGC | CTG | ACC | TGC | CTG | GTC | AAA | GGC | TTC | TAT | CCC | AGG | CAC | ATC | 526 |
|---|---|---|---|---|---|---|---|---|---|---|---|---|---|---|---|---|
| Gln | Val | Ser | Leu | Thr | Cys | Leu | Val | Lys | Gly | Phe | Tyr | Pro | Arg | His | Ile | |
| 160 | | | | | 165 | | | | | 170 | | | | | 175 | |

| GCC | GTG | GAG | TGG | GAG | AGC | AAT | GGG | CAG | CCG | GAG | AAC | AAC | TAC | AAG | ACC | 574 |
|---|---|---|---|---|---|---|---|---|---|---|---|---|---|---|---|---|
| Ala | Val | Glu | Trp | Glu | Ser | Asn | Gly | Gln | Pro | Glu | Asn | Asn | Tyr | Lys | Thr | |
| | | | | 180 | | | | | 185 | | | | | 190 | | |

| ACG | CCT | CCC | GTG | CTG | GAC | TCC | GAC | GGC | TCC | TTC | TTC | CTC | TAC | AGC | AAG | 622 |
|---|---|---|---|---|---|---|---|---|---|---|---|---|---|---|---|---|
| Thr | Pro | Pro | Val | Leu | Asp | Ser | Asp | Gly | Ser | Phe | Phe | Leu | Tyr | Ser | Lys | |
| | | | 195 | | | | | 200 | | | | | 205 | | | |

| CTC | ACC | GTG | GAC | AAG | AGC | AGG | TGG | CAG | CAG | GGG | AAC | GTC | TTC | TCA | TGC | 670 |
|---|---|---|---|---|---|---|---|---|---|---|---|---|---|---|---|---|
| Leu | Thr | Val | Asp | Lys | Ser | Arg | Trp | Gln | Gln | Gly | Asn | Val | Phe | Ser | Cys | |
| | | 210 | | | | | 215 | | | | | 220 | | | | |

| TCC | GTG | ATG | CAT | GAG | GCT | CTG | CAC | AAC | CAC | TAC | ACG | CAG | AAG | AGC | CTC | 718 |
|---|---|---|---|---|---|---|---|---|---|---|---|---|---|---|---|---|
| Ser | Val | Met | His | Glu | Ala | Leu | His | Asn | His | Tyr | Thr | Gln | Lys | Ser | Leu | |
| | 225 | | | | | 230 | | | | | 235 | | | | | |

| TCC | CTG | TCT | CCG | GGT | AAA | TGAACTAGT | | | | | | 746 |
|---|---|---|---|---|---|---|---|---|---|---|---|---|
| Ser | Leu | Ser | Pro | Gly | Lys | | | | | | | |
| 240 | | | | | 245 | | | | | | | |

( 2 ) INFORMATION FOR SEQ ID NO:8:

( i ) SEQUENCE CHARACTERISTICS:
        ( A ) LENGTH: 245 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Val | Pro | Leu | Ala | Ser | Thr | Gly | Leu | Gly | Tyr | Arg | Tyr | Val | Glu | Pro | Arg |
|---|---|---|---|---|---|---|---|---|---|---|---|---|---|---|---|
| 1 | | | | 5 | | | | | 10 | | | | | 15 | |

| Ser | Cys | Asp | Lys | Thr | His | Thr | Cys | Pro | Cys | Pro | Ala | Pro | Glu | Leu |
|---|---|---|---|---|---|---|---|---|---|---|---|---|---|---|
| | | | 20 | | | | | 25 | | | | 30 | | |

| Leu | Gly | Gly | Pro | Ser | Val | Phe | Leu | Phe | Pro | Pro | Lys | Pro | Lys | Asp | Thr |
|---|---|---|---|---|---|---|---|---|---|---|---|---|---|---|---|
| | | 35 | | | | | 40 | | | | | 45 | | | |

| Leu | Met | Ile | Ser | Arg | Thr | Pro | Glu | Val | Thr | Cys | Val | Val | Val | Asp | Val |
|---|---|---|---|---|---|---|---|---|---|---|---|---|---|---|---|
| | 50 | | | | | 55 | | | | | 60 | | | | |

| Ser | His | Glu | Asp | Pro | Glu | Val | Lys | Phe | Asn | Trp | Tyr | Val | Asp | Gly | Val |
|---|---|---|---|---|---|---|---|---|---|---|---|---|---|---|---|
| 65 | | | | | 70 | | | | | 75 | | | | | 80 |

| Glu | Val | His | Asn | Ala | Lys | Thr | Lys | Pro | Arg | Glu | Glu | Gln | Tyr | Asn | Ser |
|---|---|---|---|---|---|---|---|---|---|---|---|---|---|---|---|
| | | | | 85 | | | | | 90 | | | | | 95 | |

| Thr | Tyr | Arg | Val | Val | Ser | Val | Leu | Thr | Val | Leu | His | Gln | Asp | Trp | Leu |
|---|---|---|---|---|---|---|---|---|---|---|---|---|---|---|---|
| | | | 100 | | | | | 105 | | | | | 110 | | |

| Asn | Gly | Lys | Asp | Tyr | Lys | Cys | Lys | Val | Ser | Asn | Lys | Ala | Leu | Pro | Ala |
|---|---|---|---|---|---|---|---|---|---|---|---|---|---|---|---|
| | | 115 | | | | | 120 | | | | | 125 | | | |

| Pro | Met | Gln | Lys | Thr | Ile | Ser | Lys | Ala | Lys | Gly | Gln | Pro | Arg | Glu | Pro |
|---|---|---|---|---|---|---|---|---|---|---|---|---|---|---|---|
| | 130 | | | | | 135 | | | | | 140 | | | | |

| Gln | Val | Tyr | Thr | Leu | Pro | Pro | Ser | Arg | Asp | Glu | Leu | Thr | Lys | Asn | Gln |
|---|---|---|---|---|---|---|---|---|---|---|---|---|---|---|---|

| 145 | | | | | 150 | | | | | 155 | | | | | 160 |
|---|---|---|---|---|---|---|---|---|---|---|---|---|---|---|---|
| Val | Ser | Leu | Thr | Cys 165 | Leu | Val | Lys | Gly | Phe 170 | Tyr | Pro | Arg | His | Ile 175 | Ala |
| Val | Glu | Trp | Glu 180 | Ser | Asn | Gly | Gln | Pro 185 | Glu | Asn | Asn | Tyr | Lys 190 | Thr | Thr |
| Pro | Pro | Val 195 | Leu | Asp | Ser | Asp | Gly 200 | Ser | Phe | Phe | Leu | Tyr 205 | Ser | Lys | Leu |
| Thr | Val 210 | Asp | Lys | Ser | Arg | Trp 215 | Gln | Gln | Gly | Asn | Val 220 | Phe | Ser | Cys | Ser |
| Val 225 | Met | His | Glu | Ala | Leu 230 | His | Asn | His | Tyr | Thr 235 | Gln | Lys | Ser | Leu | Ser 240 |
| Leu | Ser | Pro | Gly | Lys 245 | | | | | | | | | | | |

We claim:

1. A substantially homogeneous purified LIF receptor (LIF-R) protein comprising an amino acid sequence selected from the group consisting of amino acids 1–957 of SEQ ID NO:2, amino acids 1–45 of SEQ ID NO: 2, amino acids 1–76 of SEQ ID NO:4, and amino acids 1–1053 of SEQ ID NO:6.

2. A substantially homogeneous purified LIF receptor (LIF-R) protein capable of binding LIF, wherein said LIF-R in encoded by a DNA selected from the group consisting of:
  (a) a DNA comprising the coding region of the DNA sequence of SEQ ID NO: 1;
  (b) A DNA comprising the coding region of the DNA sequence of SEQ ID NO: 3;
  (c) a DNA comprising the coding region of the DNA sequence of SEQ ID NO: 5;
  (d) a DNA that hybridize to the complement of a DNA of (a), (b) or (c) under moderately stringent conditions and which encodes a LFF-R capable of binding LIF; and
  (e) A DNA that is degenerate as a result of the genetic codd to a DNA of (a), (b), (c), or (d).

3. A purified LIF-R protein according to claim 2, wherein said LIF-R protein is a human LIF-R protein comprising an amino acid sequence selected from the group consisting of amino acids 1–957 of SEQ ID NO: 1, amino acids 1–945 of SEQ ID NO: 1, and amino acids 1–1053 of SEQ ID NO: 5, except for modification(s) selected from the group consisting of:
  a) inactivation of N-glycosylation site(s);
  b) inactivation of KEX2 protease processing site(s);
  c) addition of an N-terminal methionine residue; and
  d) conservative amino acid substitution(s).

4. A homodimeric receptor comprising two fusion proteins joined via disulfide bonds, wherein each fusion protein comprises a human LIF-R polypeptide fused to an antibody Fc polypeptide, wherein said LIF-R polypeptide comprises an amino acid sequence extending from amino acids x to y of SEQ ID NO:1, wherein x is 1 to 11 and y is 479 to 789, wherein said fusion protein may additionally comprise a peptide linker between said LIF-R polypeptide and said Fc polypeptide.

5. A homodimeric receptor according to claim 4, wherein x is 1 and y is selected from the group consisting of 702, 775, and 789.

6. A composition comprising a LIF receptor (LIF-R) protein according to claim 4 and a suitable diluent or carrier.

* * * * *